(12) United States Patent
Chong et al.

(10) Patent No.: US 9,365,892 B2
(45) Date of Patent: Jun. 14, 2016

(54) SCREENING METHOD FOR TRINUCLEOTIDE REPEAT SEQUENCES

(75) Inventors: Siong-Chuan Samuel Chong, Singapore (SG); Ru Lin Clara Teo, Singapore (SG); Guat Lay Caroline Lee, Singapore (SG)

(73) Assignee: National University of Singapore, Singapore (SG)

( * ) Notice: Subject to any disclaimer, the term of this patent is extended or adjusted under 35 U.S.C. 154(b) by 55 days.

(21) Appl. No.: 13/501,972

(22) PCT Filed: Oct. 15, 2010

(86) PCT No.: PCT/SG2010/000396
§ 371 (c)(1),
(2), (4) Date: Jun. 27, 2012

(87) PCT Pub. No.: WO2011/046518
PCT Pub. Date: Apr. 21, 2011

(65) Prior Publication Data
US 2012/0264125 A1    Oct. 18, 2012

Related U.S. Application Data

(60) Provisional application No. 61/252,182, filed on Oct. 16, 2009.

(51) Int. Cl.
*C12Q 1/68* (2006.01)
(52) U.S. Cl.
CPC ............ *C12Q 1/6827* (2013.01); *C12Q 1/6883* (2013.01); *C12Q 2600/154* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 6,143,504 A | 11/2000 | Das et al. |
| 8,679,757 B2 | 3/2014 | Latham et al. |
| 2003/0170649 A1 | 9/2003 | Haas et al. |

FOREIGN PATENT DOCUMENTS

| ES | 2257107 A1 | 7/2006 |
| KR | 100842432 B | 7/2008 |
| WO | WO-2011/046518 A1 | 4/2011 |
| WO | WO 2011/097503 A2 | 8/2011 |

OTHER PUBLICATIONS

Zhou et al. Clinical Chemistry 2006; 52(8): 1492-1500.*
Tassone et al. American Journal of Medical Genetics 2000; 94: 232-236.*
Teo et al. Clinical Chemistry 2008; 54(6): 964-972.*
Gundry et al. (2002). SYBR Green I Analysis of the Trinucleotide Repeat Responsible for Huntington's Disease. In W. Dietmaier et al. (eds.), Rapid Cycle Real-Time PCR—Methods and Applications. Berlin: Springer-Verlag.*
International Search Report and Written Opinion mailed Dec. 23, 2010 in connection with PCT/SG2010/000396.
International Preliminary Report on Patentability mailed Apr. 26, 2012 in connection with PCT/SG2010/000396.
Warner et al., A general method for the detection of large CAG repeat expansions by fluorescent PCR. J Med Genet. Dec. 1996;33(12):1022-6.
Zhou et al., Robust fragile X (CGG)n genotype classification using a methylation specific triple PCR assay. J Med Genet. Apr. 2004;41(4):e45.
Carrel et al., An assay for X inactivation based on differential methylation at the fragile X locus, FMR1. Am J Med Genet. Jul. 12, 1996;64(1):27-30.
Falk et al., Simple procedure for automatic detection of unstable alleles in the myotonic dystrophy and Huntington's disease loci. Genet Test. 2006 Summer;10(2):85-97.
Gorodkin et al., Porcine transcriptome analysis based on 97 non-normalized cDNA libraries and assembly of 1,021,891 expressed sequence tags. Genome Biol. 2007; 8(4): R45. Published online Apr 2, 2007. doi: 10.1186/gb-2007-8-4-r45.
Tassone et al., A Rapid Polymerase Chain Reaction-Based Screening Method for Identification of All Expanded Alleles of the Fragile X (FMR1) Gene in Newborn and High-Risk Populations. J Mol Diagn. Jan. 2008; 10(1): 43-49. doi: 10.2353/jmoldx.2008.070073.

* cited by examiner

*Primary Examiner* — Angela M Bertagna
(74) *Attorney, Agent, or Firm* — Wolf, Greenfield & Sacks, P.C.

(57) ABSTRACT

A method for screening for a trinucleotide repeat sequence in a biological sample is provided. The method comprises the step of contacting a nucleic acid sequence obtained or derived from the biological sample under amplification conditions with i) a first primer having a target sequence in a region 3' or 5' of a trinucleotide repeat sequence; ii) a second primer having a target sequence within the trinucleotide repeat sequence and a unique 5' tail sequence; and iii) a third primer, having a target within the unique 5' tail sequence of the second primer to generate an amplified product comprising a trinucleotide repeat sequence. Primers, kits of primers together with the use of the primers in methods of screening are also provided.

27 Claims, 32 Drawing Sheets

FIGURE 12
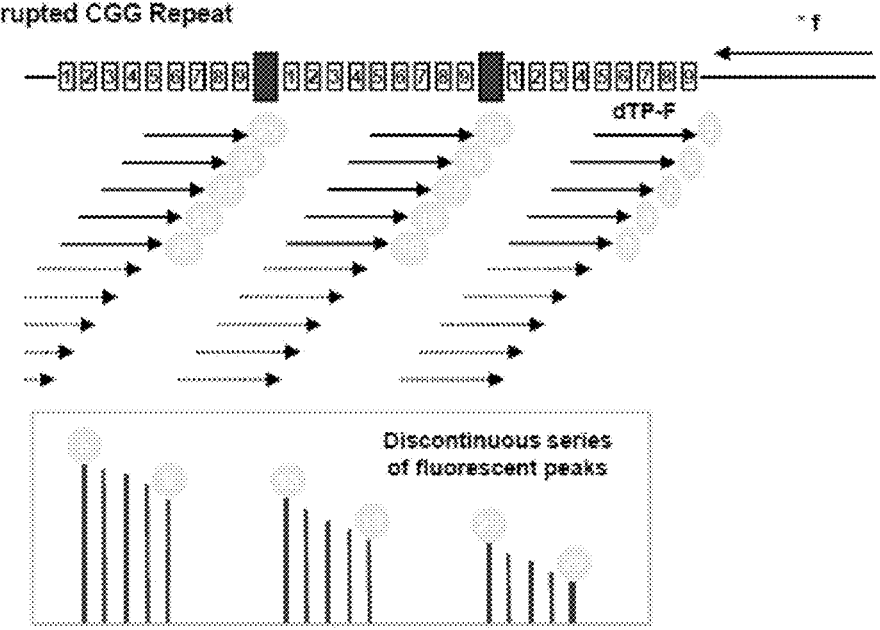
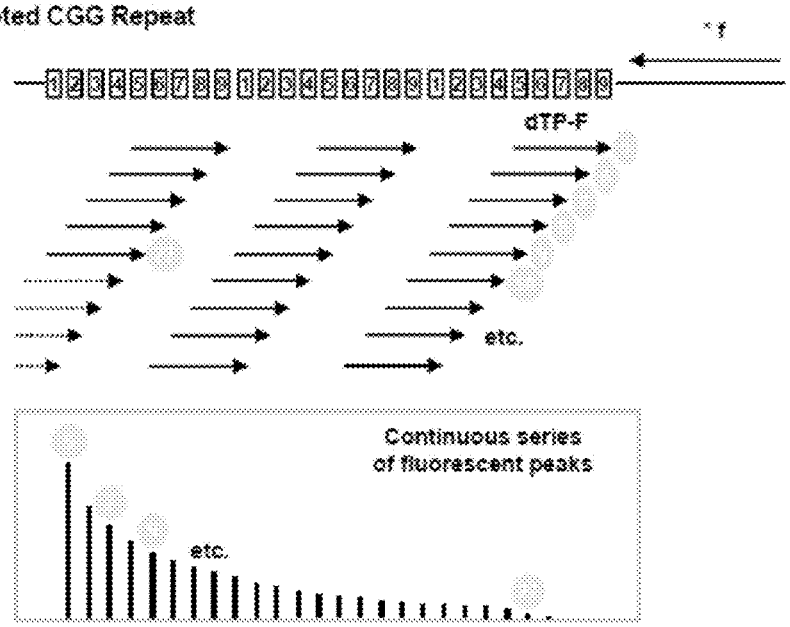

SCREENING METHOD FOR TRINUCLEOTIDE REPEAT SEQUENCES

This application is a U.S. national stage application based on International Application No. PCT/SG2010/000396, filed Oct. 15, 2010, which claims priority under 35 U.S.C. §119 (e)to U.S. Provisional Application Ser. No. 61/252,182, filed Oct. 16, 2009, the contents of which are incorporated herein by reference in their entirety.

TECHNICAL FIELD

The present disclosure relates to methods for screening for a trinucleotide repeat sequence, and in particular the screening of trinucleotide repeat sequence disorders. More specifically, the present disclosure relates to primers for use in polymerase chain reaction based tests, capable of screening for trinucleotide repeat sequence disorders. Kits of primers are also provided, together with the use of the primers in methods of screening.

BACKGROUND

Many inherited diseases are the result of a single difference in the genetic code for a particular protein. As a result of that difference, either a protein is not made at all, made in inadequate amounts, or made in a defective form. The disease is therefore a result of a person either not making a protein or not making enough of a protein, or having a defective form of it.

In the early 1990's, researchers identified a new type of mutation called dynamic or expansion mutations. Researchers had noted that in a variety of diseases, there was an increase in severity of a disease or earlier onset of a disease over several generations. Today we understand these diseases to be trinucleotide repeat sequence disorders.

A trinucleotide repeat sequence disorder, also known as a trinucleotide repeat disorder, a trinucleotide repeat expansion disorder or a triplet repeat expansion disorder, is a genetic disorder caused by an increase in the number of trinucleotide repeats in a, gene exceeding a normal, stable, threshold.

Trinucleotide repeat sequence disorders are divided into two categories determined by the type of repeat. The most common repeat is a repeat of the triplet nucleotide sequence CAG which, when present in the coding region of gene, codes for the amino acid glutamine (Q). Therefore, these disorders are referred to as polyglutamine (polyQ) disorders. Disorders that not involve a repeat of the CAG triplet nucleotide sequence, or in which a CAG triplet nucleotide sequence is not in the coding region of the gene are referred to as non-polyglutamine disorders.

Fragile X syndrome (FXS) is the most common inherited mental retardation disorder, which results in a spectrum of physical and intellectual limitations and emotional and behavioral features which range from severe to mild in manifestation. FXS is also the most common known cause of autism or "autistic-like" behaviors which can include its characteristic physical and behavioral features as well as delays in speech and language development.

The X-linked Fragile X Mental Retardation 1. (FMR1) gene is responsible for FXS. Most FMR1 gene mutations involve expansions of a polymorphic stretch of CGG repeats in its 5' untranslated region. Unaffected individuals carry alleles ranging from 6 to 44 repeats, which are stably transmitted from generation to generation. Individuals with FXS carry full mutation alleles with >200 repeats which is accompanied by hypermethylation of the FMR1 promoter region and gene silencing. Alleles with 45 to 54 repeats are classified as gray zone alleles. Although gray zone alleles are associated with some degree of size instability, they are more stable than premutation alleles, which range from 55 to ~200 repeats. Premutation alleles are meiotically unstable and may expand from one generation to the next. These alleles have also been associated with high transcript but low peptide levels and may be linked to disorders that are clinically distinct from FXS, such as fragile X-associated tremor ataxia syndrome (FXTAS) in males and premature ovarian failure (POF) in females.

The FMR1 CGG repeat is normally interspersed by AGG trinucleotide interruptions after every 9 or 10 CGGs, with most normal alleles containing two AGG interruptions and most premutation alleles containing only one AGG interruption at the 5' end of the repeat region or none at all. The loss of an AGG interruption, especially at the 3' end of a repeat region, results in a long stretch of uninterrupted CGG repeats that has been associated with CGG repeat instability, especially in alleles with >24 uninterrupted CGG repeats at the 3' end of the repeat.

The FMR1 gene is located on the X chromosome. Therefore, since a female has two X chromosomes, a female with a premutation or full mutation has a 50% chance of passing on the X with the mutation in each pregnancy. If she has a premutation, this can be passed onto her offspring where it can either remain as a premutation or it can expand to a full mutation. Unlike many other X-linked conditions where only males who inherit the abnormal gene are affected (since they only have one X chromosome and do not have another normal copy to compensate), females can also be affected by FXS.

At this time, there is no, cure for FXS. Currently, the syndrome is treated through a combination of behavioral therapy, special education, and when necessary, treatment of physical abnormalities. Persons with relatives suffering from FXS are advised to seek genetic counseling to assess the likelihood of having children who are affected, and how severe any impairments may be in affected descendants. This is especially important because individuals who carry the premutation alleles are non-symptomatic and it may not be readily apparent that such an individual is at risk of having offspring with FXS.

The most commonly used method of diagnosis of FXS is DNA testing by PCR amplification across the triplet repeat stretch, supplemented by Southern blot analysis. While PCR analysis is able to size all normal and gray zone alleles, as well as small premutation alleles, larger expansions are refractory to PCR amplification due to their large amplicon sizes and high GC contents. Conventional PCR based approaches are also unable to provide information on the methylation states of the repeats.

Conversely, Southern blot analysis can detect large expansion mutations but cannot accurately distinguish large normal or gray zone alleles from small premutation alleles, requires large amounts of DNA and is also highly labour-intensive. Currently, a combination of both methods is necessary to ensure accurate FMR1 CGG repeat classification, making molecular diagnosis and screening of suspected FXS patients time-consuming and costly.

To get around this problem, several methylation-specific PCR methods have been developed to detect FMR1 CGG repeat expansions, taking advantage of sequence variations between methylated and unmethylated DNA after treatment with sodium bisulfite to assist in discrimination between normal and expanded alleles. Sodium bisulfite treated DNA is also less GC rich and easier to amplify. However, these assays often involve multiple PCR reactions, or can only be used for analysis of male samples. Also, since FMR1 resides on the X chromosome, interpretation of assay results of females are often complicated by the presence of two X chromosomes, one of which will be inactivated for X-linked gene dosage compensation.

Presently, the absence of a quick and robust genetic screen for FXS and its related syndromes is one of the main limiting factors to the implementation of a routine genetic screen of the FMR1 locus. Hence, there is an urgent need for improved methods for screening for FXS.

There is a need to provide a fast reliable method that overcomes, or at least ameliorates, one or more of the disadvantages described above.

SUMMARY

According to a first aspect, there is provided a method for screening for a trinucleotide repeat sequence in a biological sample, wherein said method comprises the step of contacting a nucleic acid sequence obtained or derived from the biological sample under amplification conditions with:
i) a first primer, wherein said first primer has a target sequence in a region 3' or 5' of a trinucleotide repeat sequence in the nucleic acid sequence;
ii) a second primer, wherein said second primer has a target sequence within the trinucleotide repeat sequence in the nucleic acid sequence and a unique 5' tail sequence; and
iii) a third primer, wherein the target sequence of the said second forward primer is within the unique 5' tail sequence of the second primer
to generate an amplified product comprising a trinucleotide repeat sequence.

According to a second aspect there is provided a method for screening for a trinucleotide repeat sequence in a biological sample, wherein said method comprises the step of contacting a nucleic acid sequence obtained or derived from the biological sample under amplification conditions with:
i) a first primer, wherein said first primer has a target sequence in a region 3' or 5' of a trinucleotide repeat sequence in the nucleic acid sequence;
ii) a second primer, wherein said second primer has a target sequence within the trinucleotide repeat sequence in the nucleic acid sequence;
to generate an amplified product comprising trinucleotide repeat sequence; and
analyzing said amplified product using DNA melt curve analysis.

According to a third aspect, there is provided a method for screening for a trinucleotide repeat sequence in a biological sample, wherein said method comprises the step of contacting a nucleic acid sequence obtained or derived from the biological sample under amplification conditions, wherein said nucleic acid has been pre-treated with a reagent which selectively modifies unmethylated cytosine residues in the nucleotide sequence, with:
  i) a first primer, wherein said first primer has a target sequence in a region 3' and/or 5' of a trinucleotide repeat sequence in the nucleic acid sequence;
  ii) a second primer, wherein said second primer has a target sequence within the trinucleotide repeat sequence in the nucleic acid sequence and said primer is complementary to a methylated trinucleotide repeat sequence;
  iii) a further second primer, wherein said further second primer has a target sequence within the trinucleotide repeat sequence in the nucleic acid sequence and said primer is complementary to an unmethylated trinucleotide repeat sequence
to generate an amplified product comprising a trinucleotide repeat sequence; and
analyzing said amplified product using DNA melt curve analysis.

According to a fourth aspect there is provided a primer selected from the group comprising or consisting of the nucleotide sequence of any of SEQ ID NO:1 to SEQ ID NO:27 or complements thereof.

According to a fifth aspect, there is provided a primer comprising or consisting of a nucleotide sequence in which the nucleotide sequence comprises:
  (i) a first sequence selected from the group consisting of any one of SEQ ID NO:13, SEQ ID NO:14 and SEQ ID NO:15; and
  (ii) a unique sequence selected from the group consisting of any one of SEQ ID NO:16, SEQ ID NO:17, SEQ ID NO:18; and SEQ ID NO:19.

According to a sixth aspect, there is provided a set of primers for screening for a trinucleotide repeat sequence, in which the nucleotide sequences of the primers comprise or consist of the following sequences, or complements thereof: SEQ ID NO:1, SEQ ID NO:2, and SEQ ID NO:3.

According to a seventh aspect, there is provided a set of primers for screening for a trinucleotide repeat sequence, in which the nucleotide sequences of the primers comprise or consist of the following sequences, or complements thereof: SEQ ID NO:4, SEQ ID NO:5, SEQ ID NO:6 and SEQ ID NO:20.

According to an eighth aspect, there is provided a set of primers for screening for a trinucleotide repeat sequence, in which the nucleotide sequences of the primers comprise or consist of of the following sequences, or complements thereof: SEQ ID NO:7, SEQ ID NO:8, and SEQ ID NO:9.

According to a ninth aspect, there is provided a set of primers for screening for a trinucleotide repeat sequence, in which the nucleotide sequences of the primers comprise or consist of the following sequences, or complements thereof: SEQ ID NO:10, SEQ ID NO:11, and SEQ ID NO:12.

According to a tenth aspect, there is provided a set of primers for screening for a trinucleotide repeat sequence, in which the nucleotide sequences of the primers comprise or consist of the following sequences, or complements thereof: SEQ ID NO:21, SEQ ID NO:22, and SEQ ID NO:23.

According to an eleventh aspect, there is provided a set of primers for screening for a trinucleotide repeat sequence, in which the nucleotide sequences of the primers comprise or consist of the following sequences, or complements thereof: SEQ ID NO:3, SEQ ID NO:24, and SEQ ID NO:25.

According to a twelfth aspect, there is provided a set of primers for screening for a trinucleotide repeat sequence, in which the nucleotide sequences of the primers comprise or consist of the following sequences, or complements thereof: SEQ ID NO:6, SEQ ID NO:26, and SEQ ID NO:27.

According to a thirteenth aspect there is provided a kit when used in the method according to the disclosure comprising:
one or more primers, in which the nucleotide sequences comprise or consist of the following sequences, or complements thereof: SEQ ID NO.1, SEQ ID NO.2, SEQ ID NO.3 and SEQ ID NO.4, SEQ ID NO:5, SEQ ID NO:6 and SEQ ID NO:20; or
one or more primers, in which the nucleotide sequences comprise or consist of the following sequences, or complements thereof: SEQ ID NO.7, SEQ ID NO.8, and SEQ ID. NO.9; or one or more primers, in which the nucleotide sequences comprise or consist of the following sequences, or complements thereof SEQ ID NO.10, SEQ ID NO:11 and SEQ ID NO:12; or one or more primers, in which the nucleotide sequences comprise or consist of the following sequences, or complements thereof: SEQ ID NO.21, SEQ ID NO.22, and SEQ ID NO.23; or one or more primers, in which the nucleotide sequences comprise or consist of the following sequences, or complements thereof: SEQ ID NO:3, SEQ ID NO:24 and SEQ ID NO:25; or one or more primers, in which the nucleotide sequences comprise or consist of the following sequences, or complements thereof: SEQ ID NO:6, SEQ ID NO:26 and SEQ ID NO:27, optionally together with instructions for use.

It is an advantage of the present disclosure that reliable results can be obtained within 24 hours and only requires one PCR reaction set up.

It is a further advantage that the method of the disclosure can clearly distinguish very large premutation alleles from full mutation alleles in both males and females.

It is a further advantage that the method according to the disclosure does not require validation by southern blot analysis.

It is a further advantage of the present disclosure that permutation females that are mosaic for permutation and full mutation alleles can be immediately identified.

BRIEF DESCRIPTION OF FIGURES, TABLES AND SEQUENCES

Figures

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1 is a schematic illustration of the principle of the FMR1 duplex methylation-specific triplet-primed PCR (msTP-PCR) procedure. The effect of sodium bisulfite treatment of unmethylated and methylated alleles of the FMR1 CGG repeat on nucleotide sequences of sense and antisense DNA strands is shown. $(CAA)_9$ are residues 22 to 48 of SEQ ID: 1, and $(CGA)_8$ are residues 22 to 45 of SEQ ID No: 4.

FIG. 2 is a schematic illustration of how the presence or absence of AGG interruptions affects primer annealing within the triplet repeat, and the resultant PCR product electropherogram patterns using the msTP-PCR procedure. Only those primers that anneal completely within an uninterrupted stretch of triplet repeat (solid arrows) will be extended successfully, while those that anneal over an AGG interruption or the unique flanking sequences (dotted arrows) will fail to extend successfully. Consequently, triplet repeats with AGG interruptions should generate PCR products which differ in size by ~30 bp if the allele is unmethylated (A). If the allele is methylated (B), pairs of PCR product peaks separated by gaps of ~27 bp should be observed, with the two peaks of each pair separated by 3 bp. If an allele contains a pure CGG repeat, an allelic ladder of PCR product peaks will be observed whether the allele is unmethylated (C) or methylated (D), with a characteristic cascading pattern of decreasing peak height with increasing product size. For simplification, the 5' tails of the uTP-F and mTP-F primers are not shown in this Figure. Numbered boxes represent CGG repeats, while black boxes in repeat sequence represent AGG interruptions. Numbers in grey background indicate the total number of triplet repeats present in the successfully amplified PCR products.

FIG. 3 is a schematic illustration of representative fluorescent electropherogram patterns after duplex methylation-specific triplet-primed PCR of the FMR1 CGG repeat from archetypal normal, premutation, and full mutation males and females.

FIG. 4 shows FAM (blue) and NED (black) fluorescent GeneScan traces of uTP-PCR and mTP-PCR products after duplex FMR1 msTP-PCR of genotype-known DNA samples of normal, premutation and full mutation males and females. The uTP and mTP PCR traces are shown separately by masking the NED and FAM channels, respectively, for ease of visualization. Red peaks are from a ROX-labeled internal size calibrator. rpts: total number of CGG repeats including AGG interruptions.

FIG. 5 shows the determination of repeat lengths and structures from electropherogram trace patterns obtained using msTP-PCR procedure. Shown are the FAM (uTP-PCR) electropherogram traces of (Ai) a 29 repeat allele with a 9+9+9 interspersion structure, (Aii) a 30 repeat allele with a 10+9+9 structure, and (Aiii) a 30 repeat allele with a 9+9+10 structure. Determining the AGG interruptions in large normal and gray zone alleles is also possible as shown in the following samples (Aiii) a 41 repeat normal allele with a 9+9+21 structure, (Aiv) a 46 repeat gray zone allele with a 9+9+13+12 structure, and (Av) a 46 repeat gray zone allele with a 9+36 structure. Also shown are the NED (mTP-PCR) electropherogram traces of (Bi) a 29 repeat allele with a 9+9+9 structure, (Bii) a 30 repeat allele with a 10+9+9 structure, and (Biii) a 41 repeat allele with a 10+9+20 structure. The numbered grey boxes indicate PCR products containing the indicated number of bisulfite-modified CGG repeats, including any intervening AGG repeats. The gaps between product peaks are caused by the presence of an AGG interruption within the CGG repeat stretch, which destabilizes any uTP-F or mTP-F primer that anneals to it, thus preventing extension products from forming. Only annealing to uninterrupted stretches of 9 or 8 CGG repeats results in robust extension and uTP-PCR and mTP-PCR amplification products, respectively.

FIG. 6 shows fluorescent GeneScan traces of FMR1 duplex msTP-PCR products from three female samples with different patterns of X-chromosome inactivation (XCI). Top row, GeneScan FAM and NED traces of sample NA20235, consistent with a random XCI state. Middle row, GeneScan traces of sample NA20236, suggestive of skewed XCI whereby a majority of the normal (31-repeat) alleles are on the inactive X chromosome. Bottom row, GeneScan traces of sample NA20239, suggestive of skewed XCI whereby a majority of the premutation (200-repeat) alleles are on the inactive X chromosome.

Figure 10:
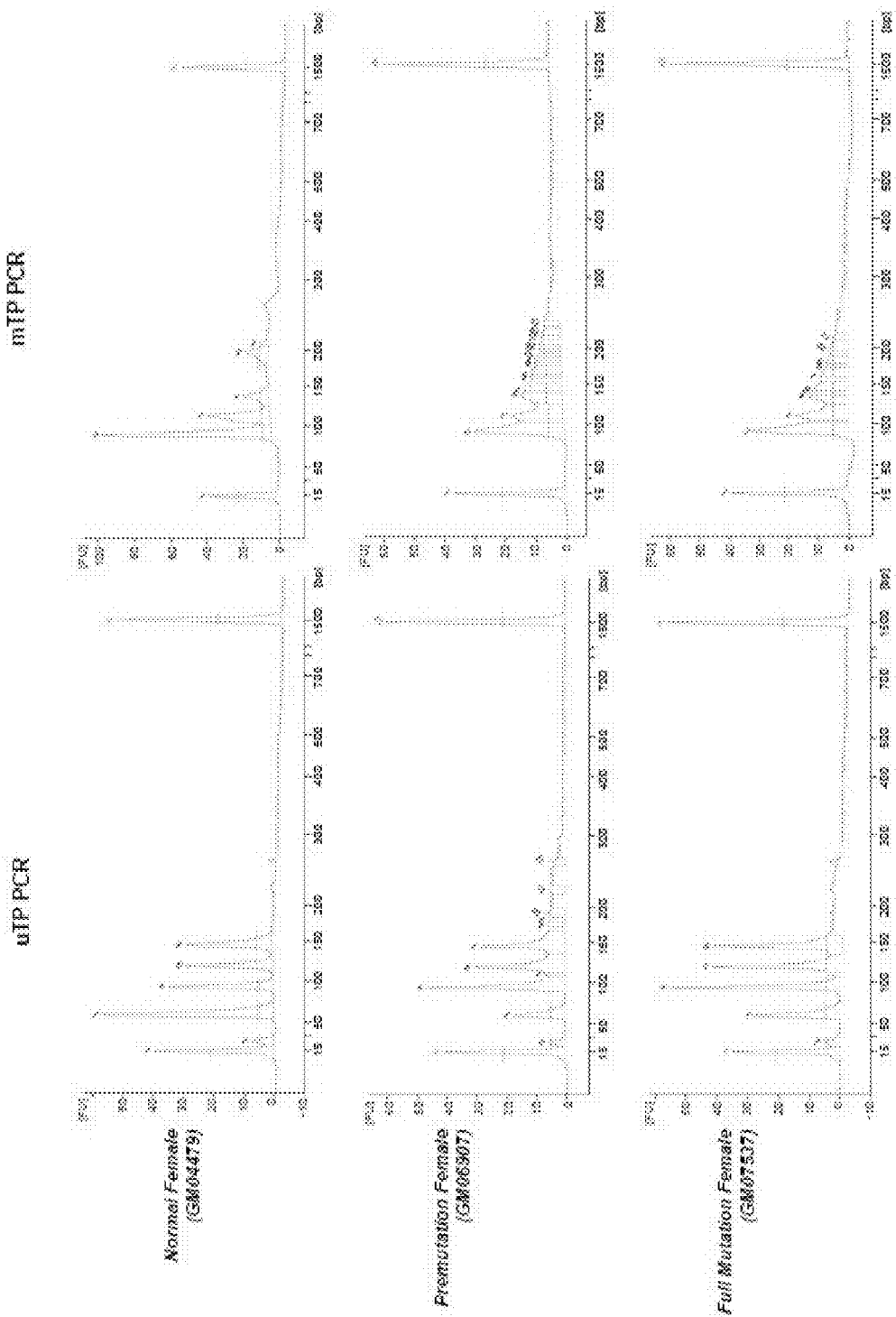

FIG. 10 shows Bioanalyzer electrophoretic profiles of uTP (left) and mTP (right) PCR products of female samples. Y-axis: fluorescence units; X-axis: size in base pairs.

Figure 11:
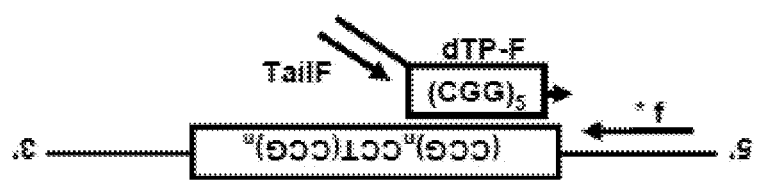

FIG. 11 shows the principle of the direct triplet-primed PCR (dTP-PCR) assay. (CGG)$_5$ is SEQ ID NO:15.

FIG. 12 is a schematic illustration of how the presence or absence of AGG interruptions affects primer annealing within the triplet repeat, and the resultant PCR product electropherogram patterns obtained using dTP-PCR procedure. Only those primers that anneal completely within an uninterrupted stretch of triplet repeat (solid arrows) will be extended successfully, while those that anneal over an AGG interruption or the unique flanking sequences (dotted arrows) will fail to extend successfully. (A) Consequently, triplet repeats with AGG interruptions should generate clusters of PCR product peaks, with the peaks in each cluster separated by 3 bp. Clusters of peaks are separated by a clear zone of ~18 bp with no peaks. (B) If an allele contains a pure CGG repeat, an allelic ladder of PCR product peaks will be observed, with a characteristic cascading pattern of decreasing peak height with increasing product size. For simplification, the 5' tails of the uTP-F and mTP-F primers are not shown in this Figure. Numbered boxes represent CGG repeats, while black boxes in repeat sequence represent AGG interruptions. Numbers in grey background indicate the total number of triplet repeats present in the successfully amplified PCR products.

Figure 13:
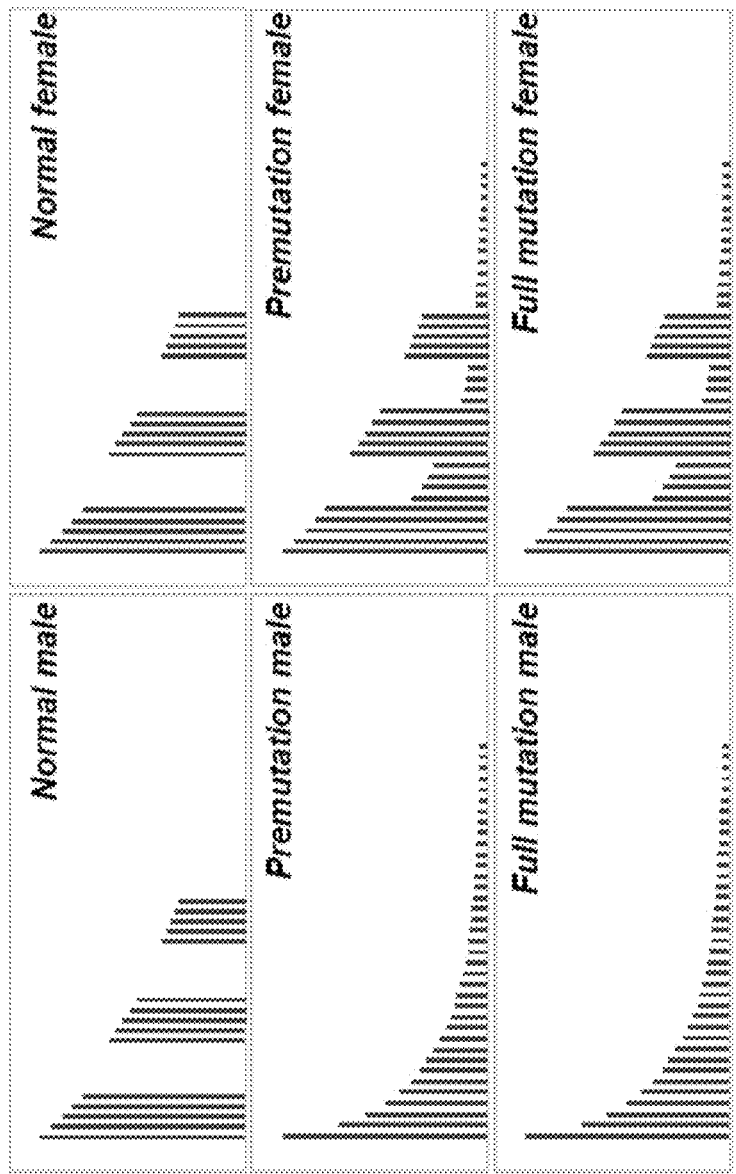

FIG. 13 is a schematic illustration of representative fluorescent electropherogram patterns after direct triplet-primed PCR of the FMR1 CGG repeat from archetypal normal, premutation, and full mutation males and females.

Figure 14:
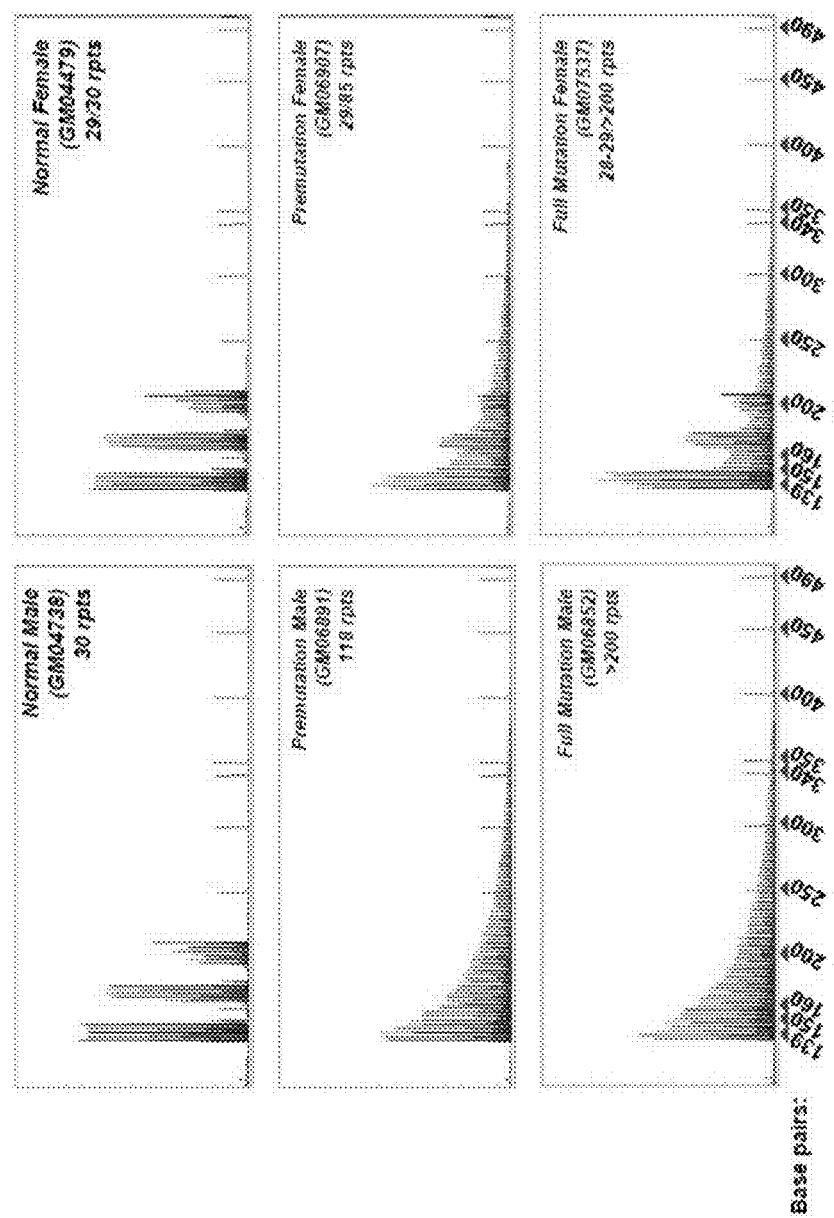

FIG. 14 shows FAM (blue) fluorescent GeneScan traces of dTP-PCR products after FMR1 direct TP-PCR of genotype-known DNA samples of normal, premutation and full mutation males and females.

Figure 15:
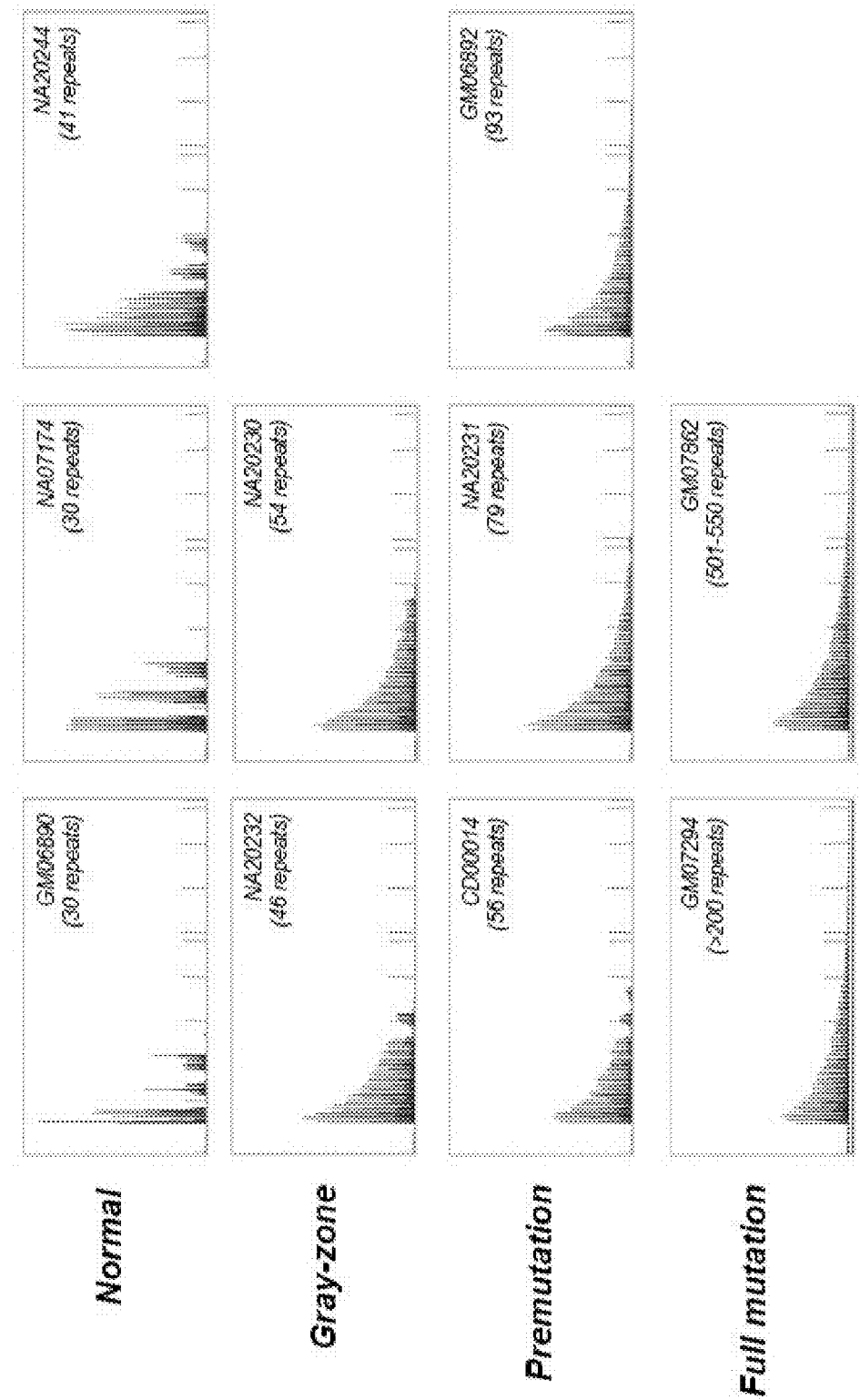

FIG. 15 shows GeneScan electropherogram traces of male samples obtained using dTP-PCR assay. Repeat sizes are in accordance to information provided by Coriell cell repository, where applicable.

Figure 16:
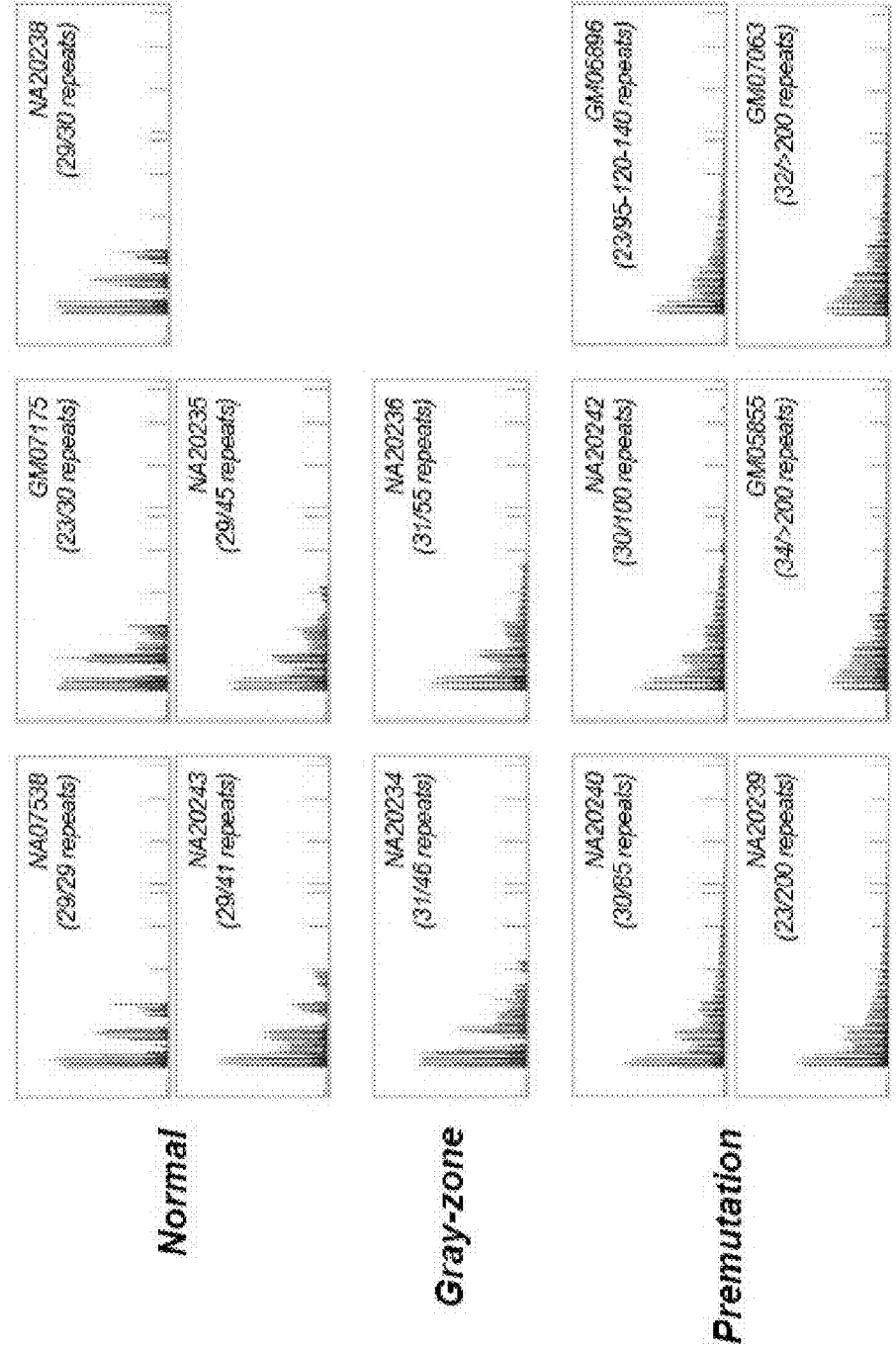

FIG. 16 shows GeneScan electropherogram traces of female samples obtained using dTP-PCR assay. Repeat sizes are in accordance to information provided by Coriell cell repository, where applicable.

Figure 17:
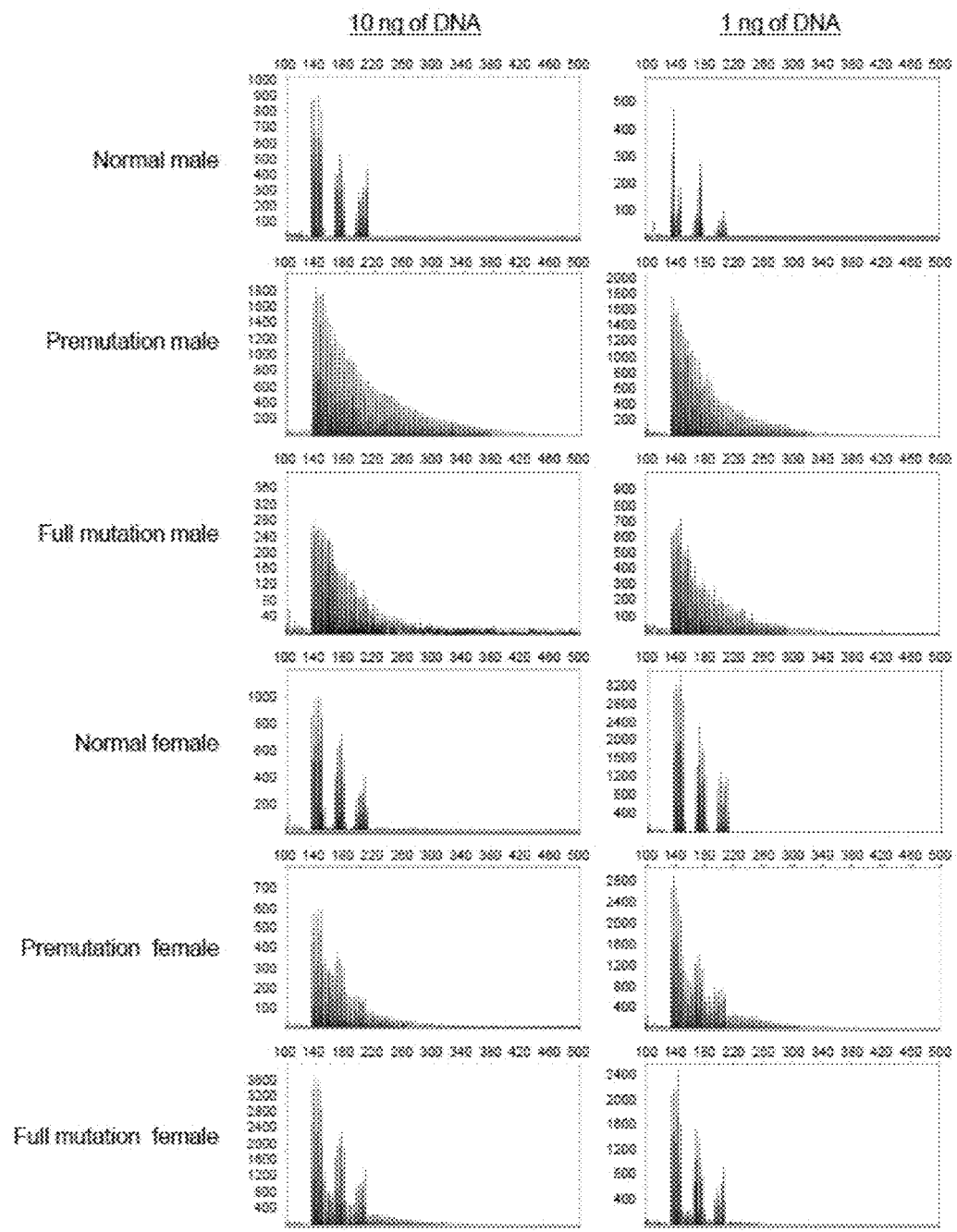

FIG. 17 shows GeneScan electropherogram traces of dTP PCR amplification products from 10 ng (left) and 1 ng (right) of genomic DNA.

Figure 18:
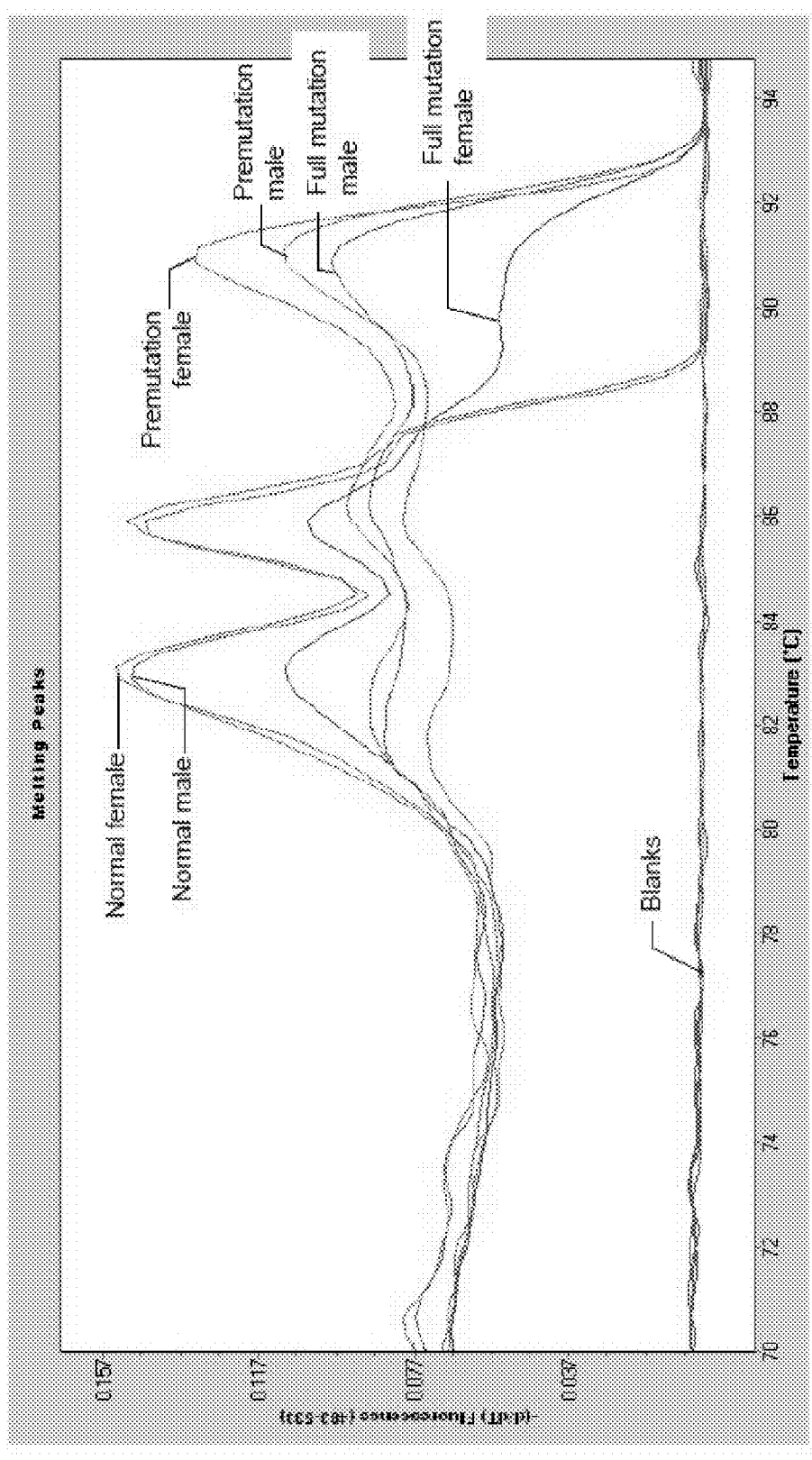

FIG. 18 shows melting peak patterns from normal, premutation and full mutation males and females obtained using dTP-PCR assay.

Figure 19:
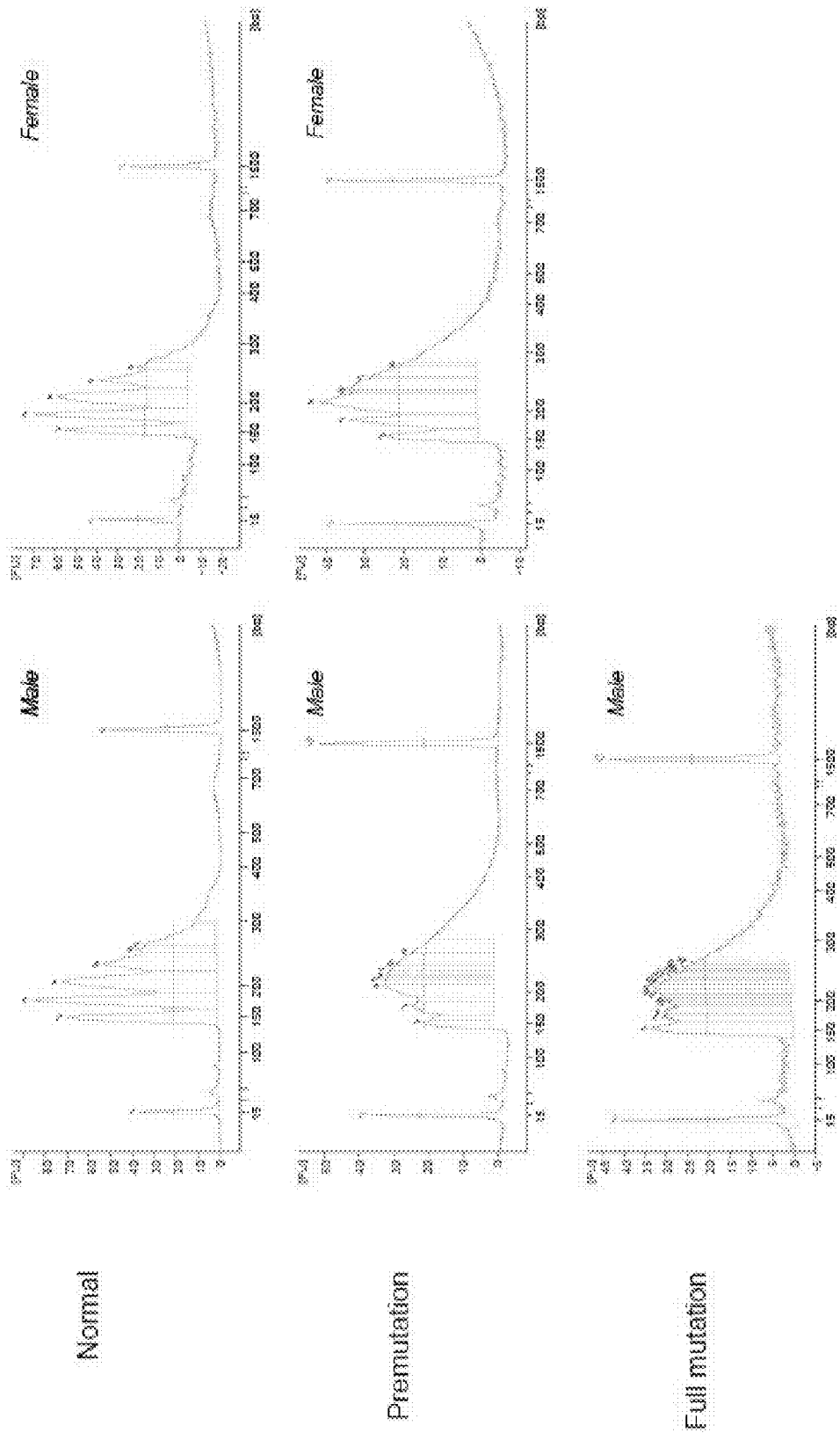

FIG. 19 shows Bioanalyzer electrophoretic profiles of normal, premutation and full mutation samples obtained using dTP-PCR assay.

Figure 20:
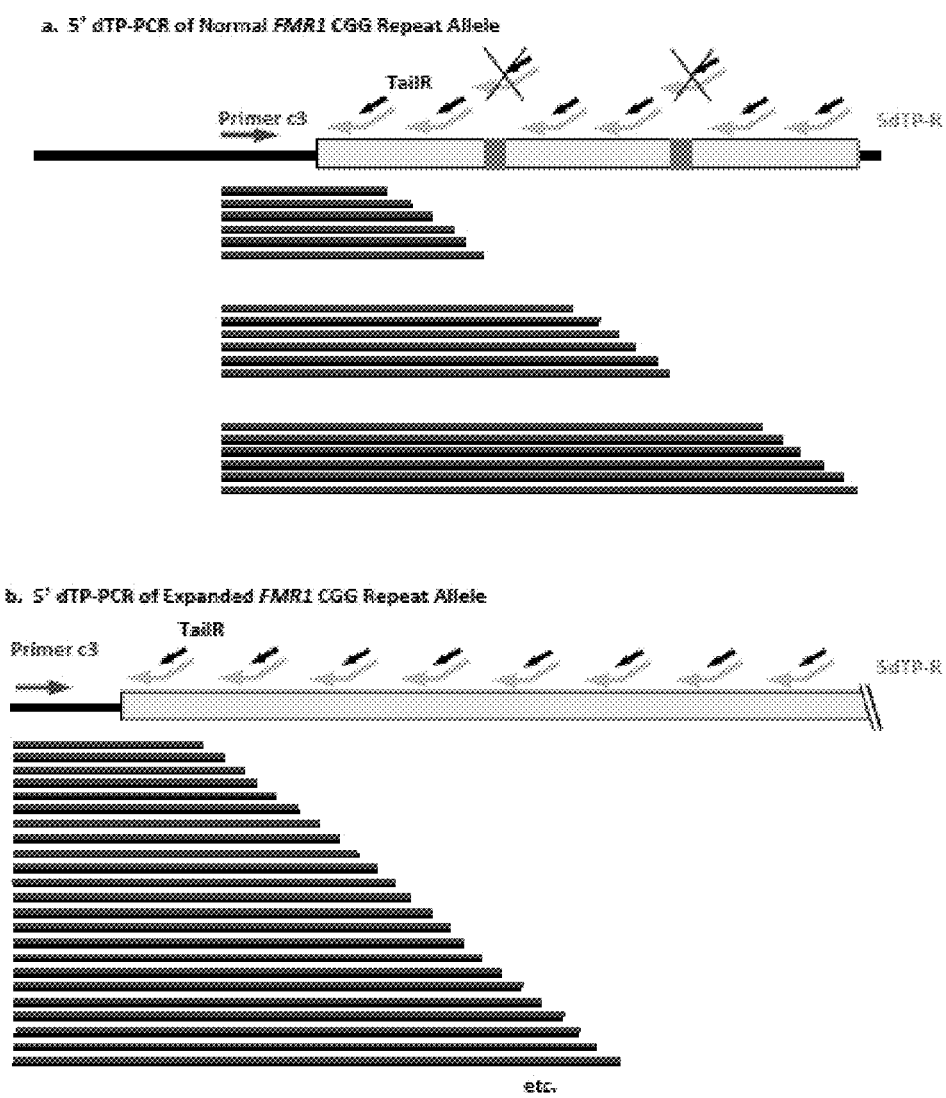

FIG. 20 shows the design of primers against the CGG repeat region of the FMR1 allele. The dTP-R primer is "tailed" with a non-specific sequence in its 5' half, while its 3' half consists of 5 CGG triplets, which enable annealing within the triplet repeats. The TailR primer anneals only to pre-amplified DNA containing the tail sequence. The forward primer c is labeled with Fam. This schematic illustrates how the a) presence or b) absence of AGG interruptions affects primer annealing within the triplet repeat, and the resultant PCR products following amplification. Only those primers that anneal completely within an uninterrupted stretch of triplet repeat, as shown in b), will be extended successfully, while those that anneal over an AGG interruption or the unique flanking sequences will fail to extend successfully, as shown in a).

Figure 21:
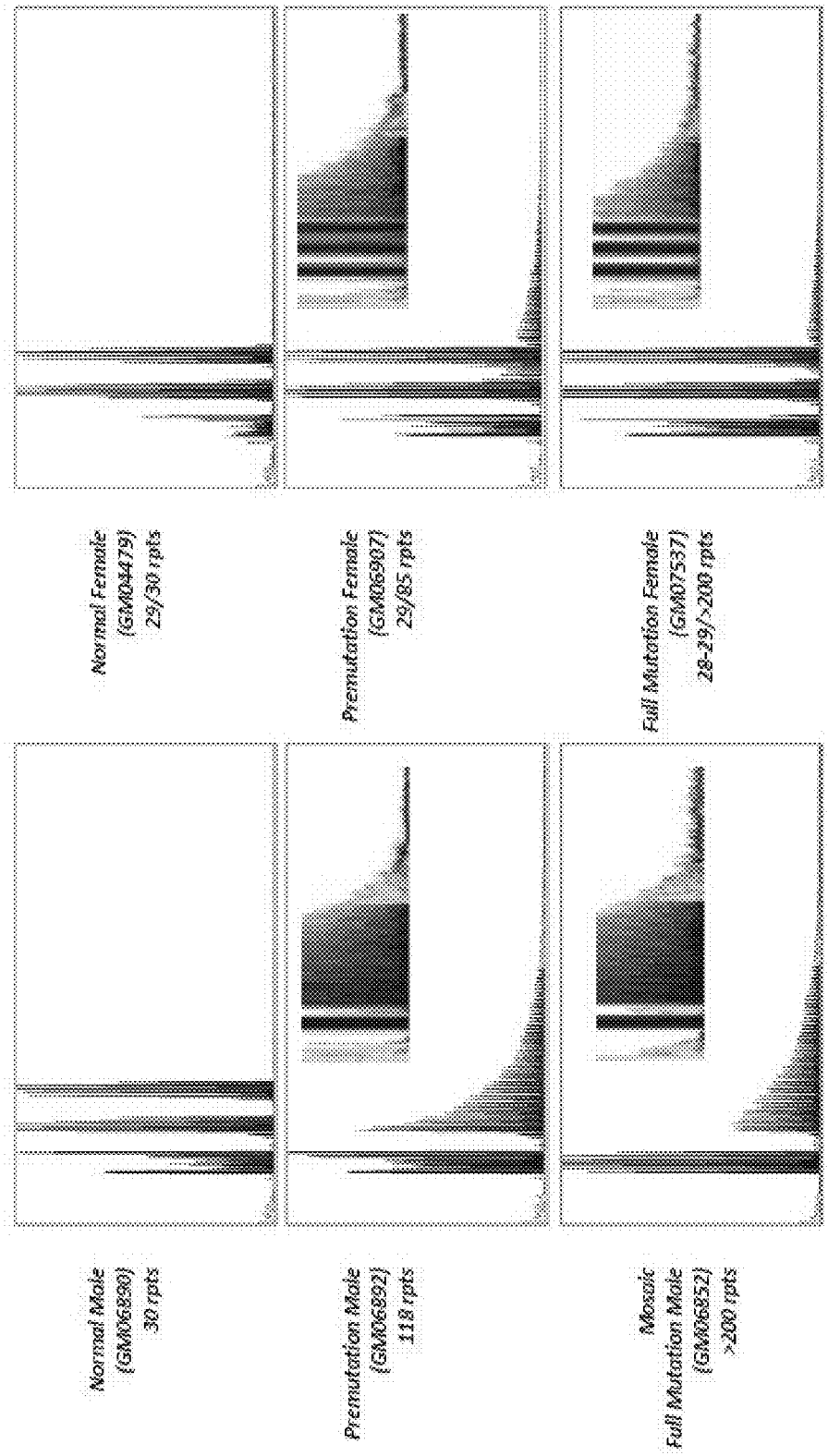

FIG. 21 shows FAM (blue) fluorescent GeneScan traces of 5'dTP-PCR products after FMR1 5' dTP-PCR of genotype-known DNA samples of normal, premutation and full mutation males and females. The enlarged views of the peak ladders of premutation and full mutation samples are shown in the inset. rpts: total number of CGG repeats including AGG interruptions.

Figure 22:
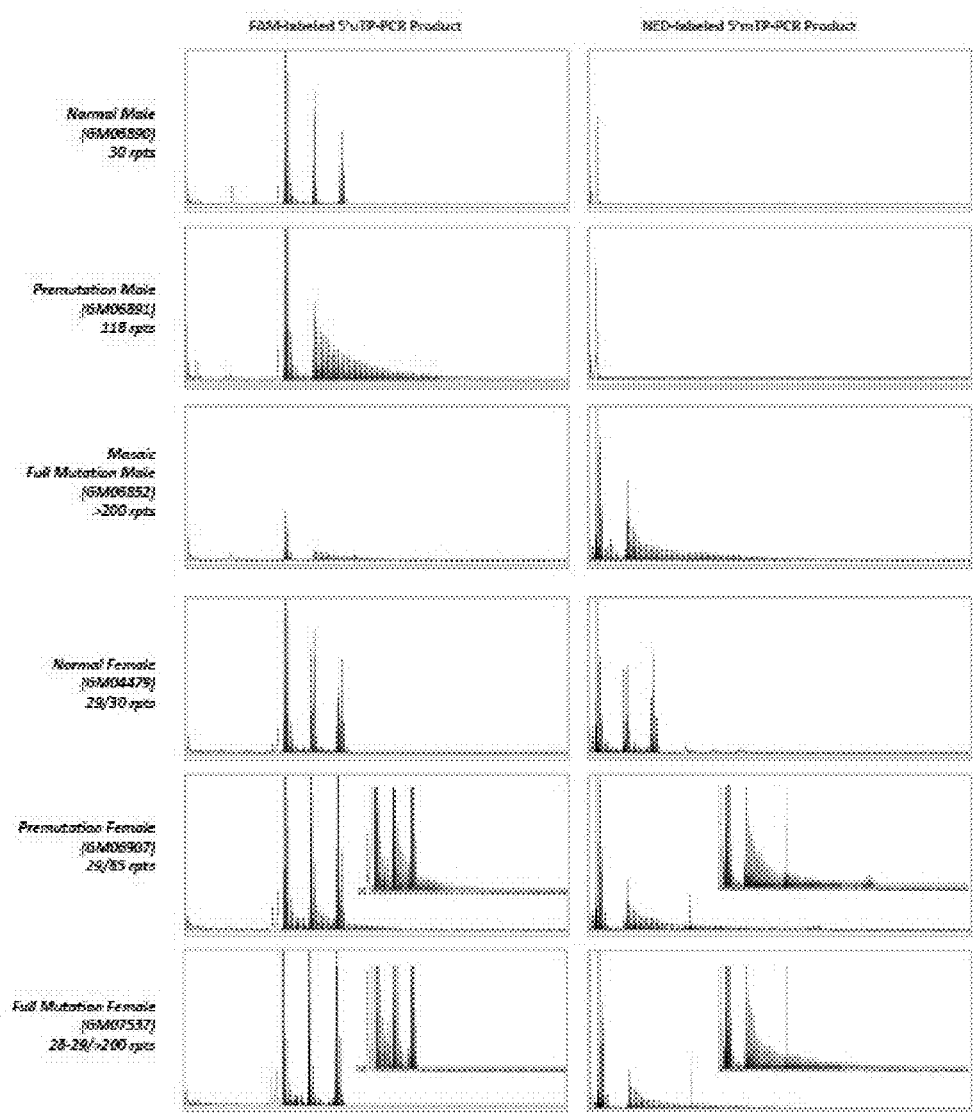

FIG. 22 shows FAM (blue) and NED (black) fluorescent GeneScan traces of 5'uTP-PCR and 5'mTP-PCR products after duplex FMR1 5' msTP-PCR of genotype-known DNA samples of normal, premutation and full mutation males and females. The uTP and mTP PCR traces are shown separately by masking the NED and FAM channels, respectively, for ease of visualization. rpts: total number of CGG repeats including AGG interruptions.

Figure 23:
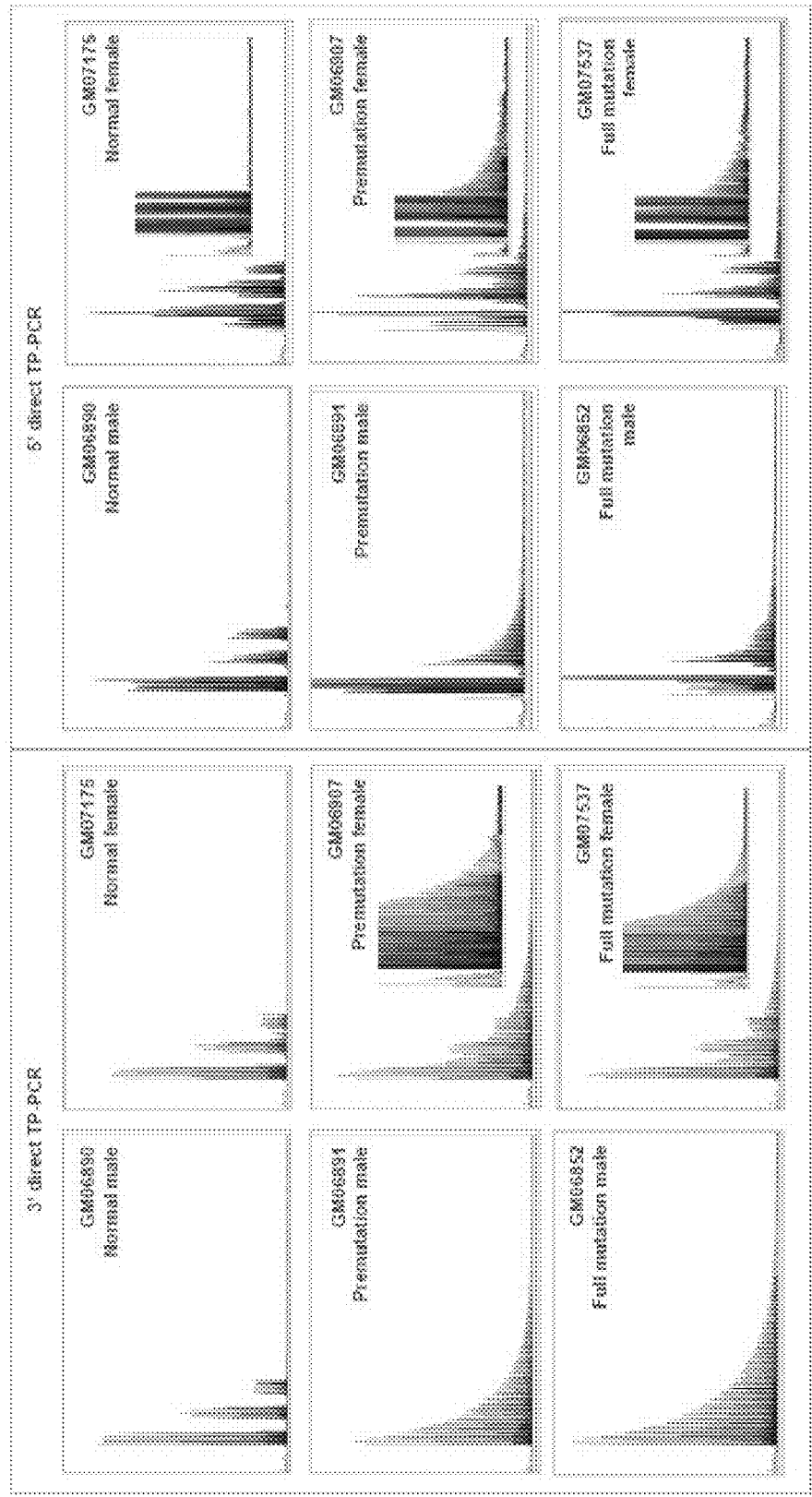
Figure 24A:
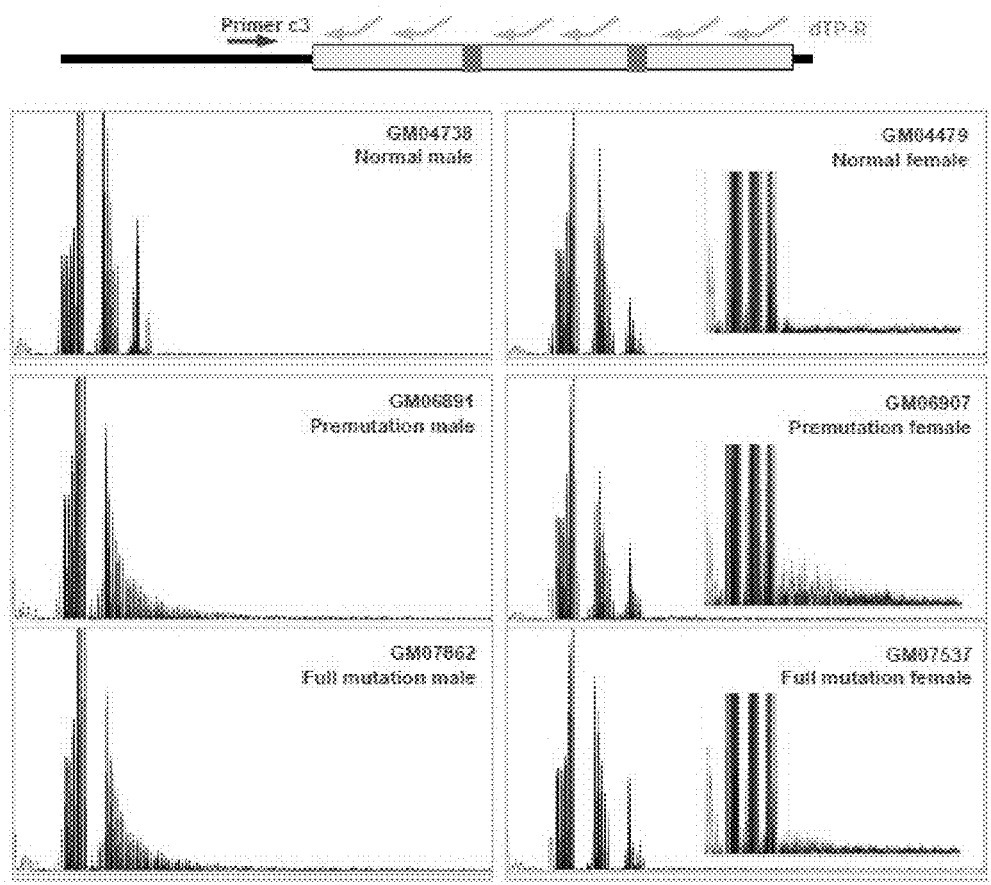
Figure 24B:
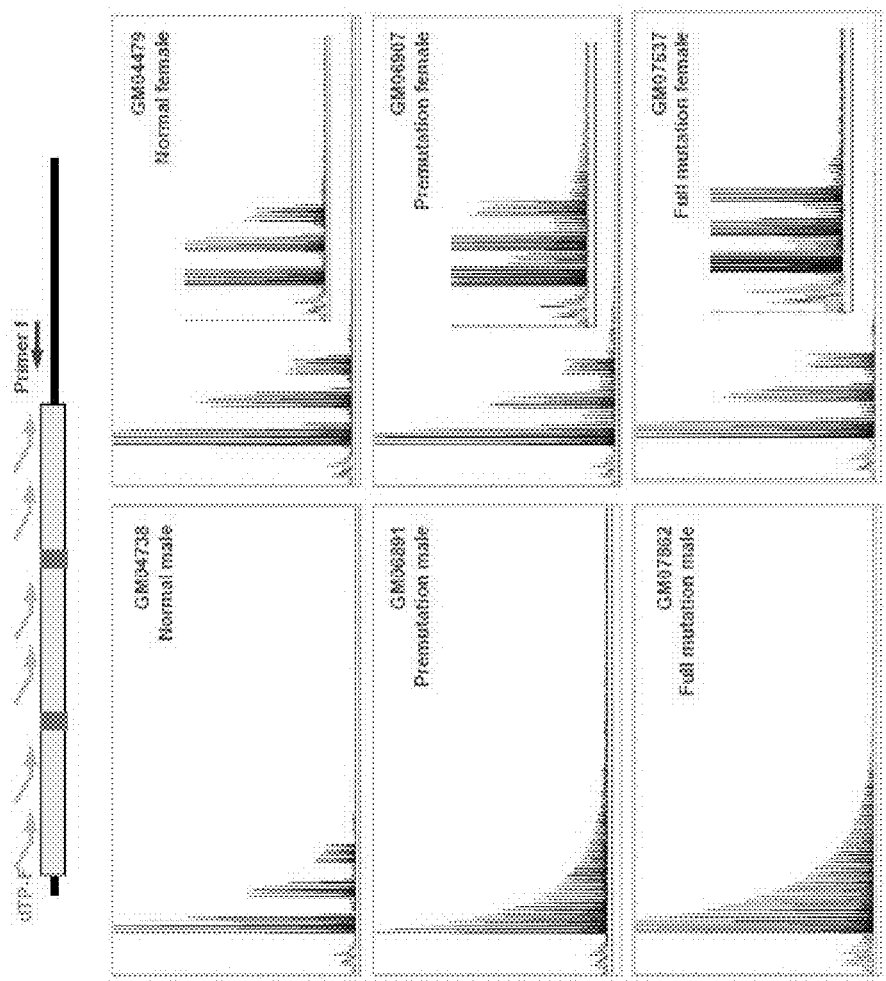
Figure 24C:
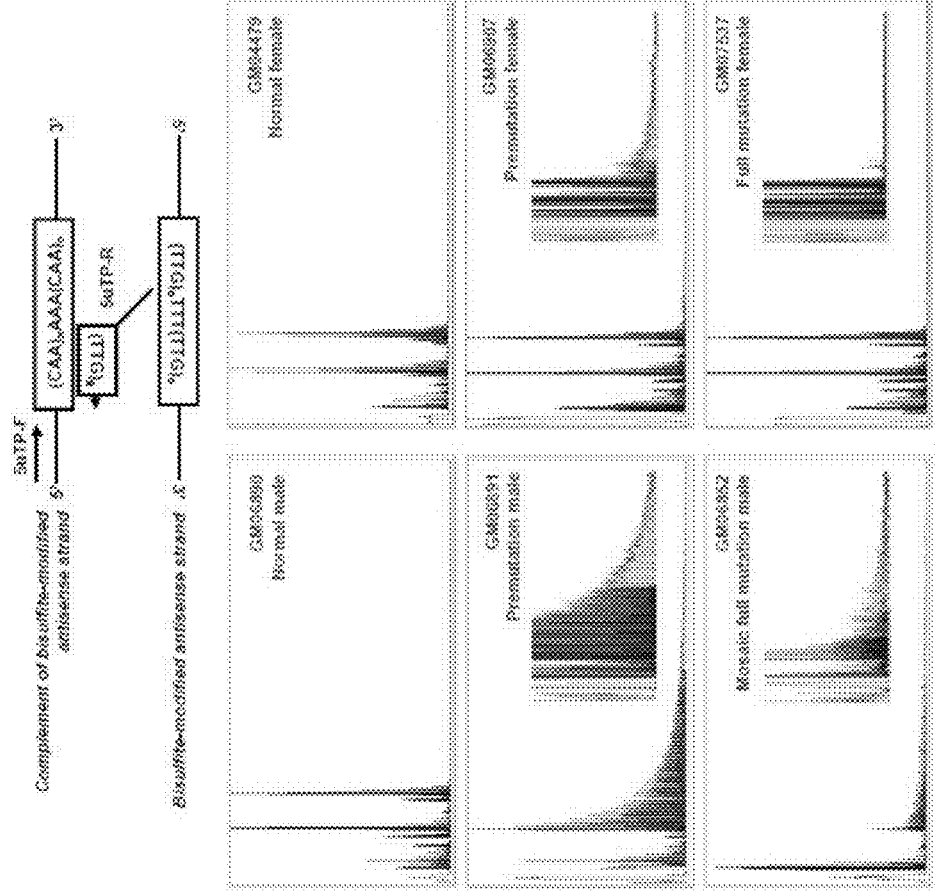
Figure 24D:
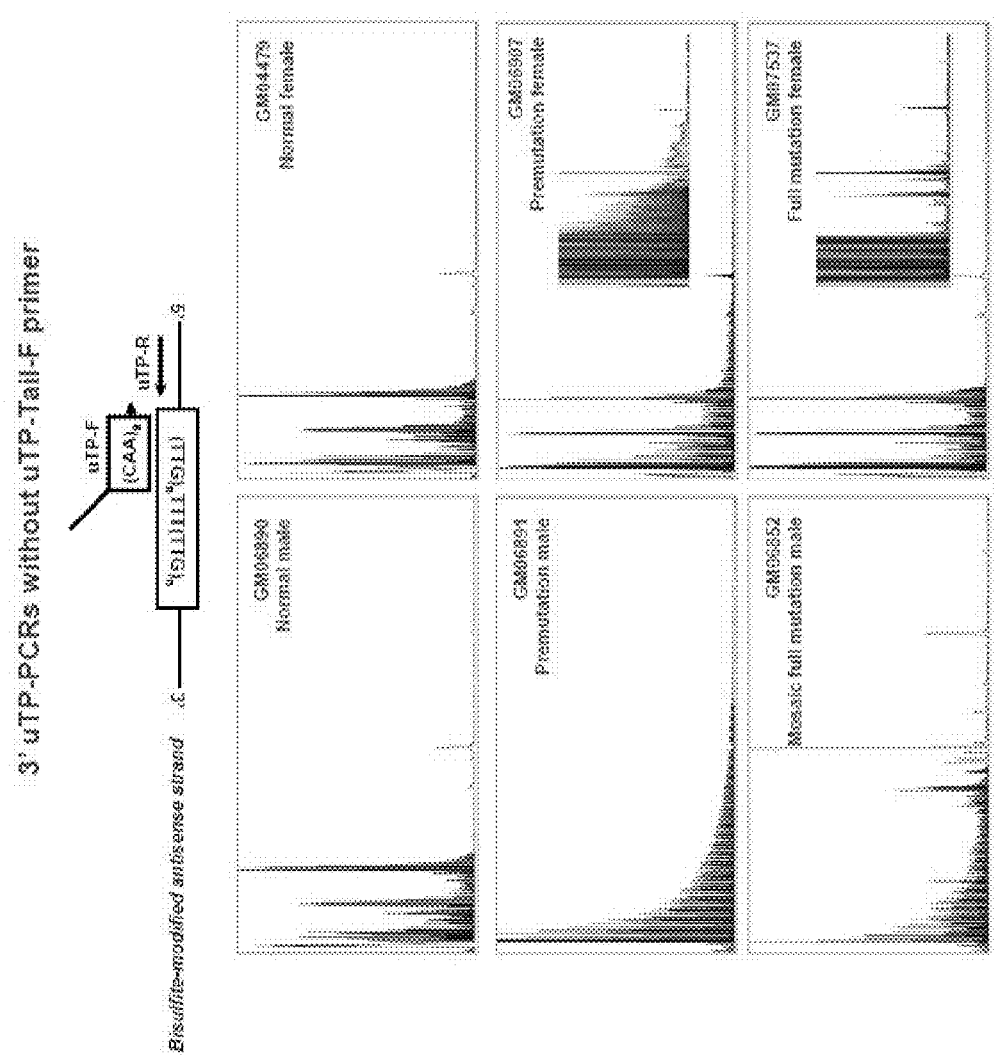
Figure 25A:
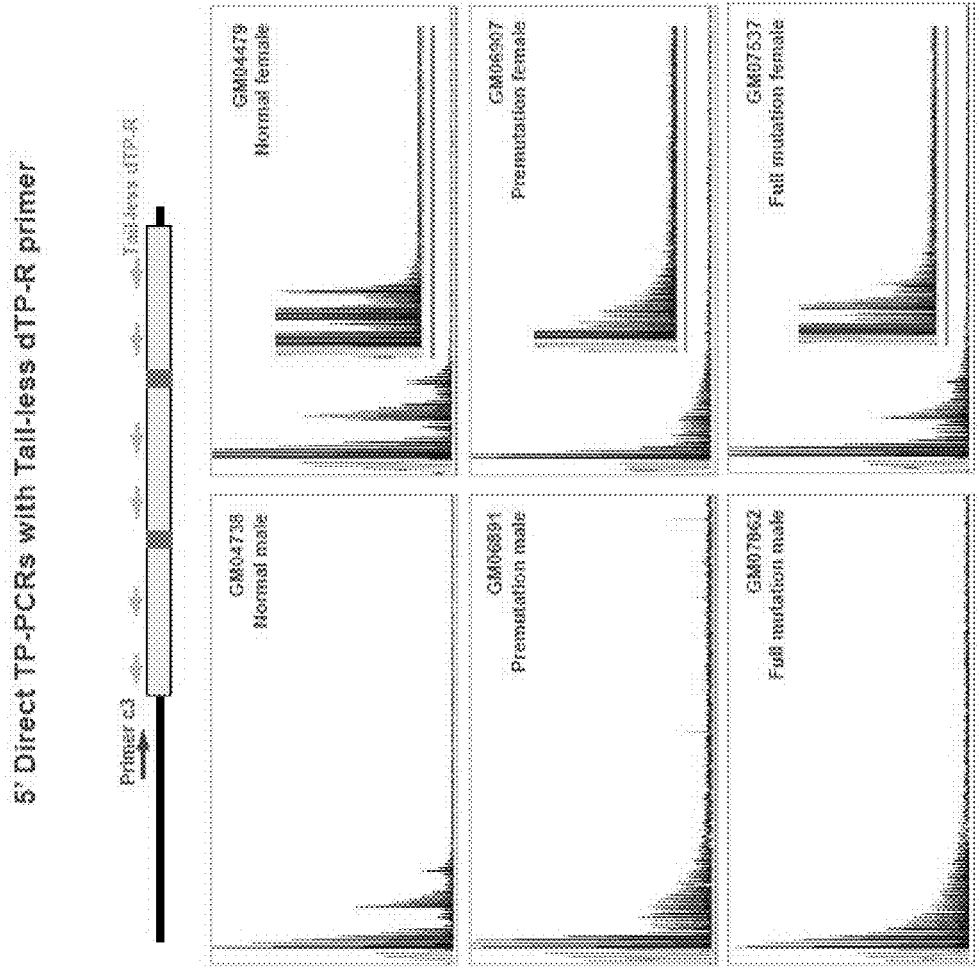
Figure 25B:
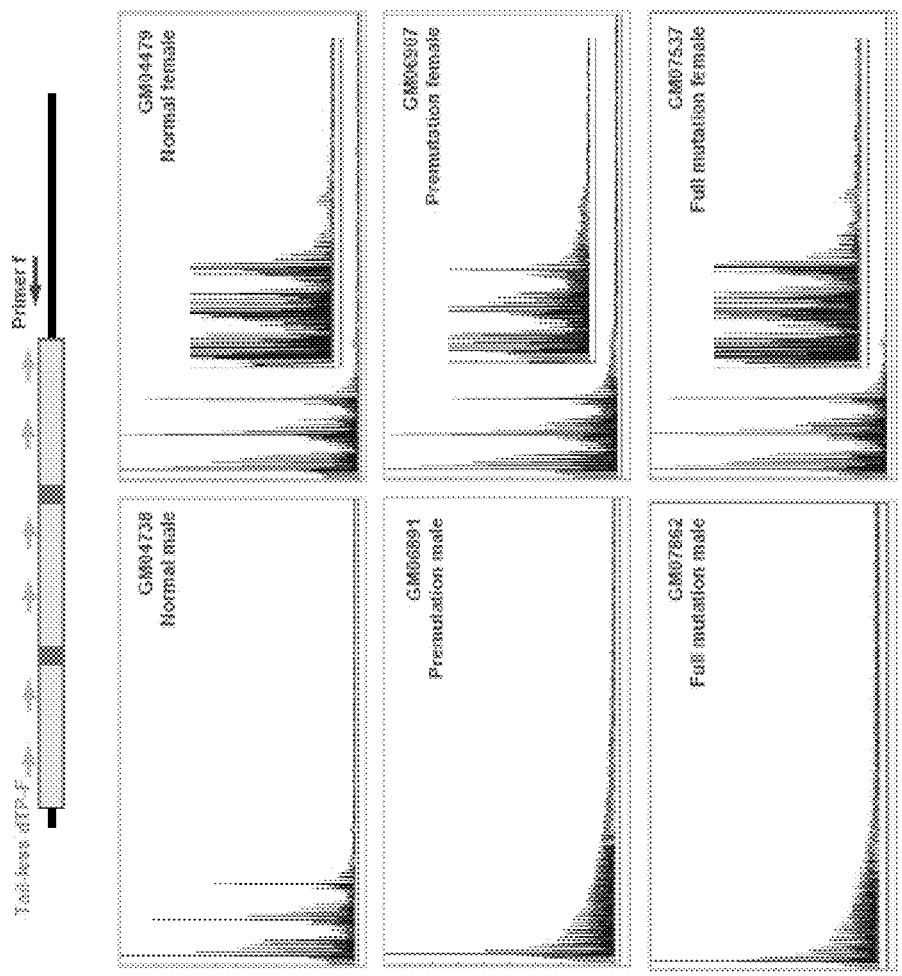
Figure 25C:
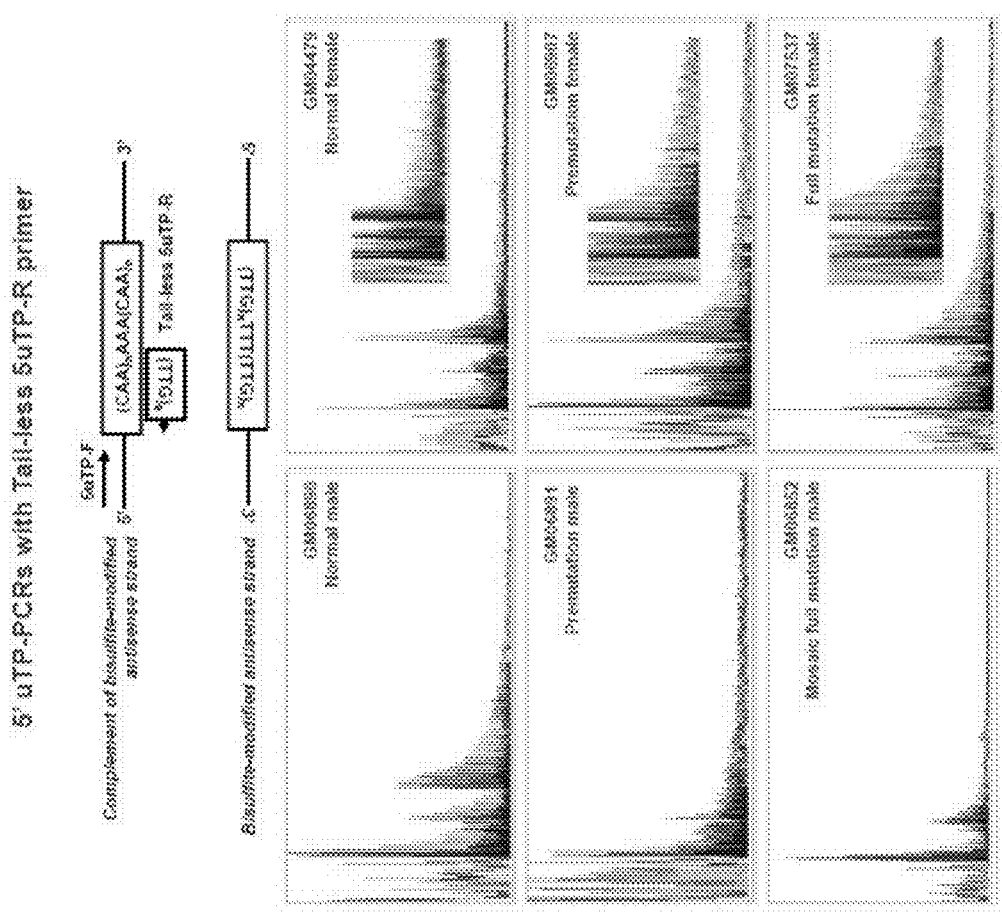
Figure 25D:
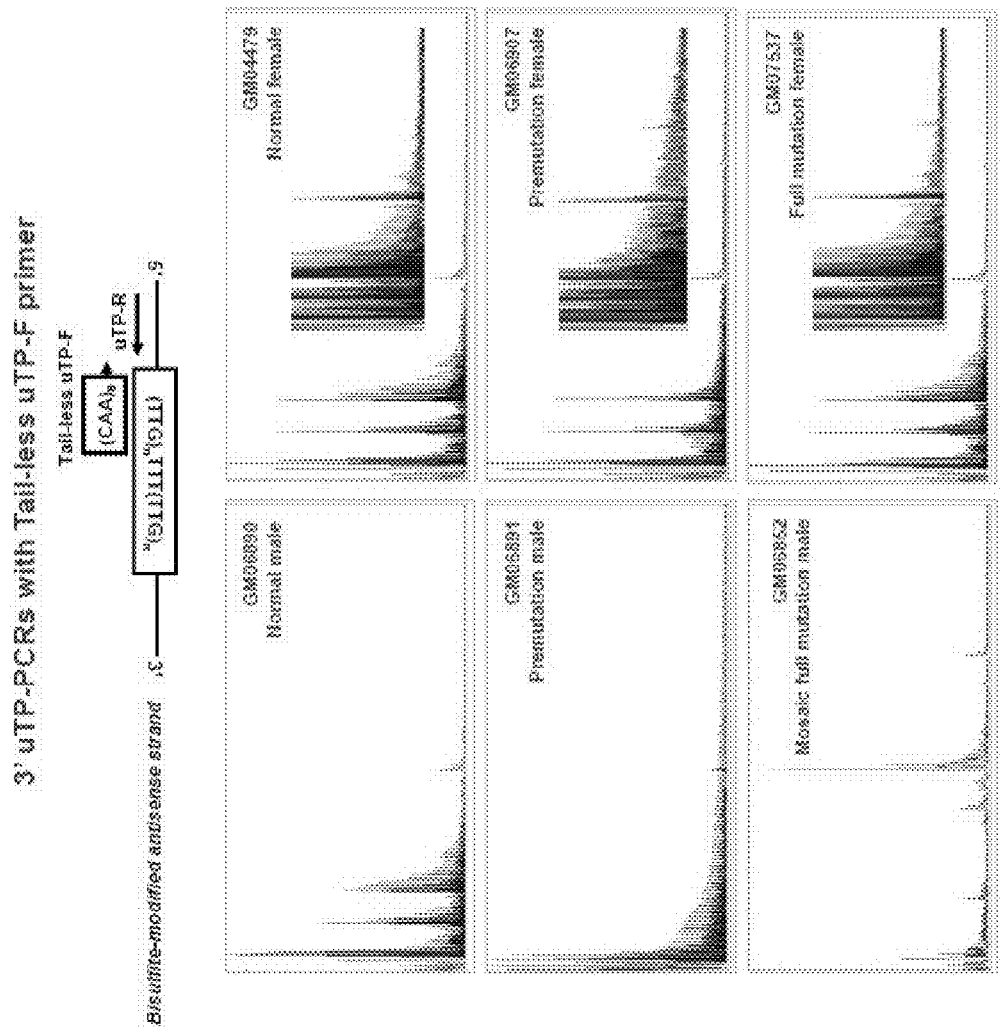

FIG. 23 shows FAM (blue) and NED (black) fluorescent GeneScan traces of 5'uTP-PCR and 5'mTP-PCR products after duplex FMR1 5' msTP-PCR of genotype-known DNA samples of normal, premutation and full mutation males and females. The uTP and mTP PCR traces are shown separately by masking the NED and FAM channels, respectively, for ease of visualization. rpts: total number of CGG repeats including AGG interruptions.

FIGS. 24a-d show 5' and 3' direct and methylation-specific uTP-PCRs performed without the Tail primers. (TTG)$_9$ are residues 22 to 48 of SEQ ID NO: 25, and (CAA)$_9$ are residues 22 to 48 of SEQ ID NO: 1.

FIGS. 25a-d show 5' and 3' direct and methylation-specific uTP-PCRs performed with repeat-annealing primers without tail sequences. (TTG)$_9$ are residues 22 to 48 of SEQ ID NO: 25, and (CAA)$_9$ are residues 22 to 48 of SEQ ID NO: 1.

Figure 26:
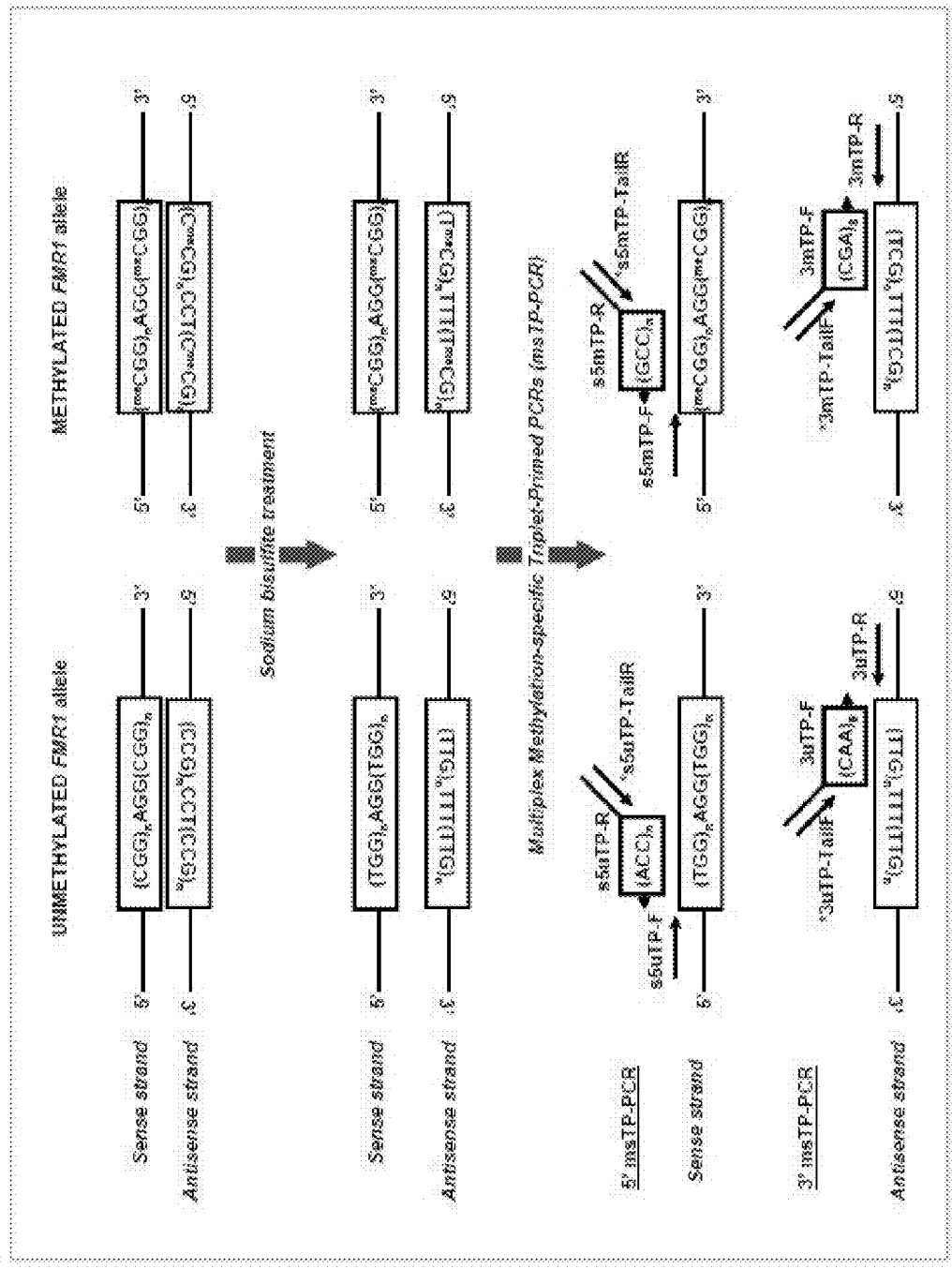

FIG. 26 is a schematic illustration of multiplexing both 5' and 3' duplex msTP-PCRs in one single reaction. (CAA)$_9$ are residues 22 to 48 of SEQ ID NO: 1, and (CGA)$_8$ are residues 22 to 45 of SEQ ID NO: 4.

TABLES

Table 1. Primers used in amplification of sodium bisulfite-treated methylated and unmethylated FMR1 alleles.

Table 2. Male genomic DNA samples from Coriell Cell Repository lines used for assay optimization and validation.

Table 3. Female genomic DNA samples from Coriell Cell Repository lines used for assay optimization and validation.

Table 4. Primers used in amplification of sodium bisulfite-treated methylated and unmethylated FMR1 alleles for screening using DNA melt curve analysis.

Table 5. Primers used in amplification of FMR1 alleles.

Table 6. Male genomic DNA samples from Coriell Cell Repository fines used for assay optimization and validation.

Table 7. Female genomic DNA samples from Coriell Cell Repository lines used for assay optimization and validation.

Table 8. Primers for 5' direct TP-PCR.

Table 9. Primers for 5' duplex msTP-PCR.

SEQUENCES

Sequences

SEQ ID NO:1: First Forward Primer for amplification of bisulphite treated DNA having a target sequence corresponding to unmethylated DNA located within the trinucleotide repeat sequence.

SEQ ID NO:2: Reverse Primer for amplification of bisulphite treated DNA having a target sequence corresponding to unmethylated DNA located 3' of the trinucleotide repeat sequence.

SEQ ID NO:3: Second Forward Primer having a sequence which corresponds to the 5' sequence of SEQ ID NO:1.

SEQ ID NO:4: First Forward Primer for amplification of bisulphite treated DNA having a target sequence corresponding to methylated DNA located with the trinucleotide repeat sequence.

SEQ ID NO:5: Reverse Primer for amplification of bisulphite treated DNA having a target sequence corresponding to methylated DNA located 3' of the trinucleotide repeat sequence.

SEQ ID NO:6: Second Forward Primer having a sequence which corresponds to the 5' sequence of SEQ ID NO:4.

SEQ ID NO:7: Reverse Primer for amplification of untreated DNA having a target sequence located 3' of the trinucleotide repeat sequence.

SEQ ID NO:8: First Forward Primer for amplification of untreated DNA having a target sequence located within the trinucleotide repeat sequence SEQ ID NO:9: Second Forward Primer having a sequence which corresponds to the 5' sequence of SEQ ID NO:8.

SEQ ID NO:10: Reverse Primer for amplification of untreated DNA having a target sequence located 3' of the trinucleotide repeat sequence.

SEQ ID NO:11: First Forward Primer for amplification of untreated DNA having a target sequence located within the trinucleotide repeat sequence.

SEQ ID NO:12: Second Forward Primer having a sequence which corresponds to the 5' sequence of SEQ ID NO:8.

SEQ ID NO:13-15: A portion of a first forward primer comprising a nucleic acid sequence complementary to a sequence located within the trinucleotide repeat sequence which may be joined with any one of the sequences of SEQ ID NOS:16-19 to produce a forward primer in accordance with the disclosure described herein.

SEQ ID NO:16-18: A portion of a forward primer that may be joined with any of SEQ ID NOS:13-15 to form a forward primer in accordance with the disclosure described herein.

SEQ ID NO:20: Reverse Primer for amplification of bisulphite treated DNA having a target sequence corresponding to methylated DNA located 3' of the trinucleotide repeat sequence.

SEQ ID NO:21: Forward Primer for amplification of untreated DNA having a target sequence located 5' of the trinucleotide repeat sequence.

SEQ ID NO:22: Reverse Primer for amplification of untreated DNA having a target sequence located within the trinucleotide repeat sequence SEQ ID NO:23: Second Reverse Primer having a sequence which corresponds to the 5' sequence of SEQ ID NO:21.

SEQ ID NO:24: Forward Primer for amplification of bisulphite treated DNA having a target sequence located 5' of the trinucleotide repeat sequence.

SEQ ID NO:25: First Reverse Primer for amplification of bisulphite treated DNA having a target sequence corresponding to unmethylated DNA located within the trinucleotide repeat sequence SEQ ID NO:26: Forward Primer, for amplification of bisulphite treated DNA having a target sequence located 5' of the trinucleotide repeat sequence.

SEQ ID NO:27: First Reverse Primer for amplification of bisulphite treated DNA having a target sequence corresponding to methylated DNA located within the trinucleotide repeat sequence Definitions The following words and terms used herein shall have the meaning indicated:

The term "trinucleotide repeat sequence disorder" refers to a genetic disorder caused by an increase in the number of trinucleotide repeats in certain genes exceeding a normal, stable, threshold, which differs per gene. This term is intended to include all disorders of this nature, whether referred to as trinucleotide repeat disorders, trinucleotide repeat expansion disorders or triplet repeat expansion disorders.

As used herein the term "region 5' of the repeat region" refers to a nucleotide sequence 5' of the trinucleotide repeat sequence. This region may be located immediately adjacent to the trinucleotide repeat region or may be located distal from the trinucleotide repeat region.

The term "under amplification conditions" refers' to an amplification reaction, for example an enzyme-mediated reaction used to amplify a specific target nucleotide sequence in a template nucleotide sequence. By amplifying the target nucleotide sequence in the template, the reaction produces many more copies of the target nucleotide sequence to produce an amplicon, amplified product or amplification product. This is useful when a biological sample contains only small amounts of a template nucleotide sequence. One example of an amplification reaction is a "polymerase chain reaction (PCR)". PCR is carried out with the aid of thermal cycler in a mixture containing a polymerase enzyme, a set of primers, for example a set of forward and reverse primers and any additional primers that may be required and four deoxynucleotide triphosphates (dNTPs).

As used herein, the term "amplicon", "amplified product or "amplification product" refers to a product of an amplification reaction. An example of an amplicon is a nucleotide sequence produced as a result of PCR, real-time PCR, RT-PCR, competitive RT-PCR, ligase chain reaction (LCR), gap LCR, strand displacement amplification (SDA), nucleic acid sequence based amplification (NASBA), transcription-mediated amplification (TMA), or the like. The term "complementary", as used herein, refers to a nucleic acid sequence that is complementary to a specified nucleic acid sequence. It is well known in the art that each nucleotide of the primer or probe can form a hydrogen bond with its counterpart target nucleotide. For example, the complementarity of primer or probe with the target sequence is assessed by the degree of A:T and C:G base pairing, such that an adenine (A) nucleotide pairs with a thymine (T), and such that a guanine (G) nucleotide pairs with a cytosine (C), or vice versa. In the RNA form, T may be replaced by U (uracil). In one example, inosine may be included in a sequence considered complementary to another sequence, in view of its ability to indiscriminately pair with adenine, thymine, or cytosine.

The term "primer" is used herein to mean any single-stranded oligonucleotide sequence capable of being used as a primer in, for example, PCR technology. Thus, a "primer" according to the disclosure refers to a single-stranded oligonucleotide sequence that is capable of acting as a point of initiation for synthesis of a primer extension product that is substantially identical to the nucleic acid strand to be copied (for a forward primer) or substantially the reverse complement of the nucleic acid strand to be copied (for a reverse primer). A primer may be suitable for use in, for example, PCR technology. By single-stranded includes, for example, hairpin structures formed by single-stranded nucleotide sequences.

The design of a primer, for example its length and specific sequence, depends on the nature of the target nucleotide sequence and on the conditions at which the primer is used, for example, temperature and ionic strength.

The primers may consist of the nucleotide sequences described herein, or may be 10, 15, 20, 25, 30, 35, 40, 45, 50, 75, 100 or more nucleotides which comprise or fall within the sequences described herein, provided they are suitable for specifically binding a target sequence, under stringent conditions. In one embodiment, the primer sequence is less than 35 nucleotides in length, for example the primer sequence is less than 34, 33, 32, 31, 30, 29, 28, 27, 26, 25, 24, 23, 22 or 21 nucleotides in length.

Slight modifications of the primers or probes, in length or in sequence, can be carried out to maintain the specificity and sensitivity required under the given circumstances. In one embodiment of the present disclosure, probes and/or primers described herein may be extended in length by 1, 2, 3, 4 or 5 nucleotides or reduced in length by 1, 2, 3, 4 or 5 nucleotides, for example, in either direction.

Primer sequences can be synthesised using any methods well known in the art.

As used herein, the term "multiplexed" refers to a multiplex PCR amplification reaction. A multiplex PCR reaction permits the detection of more than one template in a mixture of templates by the addition of more than one set of oligonucleotide primers to the amplification reaction.

As used herein, the term "target sequence" refers to a region of a nucleotide sequence to which a primer specifically hybridises, that is, a region with which the primer has partial (i.e. with some degree of mismatch) or total identity; although the reverse primer is the reverse complement (or, as above, has some degree of mismatch) of the sequence it recognises.

In one aspect, the term "comprising" in relation to the primer sequences described herein may be considered to include sequences that are extended in length by 1, 2, 3, 4 or 5 nucleotides, for example, in either direction.

As used herein, the term "isolated" means that a nucleotide sequence, for example a gene, primer, or oligonucleotide or other sequence is substantially or essentially free from the remainder of the human genome and associated cellular or other impurities. This does not mean that the nucleotide sequence has to have been extracted from the human genome; rather, the sequence could be a synthetic or cloned sequence.

As used herein, the term "nucleotide sequence" means any single or double-stranded RNA or DNA molecule, such as mRNA, cDNA, and genomic DNA.

As used herein, the term "trinucleotide repeat sequence" refers to a region of a gene that includes repeats of a trinucleotide sequence that vary in number from individual allele to individual allele, and which can range in number from 2 to >200 or more.

As used herein, "hybridizes" or "anneals" means that the primer or oligonucleotide forms a noncovalent interaction with the target nucleic acid molecule under standard stringency conditions. The primer or oligonucleotide may further contain non-hybridizing nucleotides that do not interfere with forming the noncovalent interaction, e.g., a 5' unique tail sequence or a restriction enzyme recognition site to facilitate cloning.

By "unique tail sequence" is meant a sequence that does not hybridise under stringent conditions to any region in a nucleotide sequence to be screened for the presence of a trinucleotide repeat sequence. All Tail primers were designed to fit the following criteria:
  Less than 65% complementarity to human genomic sequences, determined by NCBI Blastn search on the human genomic and transcript database.
  The tail sequence does not contain a sequence of more than 4 nucleotides that is complementary to the other primers in the same reaction.

As used herein, any "hybridisation" is performed under stringent conditions. The term "stringent conditions" means any hybridisation conditions which allow the primers to bind specifically to a target nucleotide sequence. For example, hybridisation of a primer to a target nucleotide sequence under "stringent" hybridisation conditions, is specific hybridisation, and includes conditions such as 3×SSC, 0.1% SDS, at 50° C. The skilled person knows how to vary the parameters of temperature, probe length and salt concentration such that specific hybridisation can be achieved. Hybridisation and wash conditions are well known and exemplified in, for example, Sambrook, et al., Molecular Cloning: A Laboratory Manual, Second Edition, Cold Spring Harbor, N.Y., (1989), particularly Chapter 11 therein.

"Specific binding" or "specific hybridisation" of a primer to a target sequence means that the primer forms a duplex (double-stranded nucleotide sequence) with part of the target sequence region or with the entire target sequence as required, under the experimental conditions used, for example under stringent hybridisation conditions, and that under those conditions the primer does not form a duplex with other regions of the nucleotide sequence present in the sample to be analysed.

The nucleotide sequences presented herein are contiguous, 5' to 3' nucleotide sequences, unless otherwise described.

The term "dNTPs" refers to deoxyribonucleotide triphosphates, for example the four naturally occuring deoxyribonucleotides: dATP, dCTP, dGTP and dTTP, which are polymerized by DNA polymerase to produce DNA By "biological sample" is meant a sample of tissue or cells from a patient that has been obtained from, removed or isolated from the patient.

The term "obtained or derived from" as used herein is meant to be used inclusively. That is, it is intended to encompass any nucleotide sequence directly isolated from a biological sample or any nucleotide sequence derived from the sample.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DESCRIPTION

Exemplary, non-limiting embodiments of a method for screening for an allelic expansion in a sample of a nucleic acid, will now be disclosed.

In one embodiment of the present disclosure there is provided a method for screening for a trinucleotide repeat sequence in a biological sample, wherein said method comprises the step of contacting a nucleic acid sequence obtained or derived, from the biological sample under amplification conditions with:
i) a reverse primer, wherein said reverse primer has a target sequence in a region 3' of a trinucleotide repeat sequence in the nucleic acid sequence;
ii) a first forward primer, wherein said first forward primer has a target sequence within the trinucleotide repeat sequence in the nucleic acid sequence and a unique 5' tail sequence; and
iii) a second forward primer, wherein the target sequence of the said second forward primer is a sequence complementary to the unique 5' tail sequence of the first forward primer
to generate an amplified product comprising a trinucleotide repeat sequence.

The nucleic acid for use in the present disclosure may be any nucleic acid, for example, in one embodiment, the nucleic acid is DNA. The DNA may be genomic DNA. In one embodiment the trinucleotide repeat expansion is selected from (CAG)n, (CGG)n, (GCC)n, (GAA)n or (CTG)n wherein n is from 1->200, for example, from 1 to 250, for example from 5 to 44, for example from 45 to 54, or for example from 55 to 200. In one embodiment, the trinucleotide repeat is (CGG)n.

The trinucleotide repeat expansion may be associated with a trinucleotide repeat disorder. In one embodiment the trinucleotide repeat disorder is selected from group consisting of polyglutamine (PolyQ) diseases and non-polyglutamine diseases.

The polyglutamine disease may be selected from the group consisting of DRPLA (Dentatorubro-pallidoluysian atrophy), HD (Huntington's disease), SBMA (Spinobulbar muscular atrophy or Kennedy disease), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCA7 (Spinocerebellar ataxia Type 7) and SCA17 (Spinocerebellar ataxia Type 17).

The non-polyglutamine disease may be selected from the group consisting of FXS (Fragile X syndrome), FXTAS (Fragile X-associated tremor ataxia syndrome), FRAXE (Fragile XE mental retardation), FRDA (Friedreich's ataxia), DM (Myotonic dystrophy), SCA8 (Spinocerebellar ataxia Type 8), SCA12 (Spinocerebellar ataxia Type 12) and premature ovarian failure (POF).

In one embodiment the trinucleotide repeat is CGG and is associated with FXS, FXTAS and POF.

The nucleic acid may comprise DNA, cDNA, single stranded DNA, double stranded DNA, plasmid DNA, RNA, mixtures of DNA with other molecules, DNA or RNA from human or other mammals. In one embodiment, the nucleic acid is selected from RNA or DNA. In a further embodiment the nucleic acid is genomic DNA.

In one embodiment of the present disclosure there is provided a method for screening for a trinucleotide repeat sequence in a biological sample, wherein said method comprises the step of contacting a nucleic acid sequence obtained or derived from the biological sample under amplification conditions with:
i) a forward primer, wherein said reverse primer has a target sequence in a region 5' of a trinucleotide repeat sequence in the nucleic acid sequence;
ii) a first reverse primer, wherein said first reverse primer has a target sequence within the trinucleotide repeat sequence in the nucleic acid sequence and a unique 5' tail sequence; and
iii) a second reverse primer, wherein the target sequence of the said second reverse primer is a sequence complementary to the unique 5' tail sequence of the first reverse primer
to generate an amplified product comprising a trinucleotide repeat sequence.

In another embodiment of the disclosure described herein, there is provided a method for screening for a trinucleotide repeat sequence in a biological sample, wherein said method comprises the step of contacting a nucleic acid sequence obtained or derived from the biological sample under amplification conditions with:
i) a first primer, wherein said first primer has a target sequence in a region 3' or 5' of a trinucleotide repeat sequence in the nucleic acid sequence;
ii) a second primer, wherein said second primer has a target sequence within the trinucleotide repeat sequence in the nucleic acid sequence;
to generate an amplified product comprising a trinucleotide repeat sequence; and
analyzing said amplified product using DNA melt curve analysis.

In another embodiment of the disclosure described herein, there is provided a method for screening for a trinucleotide repeat sequence in a biological sample, wherein said method comprises the step of contacting a nucleic acid sequence obtained or derived from the biological sample under amplification conditions, wherein said nucleic acid has been pretreated with a reagent which selectively modifies unmethylated cytosine residues in the nucleotide sequence, with:
i) a first primer, wherein said first primer has a target sequence in a region 3' and/or 5' of a trinucleotide repeat sequence in the nucleic acid sequence;
ii) a second primer, wherein said second primer has a target sequence within the trinucleotide repeat sequence in the nucleic acid sequence and said primer is complementary to a methylated or unmethylated trinucleotide repeat sequence;
to generate an amplified product comprising a trinucleotide repeat sequence; and
analyzing said amplified product using DNA melt curve analysis.

In one embodiment of the disclosure described herein the first primer has a target sequence in a region 3' and 5' of a trinucleotide repeat sequence in the nucleic acid sequence.

In another embodiment of the disclosure, the second primer comprises a unique 5' tail sequence.

In another embodiment, the method further comprises contacting the nucleic acid sequence with a third primer, wherein the target sequence of the third primer is within the unique 5' tail sequence of the second primer.

In another embodiment, the first primer has a target sequence in a region 3' and 5' of a trinucleotide repeat sequence in the nucleic acid sequence.

It will be appreciated by those of skill in the art that the screening of both the 3' and 5' ends of the trinucleotide repeat may be performed separately or in a single multiplexed reaction.

Screening both the 3' and 5' ends of the trinucleotide repeat removes the possibility of false negative results. In the case of the CGG trinucleotide repeat it has been found by the applicant that on occasion at least part of the 3' sequence flanking the trinuceotide repeat is unexpectedly deleted. Accordingly, in these cases, whilst a patient may have a trinucleotide repeat, due to the deletion of at least part of the 3' flanking sequence the result of the method will show that no repeat is present. This has not been reported previously. Likewise, there may be occasions where at least part of the 5' sequence is deleted. Thus, it is an advantage of the method that both 3' and 5' analysis are performed to eliminate false negative results in patients that have a deletion of at least part of the 3' and or 5' sequence flanking the trinucleotide repeat.

Tissue Samples

The method as described herein is suitable for use in a sample of fresh tissue, frozen tissue, paraffin-preserved tissue and/or ethanol preserved tissue. The sample may be a biological sample. Non-limiting examples of biological samples include whole blood or a component thereof (e.g. plasma, serum), blood spots, cord blood, single cells, whole genome amplified nucleic acid, prenatal tissue (e.g., amniocytes, chorionic villus, cells in maternal circulation) urine, saliva lymph, bile fluid, sputum, tears, cerebrospinal fluid, bronchioalveolar lavage fluid, synovial fluid, semen, ascitic tumour fluid, breast milk and pus. In one embodiment, the sample of nucleic acid is obtained from blood, amniotic fluid or a buccal smear. In one embodiment, the sample is a whole blood sample.

A biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

Well-known extraction and purification procedures are available for the isolation of nucleic acid from a sample. The nucleic acid may be used directly following extraction from the sample or, more preferably, after a polynucleotide amplification reaction (e.g. PCR reaction). The amplified polynucleotide is then 'derived' from the biological sample.

In one embodiment, the nucleic acid may be a whole genome amplified nucleic acid obtained from a single cell.

Whole genome amplification is particularly useful in screening for trinucleotide repeat disorders in pre-implantation samples. The use of whole genome amplification can therefore be used to obtain a genetic screen of a preimplantation sample. Advantageously, the results of such a screen can be used to determine whether to proceed with implantation. In one embodiment, whole genome amplification is performed using multiple displacement amplification. In another embodiment whole genome amplification is performed using PCR.

Amplification Reactions

The amplification conditions for use in the methods of the present disclosure may comprise an amplification reaction, for example a polymerase chain reaction. In one embodiment of an amplification reaction, the nucleic acid sequence is denatured prior to amplification, for example by heat treatment. Preferably, the heat treatment is carried out at a temperature in the range selected from the group consisting of from about 70-110° C.; about 75-105° C.; about 80-100° C. and about 85-95° C. Preferably, the denaturation step is carried out at 95° C.

In one embodiment, an optional denaturation step is carried out for a period selected from the group consisting of from about 5 seconds to 30 minutes; about 30 seconds to 30 minutes; about 5-30 minutes; about 10-25 minutes and about 15-20 minutes. Preferably, the denaturation step is carried out for at least 15 minutes.

In one embodiment, the denaturation step comprises treating a nucleic acid with a denaturing agent. In one embodiment the denaturing agent is selected from betaine, DMSO or Q solution. It will be appreciated by those of skill in the art that other suitable denaturing agents may be used in accordance with the method of the present disclosure.

In one embodiment, the denaturing agent may be used in a concentration selected from the range of about 0.5-3M in a final reaction volume.

In one embodiment, the amplification step comprises a polymerase chain reaction (PCR). In one embodiment, the PCR reaction comprises 40 cycles at 99° C. for 2 minutes, 65° C. for 2 minutes and 72° C. for 3 minutes, and a final extension step at 72° C. for 10 minutes. It will be appreciated by those of skill in the art that these temperatures may be varied by +/−5° C.

In one embodiment, the method, according to the disclosure is performed in a single-tube PCR reaction.

In accordance with the amplification reaction of the present disclosure, it will be appreciated that the amplification/PCR reactions may be multiplexed.

Screening Methods

In one embodiment, the methods described herein further comprise the step of analysing an amplified product to determine the value of n, and comparing the result of said analysis against a standard to determine whether the amplified product corresponds to that of a normal allele, a full mutation allele, a pre-mutation allele or a gray zone allele in a male or female subject. In one embodiment, the methods described herein further comprise the step of analysing an amplified product to determine the determining the number of amplified products having any particular value of n. For example, determining, the number of amplified products having an n of from 3 and 44, the number of amplified products having an n of from 45 to 54, the number of amplified products having an n of from 55 to 200, and the, number of amplified products having an n of greater than 200.

In one embodiment of the present disclosure, wherein the trinucleotide repeat is (CGG)n, the value of n from 5 to 44 corresponds to that of a normal allele; n from 45-54 corresponds to that of a gray zone allele; n from 55-200 corresponds to that of a pre-mutation allele and n of more than 200 corresponds to that of a full mutation allele.

In one embodiment of the present disclosure, the method further comprises screening an amplified product for the presence of an interrupting sequence in the trinucleotide repeat region and, optionally, comparing the result of said screening against a standard to ascertain whether said amplified product corresponds to that of a normal allele. A normal allele may have at least two interrupting sequences. In one embodiment, the amplified product is screened for the presence or absence of at least two interrupting sequences.

Modification of Unmethylated Nucleic Acid Sequences

In one embodiment, the nucleic acid is treated, for example pre-treated, with a reagent which modifies or selectively modifies unmethylated cytosine residues. Such a reagent is useful for distinguishing methylated from unmethylated cytosine residues. This reagent is capable of converting unmethylated cytosine residues to uracil, whereas methylated cytosines remain unconverted. This difference in residue may be utilised to distinguish between methylated and unmethylated nucleic acid residues in a downstream process, for example an amplification reaction such as PCR, using primers which distinguish between cytosine and uracil (cytosine pairs with guanine, whereas uracil pairs with adenine). In one embodiment, the reagent comprises bisulphite, for example sodium bisulphite. In one embodiment the nucleic acid sequence is treated with sodium bisulphite prior to denaturation.

Thus, in one embodiment, treatment of the nucleic acid with a reagent comprising bisulphite enables methylated and non-methylated nucleic acids to be distinguished.

In one embodiment, the method comprises pre-treating the nucleotide sequence with a reagent which selectively modifies unmethylated cytosine residues in the nucleotide sequence to produce detectable modified residues but which does not modify methylated cytosine residues. For example, in one embodiment, the reagent is sodium bisulphite and the reagent modifies an unmethylated (CCG)n sequence to (TTG)n and a methylated (CCG)n to (TCG)n. In this embodiment there is provided a first forward primer complementary to the treated methylated and/or unmethylated trinucleotide sequence.

In one embodiment, the nucleotide sequence to be treated with the regent has not been subjected to a previous amplification reaction.

Capillary Electrophoresis, Melt Curve Analysis and DNA Chip Analysis

In one embodiment of the present invention the amplified product may be analysed by capillary electrophoresis, melt curve analysis or on a DNA chip or any other electrophoretic gel. Using capillary electrophoresis of a product amplified using primers described herein, dTP-PCR peak patterns may be observed that can distinguish samples carrying only normal, AGG-interrupted alleles from samples carrying expanded alleles without AGG interruptions.

According to methods described herein, alleles with interruptions may result in a discontinuous series of product peaks, whilst alleles without interruptions may result in a continuous series of product peaks.

Males carry only one X chromosome, hence all males are expected to carry only one FMR1 allele. A normal unaffected male is expected to have only one FMR1 allele of normal length. According to methods described herein, and assuming no loss of AGG interruptions, a discontinuous series of discrete dTP-PCR product peaks may be observed. In both pre-mutation and full mutation males, a continuous series of dTP peaks may be observed, due to the presence of expanded FMR1 alleles with loss of the 3' AGG interruptions. Exceptions to these predicted patterns may occur in males that are size mosaics, where there are alleles with two or more different lengths in the same sample.

Females carry two X chromosomes, hence all females are expected to carry two FMR1 alleles. In a normal females, there should be two FMR1 alleles with repeat lengths in the normal range. Hence, discontinuous peak patterns similar to that of a normal male may be observed. In both premutation and full mutation females, a combination of continuous and discontinuous peak patterns may be observed, due to the presence of both normal and expanded alleles.

In one embodiment, the analysis is performed by DNA melt curve analysis. Advantageously, using DNA melt curve analysis, the method according to the disclosure, can be performed in a one tube closed homogenous system.

The application of melt curve analysis using the method in accordance with the disclosure permits the distinction between alleles containing a trinucleotide repeat. This simplified analysis is advantageous in newborn screening.

Labels

The primers according to the disclosure may additionally comprise a detectable label, enabling the probe to be detected. In one embodiment the fluorescent labels may be active in the blue, yellow, green and far red areas of the spectrum. In a preferred embodiment, non-limiting examples of fluorescent labels that may be used in the method of the disclosure include: fluorescent markers or reporter dyes, for example, 6-carboxyfluorescein (6FAM™), NED™ (Applera Corporation), HEX™ or VIC™ (Applied Biosystems); TAMRA™ markers (Applied Biosystems, CA, USA), ROX. It will be appreciated by those of skill in the art that other alternative fluorescent labels may also be used in the method according to the present disclosure.

In another embodiment chemiluminescent markers may be used, for example Ruthenium probes; and radioactive labels, for example tritium in the form of tritiated thymidine. $^{32}$-Phosphorus may also be used as a radiolabel.

Alternatively the label may be selected from the group consisting of electroluminescent tags, magnetic tags, affinity or binding tags, nucleotide sequence tags, position specific tags, and or tags with specific physical properties such as different size, mass, gyration, ionic strength, dielectric properties, polarisation or impedance.

In one embodiment, the detectable label may be directly or indirectly attached to the primer. In one embodiment, the labeled primer is the reverse primer. In one embodiment, the detectable label comprises a fluorescent moiety attached at a 5' end of the probe. In a most preferred embodiment, the label is selected from 6-FAM and NED.

In an alternative embodiment, the nucleic acid is detected with a nucleic acid-intercalating fluorophore. Preferably, the intercalating fluorophore is SYBR Green or EvaGreen and the like. It will be appreciated by those of skill in the art that other intercalating fluorophores may be used that are active in the blue, yellow, green and far red areas of the spectrum. It will be further appreciated that other intercalating fluorophores may be used in accordance with the present disclosure.

Primers, Sets of Primers and Kits

In one embodiment of the disclosure described herein there is provided a first primer, a second primer and a third primer.

In another embodiment of the disclosure described herein the first primer is SEQ ID NO:10, the second primer is SEQ ID NO:11 and the third primer is SEQ ID NO:12.

In another embodiment of the disclosure described herein the first primer is SEQ ID NO:21, the second primer is SEQ ID NO:22 and the third primer is SEQ ID NO:23

In another embodiment of the disclosure described herein the first primer comprises or consists of a nucleic acid sequence selected from the group consisting of SEQ ID NO:2, SEQ ID NO:20, SEQ ID NO:24 and SEQ ID NO:26.

In another embodiment of the disclosure described herein the first primer comprises or consists of a nucleic acid sequence selected from the group consisting of SEQ ID NO:2, SEQ ID NO:5, SEQ ID NO:7, SEQ ID NO:10, SEQ ID NO: 20, SEQ ID NO:21; SEQ ID NO:24 and SEQ ID NO:26

In another embodiment of, the disclosure described herein the second primer comprises or consists of a nucleic acid sequence selected from the group consisting of SEQ ID 1, SEQ ID 4, SEQ ID NO:8 SEQ ID NO:11 SEQ ID NO:22 SEQ ID NO:25 and SEQ ID NO:27.

In another embodiment of the disclosure described herein the third primer comprises or consists of a nucleic acid sequence selected from the group consisting of SEQ ID NO:3, SEQ ID NO:6, SEQ ID NO:9, SEQ ID NO:12 and SEQ ID NO:23.

In another embodiment of the disclosure described herein the second primer comprises or consists of a nucleic acid sequence selected from the group consisting of SEQ ID NO:1, SEQ ID NO:4, SEQ ID NO:25 and SEQ ID NO:27.

In another embodiment of the disclosure described herein the third primer comprises or consists of a nucleic acid sequence selected from the group consisting of SEQ ID NO:3 and SEQ ID NO:6.

In one embodiment of the disclosure described herein, there is provided a primer selected from the group comprising or consisting of the nucleotide sequence of any of SEQ ID NO:1 to SEQ ID NO:27 or complements thereof.

In one embodiment of the disclosure described herein there is provided a primer comprising or consisting of a nucleotide sequence in which the nucleotide sequence comprises:
(i) a first sequence selected from the group consisting of any one of (CAA)9 (SEQ ID NO:13), (CGA)8 (SEQ ID NO:14) and (CGG)5 (SEQ ID NO:15); and
(ii) a unique sequence selected from the group consisting of any one of CGACTGTTTGACCCTACCTTA (SEQ ID NO:16); ATTCCATCCCAGTTTGTCAGC (SEQ ID NO:17); TACCGATACGCATCCCAGTTTGTCAGC (SEQ ID NO:18); and TACCATTACGCATCCCGATTTGTCTTA (SEQ ID NO:19).

In one embodiment of the disclosure described herein there is provided a set of primers for screening for a trinucleotide repeat sequence, in which the nucleotide sequences of the primers comprise or consist of the following sequences, or complements thereof: SEQ. ID NO:1, SEQ ID NO:2, and SEQ ID NO:3.

In one embodiment of the disclosure described herein there is provided a set of primers for screening for a trinucleotide repeat sequence, in which the nucleotide sequences of the primers comprise or consist of the following sequences, or complements thereof: SEQ ID NO:4, SEQ ID NO:5, SEQ ID NO:6 and SEQ ID NO:20.

In one embodiment of the disclosure described herein there is provided a set of primers for screening for a trinucleotide repeat sequence, in which the nucleotide sequences of the primers comprise or consist of of the following sequences, or complements thereof: SEQ ID NO:7, SEQ ID NO:8, and SEQ ID NO:9.

In one embodiment of the disclosure described herein there is provided a set of primers for screening for a trinucleotide repeat sequence, in which the nucleotide sequences of the primers comprise or consist of the following sequences, or complements thereof: SEQ ID NO:10, SEQ ID NO:11, and SEQ ID NO:12.

In one embodiment of the disclosure described herein there is provided a set of primers for screening for a trinucleotide repeat sequence, in which the nucleotide sequences of the primers comprise or consist of the following sequences, or complements thereof: SEQ ID NO:21, SEQ ID NO:22, and SEQ ID NO:23.

In one embodiment of the disclosure described herein there is provided a set of primers for screening for a trinucleotide repeat sequence, in which the nucleotide sequences of the primers comprise or consist of the following sequences, or complements thereof: SEQ ID NO:3, SEQ ID NO:24, and SEQ ID NO:25.

In one embodiment of the disclosure described herein there is provided a set of primers for screening for a trinucleotide repeat sequence, in which the nucleotide sequences of the primers comprise or consist of the following sequences, or complements thereof: SEQ ID NO:6, SEQ ID NO:26, and SEQ ID NO:27.

In one embodiment, the primers for performing 3' direct TP-PCR are selected from Table 5.

In one embodiment, the primers for performing 5' direct TP-PCR are selected from Table 8.

In one embodiment, the primers for performing 3' methylation-specific Triplet-Primed PCR (msTP-PCR) assay are selected from Table 1 or Table 4.

In one embodiment, the primers for performing 5' methylation-specific Triplet-Primed PCR (msTP-PCR) assay are selected from Table 9.

In one embodiment of the disclosure described herein there is provided a kit when used in the method according to the disclosure described herein, comprising:
one or more primers, in which the nucleotide sequences comprise or consist of the following sequences, or complements thereof: SEQ ID NO.1, SEQ ID NO.2, SEQ ID NO.3 and SEQ ID NO.4, SEQ ID NO:5, SEQ ID NO:6 and SEQ ID NO:20; or
one or more primers, in which the nucleotide sequences comprise or consist of the following sequences, or complements thereof: SEQ ID NO.7, SEQ ID NO.8, and SEQ ID NO.9; or
one or more primers, in which the nucleotide sequences comprise or consist of the following sequences, or complements thereof SEQ ID NO.10, SEQ ID NO:11 and SEQ ID NO:12; or
one or more primers, in which the nucleotide sequences comprise or consist of the following sequences, or complements thereof: SEQ ID NO.21, SEQ ID NO.22, and SEQ ID NO.23; or
one or more primers, in which the nucleotide sequences comprise or consist of the following sequences, or complements thereof: SEQ ID NO:3, SEQ ID NO:24 and SEQ ID NO:25; or
one or more primers, in which the nucleotide sequences comprise or consist of the following sequences, or complements thereof: SEQ ID NO:6, SEQ ID NO:26 and SEQ ID NO:27, optionally together with instructions for use.

Preferably, the kit further comprises a DNA polymerase. In one embodiment the DNA polymerase is a thermostable DNA polymerase. In another embodiment the DNA polymerase is selected from the group consisting of Taq DNA polymerase and Pfu DNA polymerase. In one embodiment, the DNA polymerase is Taq DNA polymerase. It will be appreciated by those of skill in the art that other thermostable DNA polymerases may be used in the method according to the disclosure In another embodiment of the disclosure described herein, the kit further comprises sodium bisulphite.

In a one embodiment of the disclosure described herein, the further comprises a denaturing agent.

In another embodiment of the disclosure described herein, the kit further comprises dNTPs.

EXAMPLES

Non-limiting examples of the disclosure, including the best mode, and a comparative example will be further described in greater detail by reference to the following Examples, which should not be construed as in any way limiting the scope of the disclosure.

Example 1

Methylation-Specific Triplet-Primed PCR (msTP-PCR) for Detection of AGG-Interspersed and Uninterrupted CGG Repeats in Normal, Permutation and Full Mutation FMR1 Alleles Materials and Methods
DNA Samples Genomic DNA samples for initial assay optimization were extracted from 6 lymphoblastoid cell lines obtained from the Coriell Cell Repositories (Camden, N.J.) (GM04738, GM06891, GM06852, GM04479, GM06907, and GM07537) using standard phenol-chloroform extraction and ethanol precipitation. The FMR1 genotypes of these DNAs were previously determined by Southern blot and/or PCR. An additional 19 DNA samples, including 15 selected from a panel of previously characterized fragile. X mutation reference DNA samples with repeat lengths representing the main fragile X phenotypes and critical diagnostic cutoffs, were also analyzed.

Assay Overview

Figure 1:
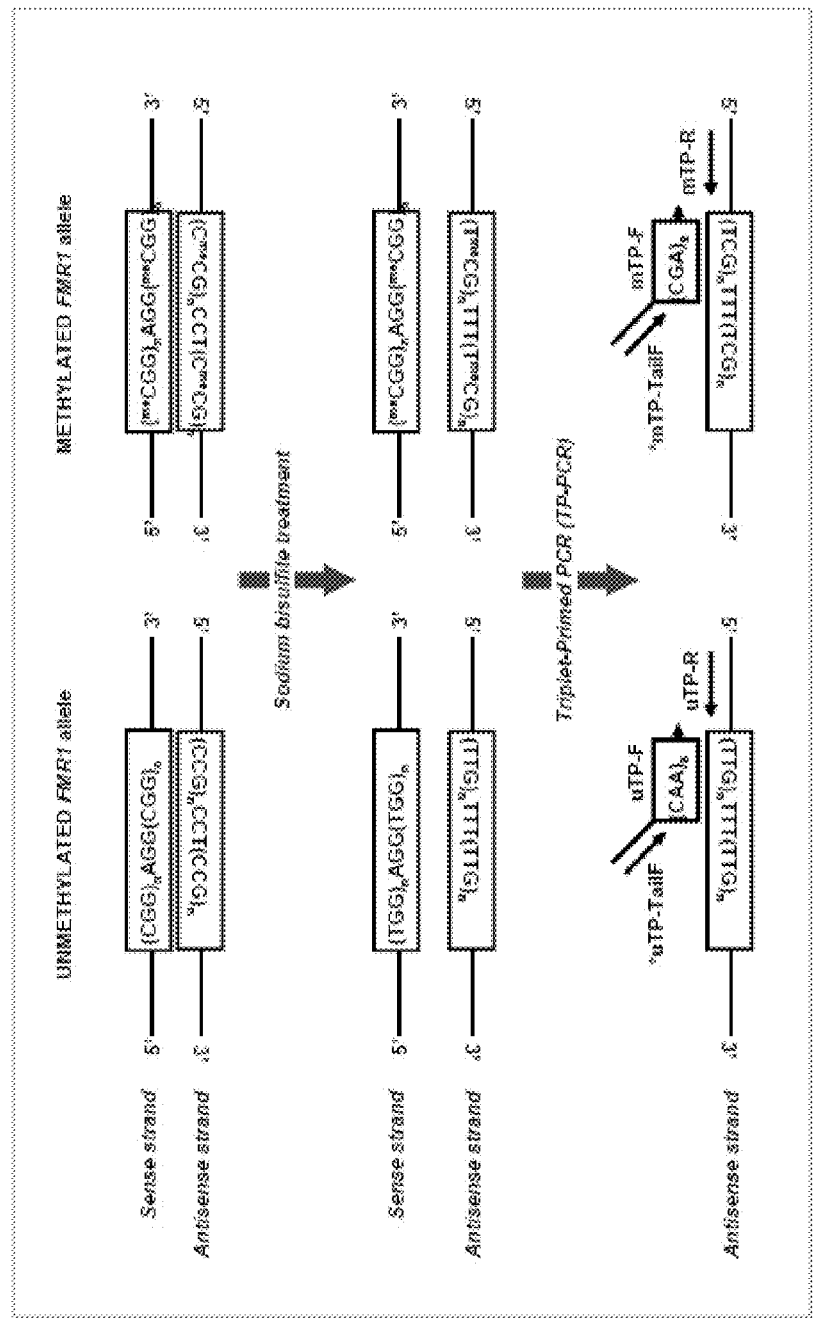
Figure 2:
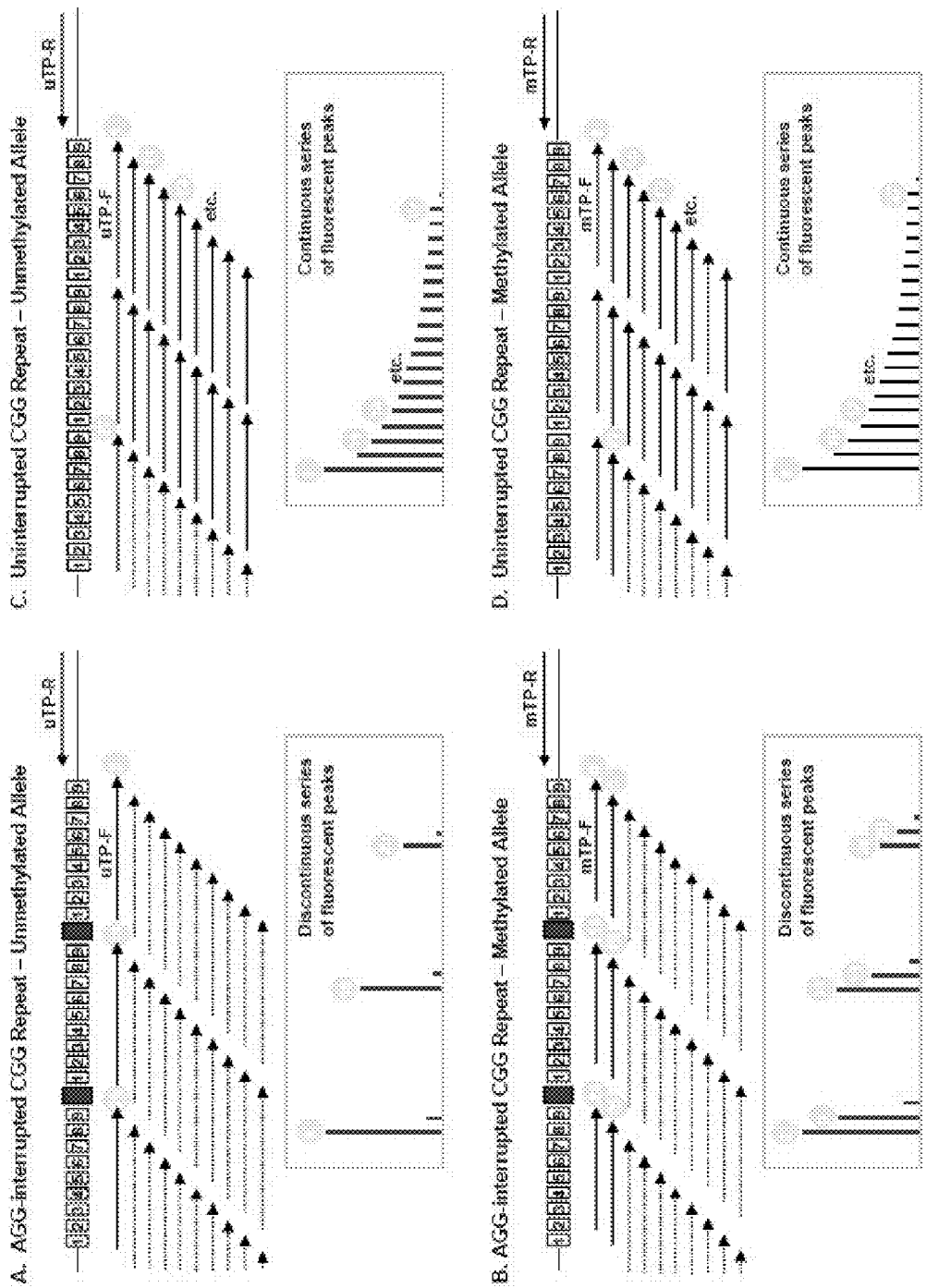
Figure 3:
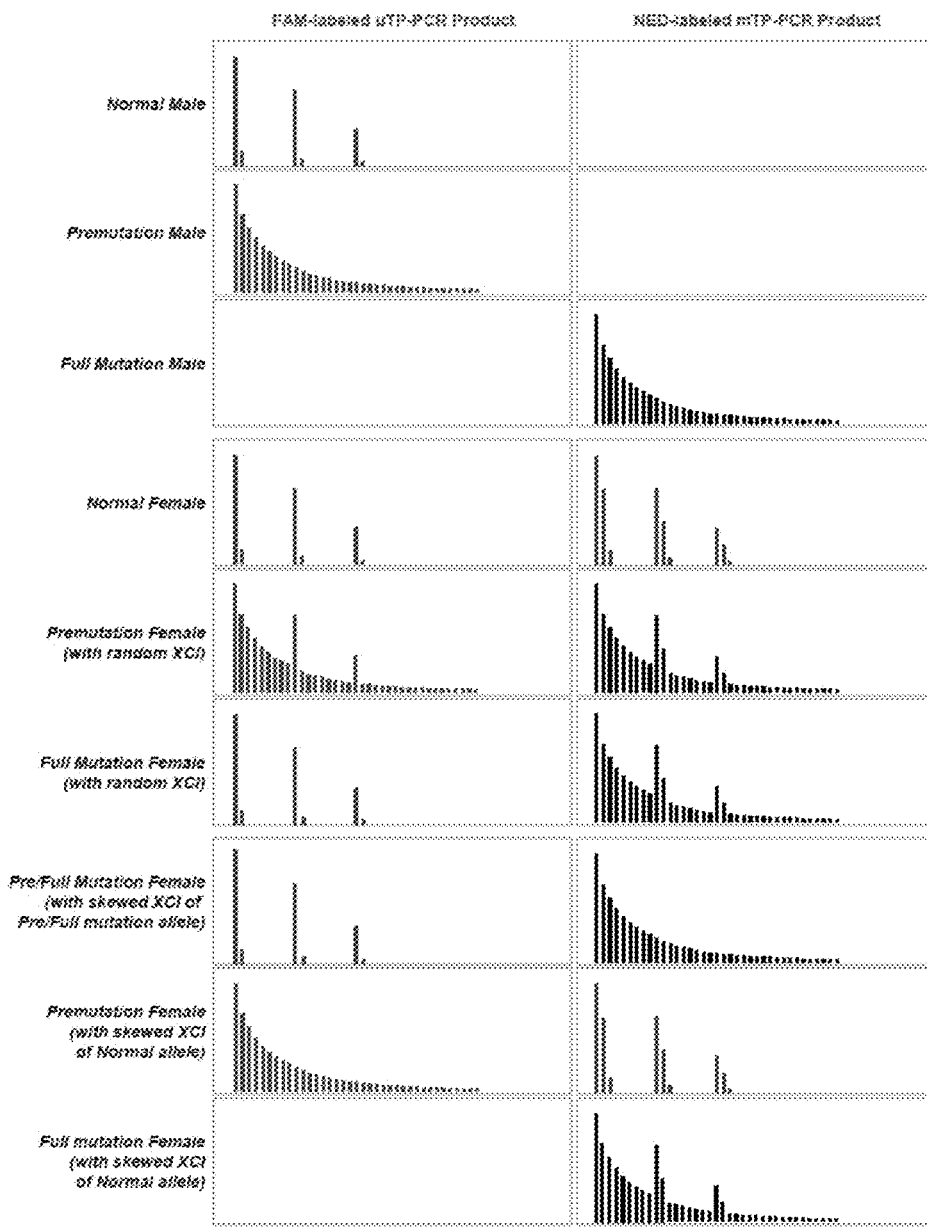

Genomic DNA was treated with sodium bisulfite, and a methylation-specific triplet-primed PCR (msTP-PCR) strategy was employed to differentially amplify and detect methylated and unmethylated alleles using fluorescently labeled primers (FIG. 1). Amplification products were resolved by capillary electrophoresis to determine peak patterns. Normal, non-expanded alleles will produce an interrupted peak pattern, while premutation and full mutation expanded alleles will produce an uninterrupted peak pattern (FIG. 2). The unmethylated and methylated allele PCR peak patterns together enable accurate genotype classification in both males and females (FIG. 3).

Sodium Bisulfite Conversion

Sodium bisulfite treatment of DNA differentially modifies methylated and unmethylated cytosines. In particular, converting unmethylated cytosines to uracils, which are then amplified as thymines during PCR. In contrast, methylated cytosines, such as those found in methylated CpG dinucleotides, are resistant to bisulfite conversion and thus remain as cytosines during PCR. As a result, identical target sequences with different methylation states are converted to non-identical sequences following sodium bisulfite treatment—antisense unmethylated CCG repeats will be amplified as TTGs and antisense methylated CCG repeats will be amplified as TCGs.

Genomic DNA samples were subjected to sodium bisulfite modification using the EZ-DNA Methylation Gold kit (Zymo Research) with modifications. Briefly, the CT conversion reagent solution was prepared by adding 660 μl of deionised water, 250 μl of M-dilution buffer and 50 μl of M-dissolving buffer to the tube containing the CT conversion reagent, with mixing and frequent vortexing for 10 minutes at room temperature. Separately, 5 μl of M-dilution buffer was added to 1 μg of DNA, and the volume was adjusted to 50 μl with deionised water. A 100 μl aliquot of the CT conversion reagent solution was then added to the DNA sample and incubated at 55° C. for 3 hours. The treated DNA was purified using the Zymo-spin IC column according to manufacturer instructions, eluted with 20 μl of TE buffer (10 mM Tris-HCl, 1 mM EDTA, pH 8.0) and stored at −20° C. until further use.

Methylation-Specific PCR

Two sets of primers were designed to amplify the antisense strand of bisulfite-modified FMR1, one set specific to the unmethylated allele (uTP-PCR) and the other specific to the methylated allele (mTP-PCR) (FIG. 1, Table 1). The forward primers uTP-F and mTP-F are complementary to the antisense strand bisulfite modified unmethylated (TTG) and methylated (TCG) repeats, respectively, and each carries a unique non-complementary 5' tail sequence (Table 1; FIG. 1).

The forward primers anneal within the repeat sequence itself. Therefore, the presence or absence of AGG interruptions within the CGG repeat influences the annealing ability of these primers and thus the resultant amplification products. These are reflected in the electropherogram patterns of the PCR products. FIG. 2 illustrates how presence or absence of interruptions within the repeat influences primer annealing and resultant electropherogram patterns.

Panels A and B of FIG. 2 assume a 29 repeat allele containing two evenly spaced AGG interruptions in a 9+9+9 configuration (where '9' indicates the number of CGGs and '+' indicates an AGG interruption). Primer uTP-F anneals to 9 repeats of bisulfite-modified unmethylated DNA on the antisense strand, i.e. (TTG)$_9$. In FIG. 2A, annealing of uTP-F closest to uTP-R generates the shortest PCR product containing 9 repeats, which is reflected as the first peak of the electropherogram. Due to the presence of the AGG (now bisulfite-converted to TTT) interruption, the next available uTP-F annealing site is the middle (TTG)9 stretch, which results in a PCR product containing 19 repeats and is reflected as the second product peak 30 bp away from the first. Similarly, the third and final uTP-F annealing site is the furthest (TTG)$_9$ stretch from primer uTP-R, which generates a PCR product with 29 repeats and is reflected as the peak product with the largest size. Hence, the uTP-PCR peak pattern for a 29-repeat allele with a 9+9+9 configuration is expected to consist of three discrete peaks that are 30 bp apart.

TABLE 1

Primers used in amplification of sodium bisulfite-treated methylated and unmethylated FMR1 alleles.

| Primer | 5' → 3' sequence | GenBank ID: nucleotides |
|---|---|---|
| uTP-PCR | | |
| uTP-F (SEQ ID NO. 1) | CGACTGTTTGACCCTACCTTA (CAA)$_9$ | n.a. |
| uTP-R (SEQ ID No. 2) | TGTTTTTGAGAGGTGGGTTGT GGGTGTTT | X61378: 2805→2777 |
| Fam-uTP-TailF (SEQ ID NO. 3) | Fam-CGACTGTTTGACCCTACCTTA | n.a. |
| mTP-PCR | | |
| mTP-F (SEQ ID NO. 4) | ATTCCATCCCAGTTTGTCAGC (CGA)$_8$ | n.a. |
| mTP-R (SEQ ID NO. 5) | CGTTTTCGAGAGGTGGGTTGC GGGCGTTC | X61378: 2805→2777 |
| Ned-mTP-TailF (SEQ ID NO. 6) | Ned-ATTCCATCCCAGTTTGTCAGC | n.a. | mTP-PCR is similar to uTP-PCR, but with minor differences (FIG. 2B). The mTP-F primer consisting of a unique 5' tail sequence and a 3' stretch of 8 repeats anneals within the repeat region of the anti-sense strand of bisulfite-modified methylated DNA. Hence, on an allele with a 9+9+9 configuration, mTP-F will be able to anneal completely at two positions within the 5' most segment of the repeat region, giving rise to the 2 shortest PCR products with 8 and 9 repeats (first and second peaks, FIG. 2B). Subsequently it will not be able to anneal and extend successfully across the interruption and will only prime the next pair of amplification products from the second segment, with a ~27 bp gap between the two pairs of peaks (third and fourth peaks, FIG. 2B). This pattern is repeated for the last segment at the 3' end of the repeat region, with a pair of peaks 3 by apart from each other and consisting of 28 and 29 repeats respectively (fifth and sixth peaks, FIG. 2B). Hence, an mTP PCR peak pattern for a normal allele with 9+9+9 configuration should be similar to that of uTP PCR, except that there should be 3 pairs of discrete peaks, separated by gaps of ~27 bp with no amplification products. More peaks in each cluster will be expected where there are more repeats before the primer encounters an interruption or unique repeat-flanking sequences.

Panels C and D of FIG. 2 assume an FMR1 allele with 27 uninterrupted repeats, i.e. containing no AGG interruption. Consequently, both the uTP-F and mTP-F primers are able to anneal anywhere within the uninterrupted 27-repeat stretch, generating electropherograms with 19 and 20 consecutive PCR products, respectively, of increasing size and decreasing peak height, with each product differing in size by 3 bp. Larger uninterrupted repeats, such as those found in premutation and full mutation alleles, will be expected to generate a correspondingly greater number of product peaks.

Each 50 µl msTP-PCR reaction contained 0.2 µM each of primers uTP-R, mTP-R, Fam-labeled uTP-TailF, and Ned-labeled mTP-TailF, 0.02 µM each of primers uTP-F and mTP-F, 0.2 mM dNTPs, 3 units of HotStarTaq DNA polymerase (Qiagen), 1× Q solution (Qiagen), IX supplied PCR buffer (Qiagen) and 2 µl of bisulfite-modified DNA. An initial denaturation at 95° C. for 15 minutes was followed by 40 cycles of 98° C. for 1 minute, 60° C. for 1 minute and 72° C. for 2 minutes.

Capillary Electrophoresis and GeneScan Analysis

Each 1 µl of amplification product was mixed with 0.3 µl of GeneScan® 500 Rox size standard and 9 µl of HiDi formamide (Applied Biosystems). The mixtures were subjected to capillary electrophoresis on a 3130XL Genetic Analyzer (Applied Biosystems) for 50 minutes, and the electropherograms were analyzed using GeneMapper® software (Applied Biosystems, version 4.0).

FIG. 3 provides a schematic illustration of GeneScan electropherogram results that can be expected from normal, premutation and full mutation males and females. A normal unaffected male is expected to generate only a uTP-PCR product with a normal allele electropherogram pattern, with absent mTP-PCR product. Similarly, a premutation male will not produce an mTP-PCR product, but instead generate a uTP-PCR electropherogram pattern characteristic of a long uninterrupted CGG repeat. In marked contrast, an affected male's full mutation expanded allele is methylated and inactive. Therefore, there should be absent a uTP-PCR product but an mTP-PCR electropherogram pattern consistent with a long uninterrupted CGG repeat should be present.

In normal females both uTP- and mTP-PCR products showing normal AGG-interrupted allele peak patterns are expected, as a result of random X chromosome inactivation (XCI) mediated methylation of both alleles. In premutation females with random XCI, an overlap of AGG-interrupted and uninterrupted repeat peak patterns are expected from both uTP- and mTP-PCRs, again due to random XCI of the normal and premutation alleles. In full mutation females, however, the full mutation allele is fully methylated and inactive, regardless of the inactivation state of the X chromosome on which it resides. Therefore, uTP-PCR will only generate the chromatogram pattern of the normal AGG-interrupted allele, while mTP-PCR will produce an overlap of AGG-interrupted and uninterrupted repeat peak patterns.

Extremely skewed XCI can be detected in a premutation or full mutation female through differences in the msTP-PCR chromatogram results compared to their random XCI female counterparts. For example, in premutation or full mutation females with predominant inactivation (>95%) of the X chromosome carrying the premutation/full mutation allele, the uTP-and mTP-PCRs predominantly amplify only the AGG-interrupted normal and uninterrupted expanded alleles, respectively. Conversely, if a premutation female shows predominant inactivation of the X chromosome carrying the normal allele, the uTP- and mTP-PCRs will predominantly amplify only the premutation and normal alleles, respectively. Finally, if a full mutation affected female shows predominant inactivation of the X chromosome carrying the normal allele, the uTP-PCR will yield absent PCR product while the mTP-PCR will amplify both the normal and expandeded alleles to produce an overlap of AGG-interrupted and uninterrupted repeat peak patterns.

HUMARA Assay

Figure 6:
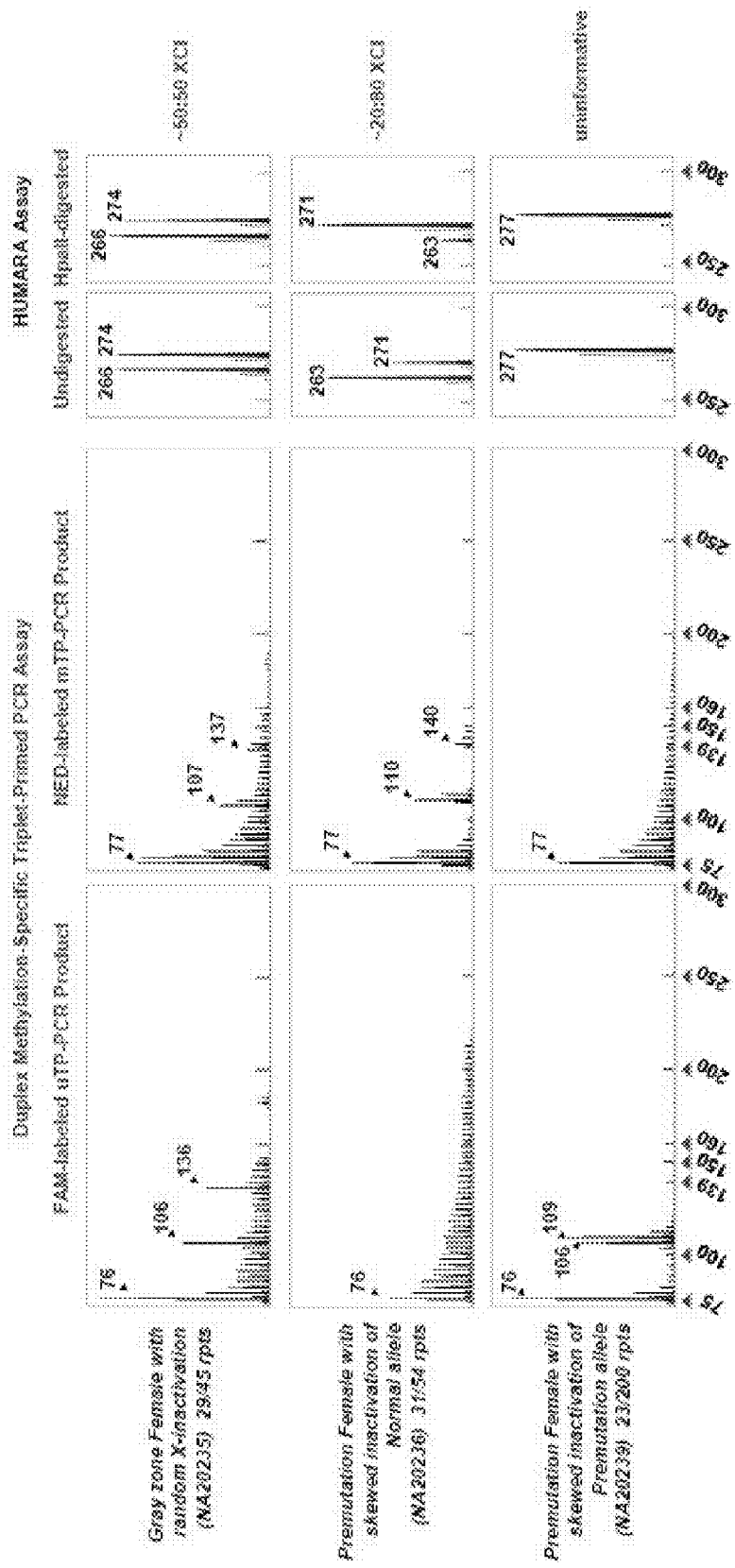

The HUMARA assay was carried out as described (23), but with minor modifications. Briefly, 500 ng of genomic DNA was digested with 5 units of Hpall (Fermentas) in a reaction volume of 20 µl. For each digested sample, a parallel reaction containing only genomic DNA and reaction buffer but without restriction enzyme was performed. Reactions were incubated at 37° C. for 4 h, and terminated at 95° C. for 10 min. A 4 µl aliquot of each reaction product was amplified in a 25 µl PCR reaction containing 0.2 mM dNTPs, 1 unit HotStarTaq DNA polymerase (Qiagen), IX supplied PCR buffer (Qiagen), and 0.2 µM each of forward primer (5'-GCTGT-GAAGGTTGCTGTTCCTCAT-3')(SEQ ID No:30) and Fam-labeled reverse primer (5'-TCCAGAATCTCTTCCA-GAGCGTGC-3') (SEQ ID NO:31)—An initial denaturation at 95° C. for 15 minutes was followed by 30 cycles of 98° C. for 30 s, 60° C. for 30 s and 72° C. for 30 s. PCR products were analyzed using GeneMapper® software (Applied Biosystems, version 4.0) and allele peak heights of digested and undigested aliquots of each sample were compared to obtain X-chromosome inactivation (XCI) ratios (FIG. 6).

Sequencing

All male genomic DNA samples used for optimization and validation of the assay were sequenced to determine actual repeat lengths and structures of the FMR1 alleles. PCR across the repeat region was performed using 100 ng of DNA, 0.4 µM each of primers c and f (4), 0.5 mM dNTPs, 2.5 units of HotStarTaq DNA polymerase (Qiagen), 2.5× Q solution (Qiagen), 1× supplied PCR buffer (containing 1.5 mM $MgCl_2$, Qiagen), and an additional 0.75 mM $MgCl_2$ (Qiagen) in a volume of 25 µL. An initial denaturation at 95° C. for 15 min was followed by 35 cycles of 98° C. for 1 min, 65° C. for 1 min and 68° C. for 8 min. A 5 µl aliquot of each PCR product was cleaned up using 10 units of exonuclease I and 2 units of shrimp alkaline phosphatase (SAP). Sequencing was performed using 0.32 µM of primer c, together with 8 µl of BigDye terminator ready reaction mix, 1× Q solution and 1 µl of purified template in a total reaction volume of 20 µl.

Sequencing products were resolved by capillary electrophoresis on a 3130XL Genetic Analyzer (Applied Biosystems).

Results

Figure 4:
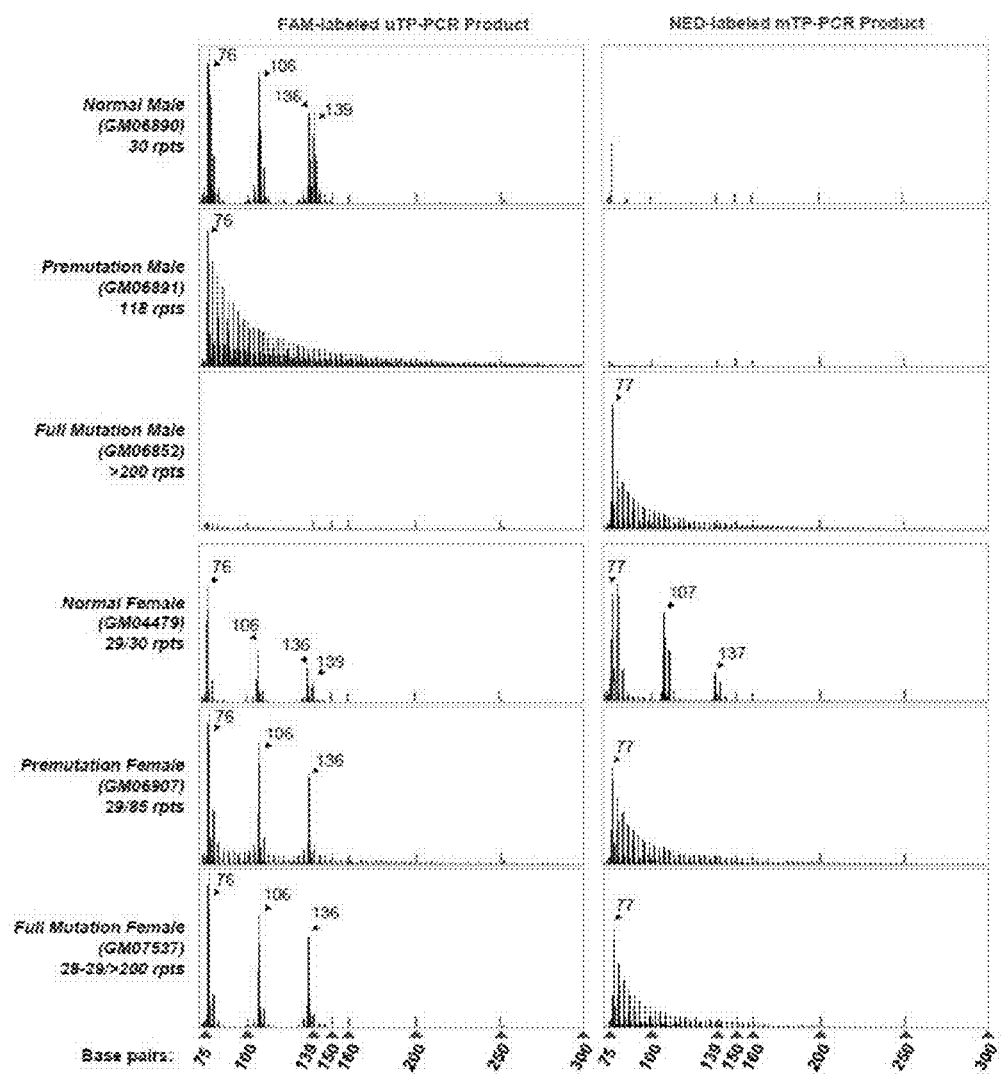

The assay was first tested on three male and three female DNA samples that are known to carry normal, premutation, and full mutation alleles of the FMR1 gene, and the chromatogram results are presented in FIG. 4.

In the normal male (GM04738), only uTP-PCR products forming a normal AGG-interrupted allele peak pattern was observed, and mTP-PCR products were absent (FIG. 4, normal male). The uTP peak clusters are separated by clear zones of 30 bp, characteristic of an expected normal uTP-PCR peak pattern. In the premutation male sample (GM06891), only uTP-PCR products forming a continuous ladder of amplification products, 3 bp apart from one another and between 76 bp to >500 bp, were observed. There was no mTP-PCR amplification, indicating that none of the expanded alleles are hypermethylated (FIG. 4, premutation male). In a full mutation male (GM06852), a continuous mTP peak ladder pattern with products from 76 bp to ~400 bp was observed, as full expansion alleles are hypermethylated (FIG. 4, full mutation male). In this full mutation male sample, very low levels of continuous uTP peaks was also observed, which could be attributed to mosaicisms in DNA methylation states often seen in FXS patients (24). There were no clear zones observed in the peak ladders of both the premutation and full mutation males, indicating the loss of 3' AGG interruptions in both cases.

In a normal female sample (GM04479), both uTP- and mTP-PCRs produced the expected normal peak patterns (FIG. 4, normal female). The absence of continuous peak ladder patterns in both sets of PCRs confirms that this female is of normal genotype. In the premutation female (GM06907), 3 uTP peak clusters 30 bp apart from one another, interspersed with a continuous ladder of low uTP peaks from 76 bp to ~340 bp were observed (FIG. 4, premutation female). This is an indication of extreme skewing of XCI, with almost all of its expanded alleles found on the inactive X chromosomes. The expanded premutation alleles on inactive X chromosomes gave rise to continuous mTP peak ladders from 76 bp to ~325 bp, masking the presence of low levels of normal peak clusters arising from normal alleles on inactive X chromosomes. Similarly for the full mutation female (GM07537), the absence of discrete mTP peak clusters amongst the continuous mTP peak ladders and a normal uTP peak cluster pattern also indicates the presence of extremely skewed XCI, with most of the normal alleles found on unmethylated, active X-chromosomes (FIG. 4, full mutation female). The results of both GM06907 and GM07537 support previous observations made in a fluorescent methylation-specific PCR assay, where both samples have shown extreme skewing of XCI (17).

Assay Validation

Figure 7:
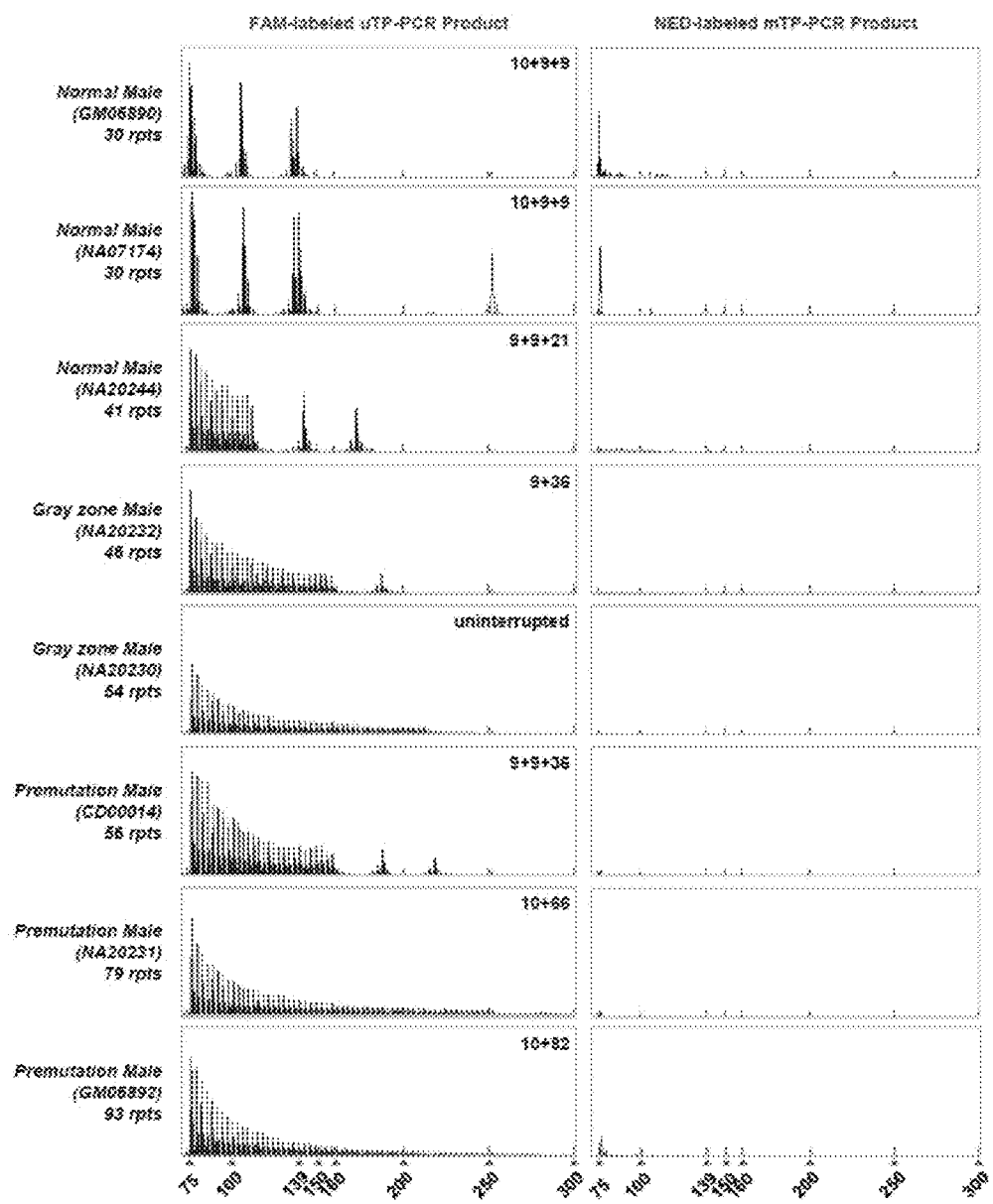
FIG. 7 shows GeneScan electropherogram traces of male samples obtained using msTP-PCR procedure. Repeat sizes are in accordance to information provided by Coriell cell repository, where applicable.
Figure 8:
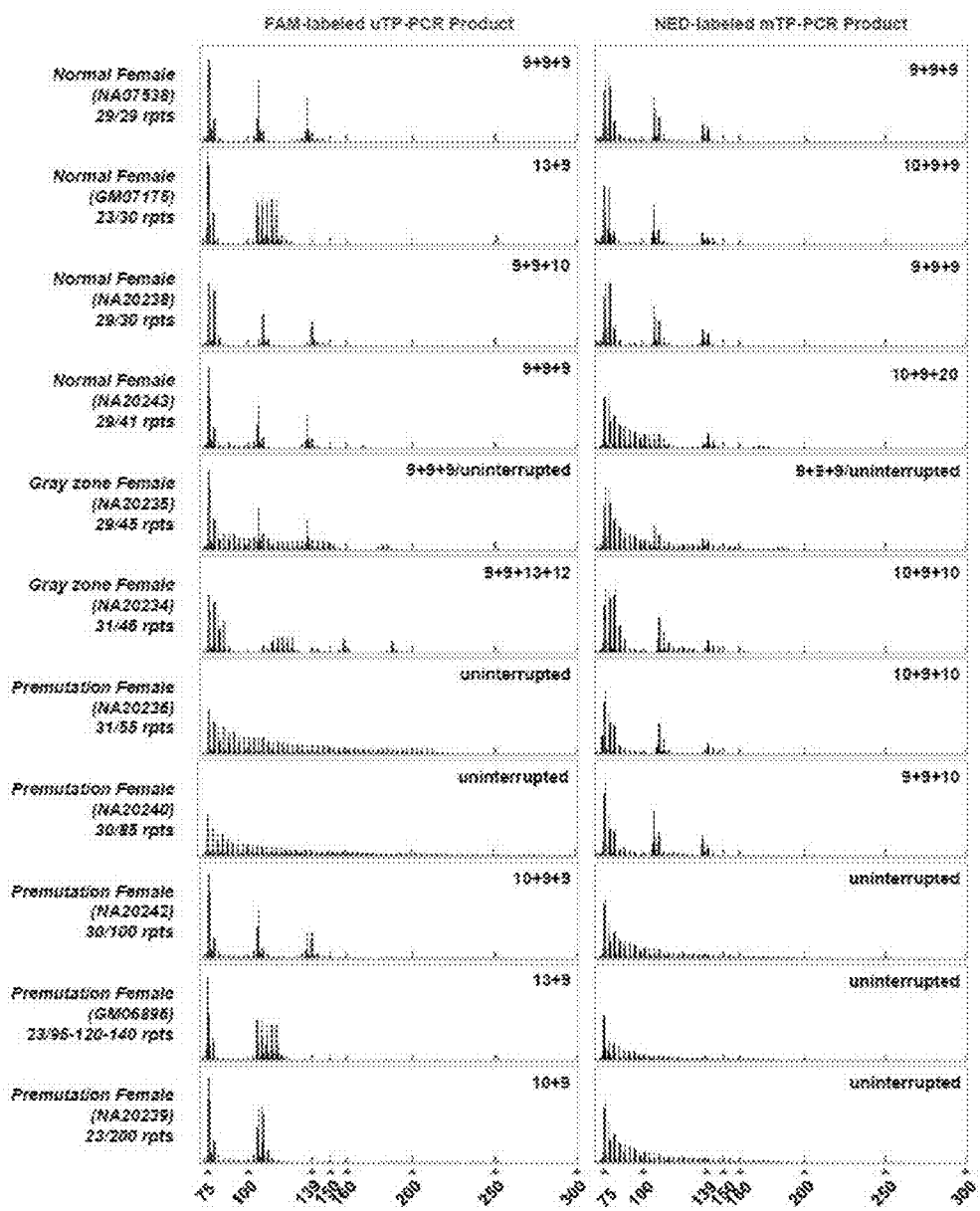
FIG. 8 shows GeneScan electropherograms of female samples using msTP-PCR procedure. Repeat sizes are in accordance to information provided by Coriell cell repository, where applicable.

Further validation of the assay was performed on 19 additional DNA samples, consisting of both male and female samples with repeat lengths spanning across three of the four main allelic genotypes—normal, gray zone and premutation (FIGS. 7 and 8). As with the 6 samples above, premutation samples were easily distinguished from normal samples by the presence of continuous peak ladders where there is an expansion, either in uTP- or mTP-PCR. Normal alleles gave rise to discrete clusters of peaks separated by clear zones where the uTP-F and mTP-F primers fail to anneal and extend successfully across the interruptions. In samples with 2 interruptions, there were three discrete clusters of peaks separated by two clear zones (eg, GM06890, NA07538, FIGS. 7 and 8 respectively). Where there is only 1 interruption in the repeat region, only two peak clusters separated by one clear zone were observed (NA20232, and uTP-PCR of GM07175, FIGS. 7 and 8). Four peak clusters with three clear zones were observed in the uTP-PCR amplification of NA20234, an indication that it has three interruptions in the unmethylated repeat region (FIG. 8).

Peak Patterns and Repeat Lengths

Figure 5:
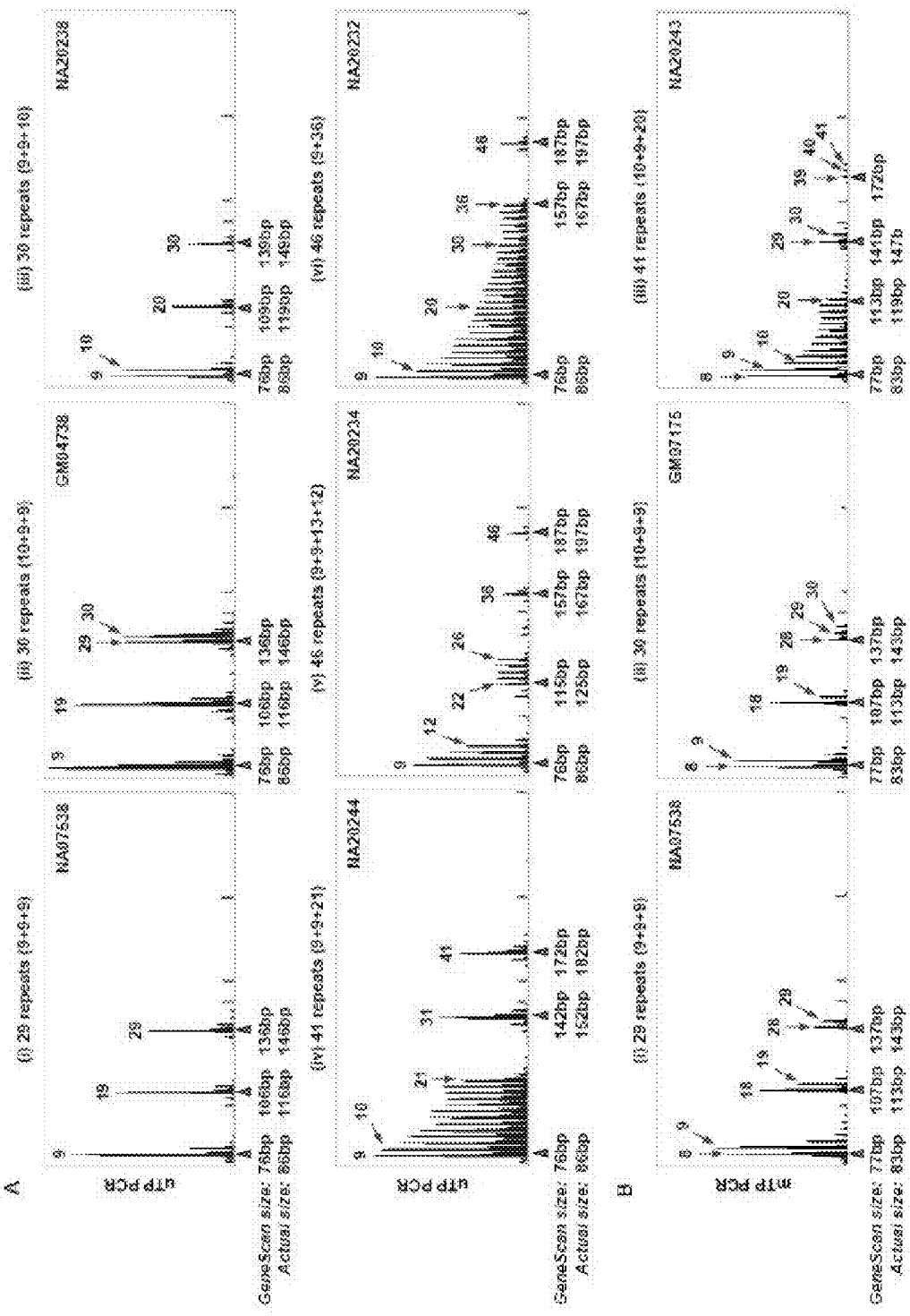

In addition to being able to distinguish normal from expanded alleles, a number of different repeat structures were also observed within each genotype among the samples studied. The most commonly seen repeat structures are the three discontinuous peak clusters characteristic of normal alleles, where the repeat regions carry two interruptions, with an interruption after every 9 or 10 repeats. FIGS. 5Ai-iii show uTP-PCR electropherogram results from unmethylated alleles with the 9+9+9, 10+9+9 and 9+9+10 CGG repeat patterns, while FIGS. 5Bi-ii show mTP-PCR electropherograms from methylated alleles with the 9+9+9 and 10+9+9 repeat patterns. Variations in repeat lengths of each segment result in varying number of peaks in each peak cluster, as shown in FIGS. 5Aiv-vi and FIG. 5Biii. Hence, by looking at the electropherogram peak patterns, it is possible to distinguish between alleles of identical repeat lengths but different repeat structures (FIGS. 5Aii versus 5Aiii).

Analysing the repeat structures of alleles also permitted the deduction of repeat lengths from both uTP- and mTP-PCR peak clusters, independent of the sizes provided by the electropherogram size markers. Repeat lengths could be deduced from the peak patterns of both male and female duplex ms-TPPCR electropherograms where possible and sequenced male samples to verify the repeat lengths and structures obtained through duplex msTP-PCR. For normal, grey zone and some premutation males where sequencing was successful, the sequencing results supported our predictions of repeat structures and sizes through duplex msTP-PCR. Although the predicted size of NA20230 by duplex msTP-PCR differed from the consensus length, it corresponded with the submitter's estimated length. For NA20231, the size obtained from duplex ms-TPPCR differed slightly from both the consensus and the estimated lengths by one and two repeats respectively, and was one repeat shorter than sized by sequencing. Samples with long stretches of continuous peak ladders beyond 300 bp could not be sized by duplex ms-TP-PCR due to the presence of stutter peaks towards the end of the ladder (Table 2, FIG. 7, (21)).

TABLE 2

Male genomic DNA samples from Coriell Cell Repository lines used for assay optimization and validation.

| | No. of CGG | 5' → 3' repeat pattern (Total no. of repeats) | | |
|---|---|---|---|---|
| | repeats as provided by | Duplex methylation specific TP-PCR | | Direct PCR |
| Coriell ID | Coriell | uTP-PCR | mTP-PCR | Sequencing |
| GM 06890 | 30 | 10 + 9 + 9 (30) | — | 10 + 9 + 9 (30) |
| GM 04738 | not indicated | 10 + 9 + 9 (30) | — | 10 + 9 + 9 (30) |
| NA 07174 | 30 [30]^ | 10 + 9 + 9 (30) | — | 10 + 9 + 9 (30) |
| NA 20244 | 41 [41]^ | 9 + 9 + 21 (41) | — | 9 + 9 + 21 (41) |
| NA 20232 | 46 [46]^ | 9 + 36 (46) | — | 9 + 36 (46) |
| NA 20230 | 54 [53]^ | 54 uninterrupted repeats | — | uninterrupted repeat (54) |
| CD 00014 | 56 [56]^ | 9 + 9 + 36 (56) | — | 9 + 9 + 36 (56) |
| NA 20231 | 79 [76]^ | 10 + 66 (77) | — | 10 + 67 (78) |
| GM 06892 | 93 [86]^ | 10 + 82 (93) | — | 10 + 82 (93) |

TABLE 2-continued

Male genomic DNA samples from Coriell Cell Repository lines used for assay optimization and validation.

| | No. of CGG repeats as provided by | 5' → 3' repeat pattern (Total no. of repeats) | |
|---|---|---|---|
| | | Duplex methylation specific TP-PCR | Direct PCR |
| Coriell ID | Coriell | uTP-PCR | mTP-PCR | Sequencing |
| GM 06891 | 118 | >140 uninterrupted repeats | — | PCR successful (~193 rpts); sequencing failed |
| GM 06852 | >200 | — | >90 uninterrupted repeats | PCR and sequencing failed |

^Repeat lengths in brackets are consensus data from a consortium study (14).

Among female samples, all normal and gray zone alleles that were sized by duplex msTP-PCR method corresponded with the sizes provided by CCR and the consensus study (21). However, discrepancies among sizes by duplex msTP-PCR, CCR and the consensus study were more common among premutation alleles, which might be due to PCR stuttering often seen in amplifications of large repeat regions (Table 3, FIG. 8).

Two of the samples used for validation have similar allele sizes (54 repeats in NA20230 and 56 repeats for CD000014) but different repeat structures (FIG. 7). The longer stretch of uninterrupted repeats in NA20230 may cause this allele to be more predisposed to expansions than CD000014, despite the larger allele size of CD000014 active and inactive X chromosomes, as can be seen from the similar peak patterns from uTP- and mTP-PCRs (FIG. 6, first row).

Each PCR shows three discontinuous clusters of peaks arising from the 29 repeat alleles with 2 AGG interruptions, as well as continuous ladder patterns arising from the 45 repeat alleles. In contrast, skewed XCI were observed in samples NA20236 and NA20239 (FIG. 6, middle and last rows). In NA20236, the shorter 31 repeat alleles are predominantly found on the inactive X chromosomes, resulting in the normal pattern of three discontinuous peak clusters from mTP-PCR, which are absent from uTP-PCR. The larger 55 repeat alleles are predominantly found on the active X chromosome, and are reflected in the form of a continuous ladder of uTP peaks that are higher than the continuous mTP peak patterns (FIG. 6, middle row). The reverse is seen from NA20239—most of the shorter 23 repeat alleles are found on the active X chromosome while most of the larger 200 repeat alleles are found on the inactive X chromosomes, which results in predominantly discontinuous uTP peaks and continuous mTP peaks, with the mTP peak ladders masking the presence of discontinuous mTP peak clusters (FIG. 6, last row).

For samples NA20235 and NA20236, HUMARA assay results were informative and indicative of equal and skewed XCI respectively, while sample NA20239 was un-informative at the HUMARA locus.

Determining FMR1 Repeat Lengths

Discrepancies between the expected and observed sizes of the amplicons were observed, with the uTP and mTP PCR products migrating about 10 bp (3 repeats) and 6 bp (2 repeats) faster than expected respectively, due to enhanced electrophoretic mobility of fragments containing triplet

TABLE 3

Female genomic DNA samples from Coriell Cell Repository lines used for assay optimization and validation.

| | No. of CGG repeats as | Duplex methylation specific TP-PCR: 5' → 3' repeat pattern (Total no. of repeats)* | |
|---|---|---|---|
| Coriell ID | provided by Coriell | uTP-PCR | mTP-PCR |
| NA 07538 | 29/29 [29/29]^ | 9 + 9 + 9 (29) | 9 + 9 + 9 (29) |
| GM 07175 | 23/30 | 13 + 9 (23) | 10 + 9 + 9 (30) |
| GM 04479 | not indicated | 10 + 9 + 9 (30) | 9 + 9 + 9 (29) |
| NA 20238 | 29/30 [29/30]^ | 9 + 9 + 10 (30) | 9 + 9 + 9 (29) |
| NA 20243 | 29/41 [29/41]^ | 9 + 9 + 9 (29) | 10 + 9 + 20 (41) |
| NA 20235 | 29/45 [29/45]^ | 9 + 9 + 9 (29)/45 uninterrupted repeats | 9 + 9 + 9 (29)/45 uninterrupted repeats |
| NA 20234 | 31/46 | 9 + 9 + 13 + 12 (46) | 10 + 9 + 10 (31) |
| NA 20236 | 31/55 [31/53]^ | uninterrupted repeat (54) | 10 + 9 + 10 (31) |
| GM 06907 | 29/85 | 9 + 9 + 9 and 11 + 81 (29 and 93) | 10 + 80 (91) |
| NA 20240 | 30/85 [30/80]^ | uninterrupted repeat (94) | 9 + 9 + 10 (30) |
| NA 20242 | 30/100 [30/73]^ | 10 + 9 + 9 (30) | uninterrupted repeat (73-74) |
| GM 06896 | 23/95-120-140 | 13 + 9 (23) | uninterrupted repeat (>75) |
| NA 20239 | 23/200 [20/no consensus]^ | 10 + 9 (20) | uninterrupted repeat (>90) |
| GM 07537 | 28-29/>200 | 9 + 9 + 9 (29) | uninterrupted repeat (>90) |

^Repeat lengths in [brackets] are consensus data from a consortium study (14).
*Except for NA 20235, results of most samples are suggestive of almost completely skewed X-inactivation.

Skewed X-Inactivation

With the ability to analyse unmethylated and methylated alleles separately, the results of this duplex ms-TPPCR assay can be used to inform on the skewing patterns of female FMR1 alleles. In NA20235, each of the two FMR1 alleles of different sizes are distributed almost equally on both the repeats (24). Thus, sizing of the amplicons to determine repeat lengths will result in under-sizing of both the unmethylated and methylated alleles. By using the number of peaks and repeat structures to predict allele lengths, we have successfully overcome the problem of inherent enhanced mobility of triplet repeat-rich fragments over the size standards used during capillary electrophoresis. By analyzing repeat structures, all alleles except very large premutation and full mutation alleles were accurately sized from this assay (Tables 2 and 3). The largest allele that could be sized was a 93 repeat allele (GM06892, Table 2 and FIG. 7). Unlike assays that utilize primers flanking the repeat region for FMR1 expansion detection, there is no preferential amplification of normal alleles over expanded alleles with this current approach, thus avoiding apparent homozygosity issues where a female sample that is homozygous for normal alleles may be mistaken for a female sample with one normal allele and a second full mutation allele that is refractory to PCR.

Determining FMR1 Repeat Methylation States

With the ability to analyse amplification products from unmethylated and methylated alleles separately, we were also able to tell if the CGG repeats were methylated. The presence of a continuous mTP peak pattern in a male sample is a clear indication of a full mutation affected individual. Analyses of amplification products from female samples are complicated by XCI—while the absence of continuous mTP peak patterns indicates that the individual is not affected with FXS, the reverse may mean that she is either affected with FXS, or that she carries a large premutation allele and has extremely skewed XCI, such that most of her expanded premutation alleles are-on the inactive X chromosomes. Together with CGG repeat lengths and patterns, XCI ratio may also play a role in determining susceptibility or severity of premature ovarian failures (POF) in premutation females. In light of these studies, it is interesting to note that our assay could also detect skewed XCI ratios of FMR1 alleles in female samples. Among the female samples that we analysed, there were 7 which have one allele in the normal, low repeat size range (less than 40 repeats) and the other allele in the medium repeat size range (large normal, gray zone and premutation alleles greater than 40 repeats) (Table 2). Of these 7 samples, 3 (NA20242, NA20243 and GM06907) carried most of their lower repeat size alleles on the active X chromosome and were not detectable by mTP PCR, 2 (NA20235 and NA20234) had approximately equal distribution of their lower repeat size alleles on inactive and active X chromosomes and were detected in both uTP and mTP PCR, and the rest (NA20236 and NA20240) carried most of their lower repeat size alleles on the inactive X chromosome and were only detected by mTP PCR (FIG. 8). While several studies on the manifestation of POF in premutation females have shown that it may not be associated with XCI ratios, the conclusions were based on the evaluations of the amplification of the human androgen receptor locus before and after digestion by a methylation-sensitive enzyme (28,29). Hence, re-evaluation of subjects using the duplex ms-PCR assay may be able to provide a more accurate representation of how the distributions of premutation alleles on inactive and active X chromosomes influence POF manifestation in premutation females.

Summary

The duplex ms-PCR approach described herein is technically simple with reliable results that can be obtained within a day. It has significant advantages over our previous triple ms-PCR assay and other existing assays as the current assay requires only one PCR setup and is robust enough to detect very large premutation and full mutation alleles in both males and females, and distinguish between large premutation from full mutation alleles in males and females with equal XCI ratios. Considering a hypothetical sample size of 50,000 males, with known FXS frequency of 1 in 4000 males, using the duplex ms-PCR approach as a screen will result in only ~13 full mutation male samples being channeled for size confirmation by Southern blot analysis. For a similar sample size of 50,000 females, with known FXS frequency of 1 in 6000 females and premutation allele prevalence of 1 in 259 females (30,31), and taking into consideration that most moderate expansions in the premutation range can be sized, in reality, less than 200 of 50,000 (<0.4%) will be large premutation and full mutation female samples that require follow up analysis by Southern blot if exact repeat sizes have to be reported. This drastically reduces the cost and effort of FXS diagnosis. Unlike most PCR assays, there is no issue of apparent homozygosity of normal alleles in pre- and full mutation females. Premutation females that are mosaic for premutation and full mutation alleles can also be immediately detected by, the presence of continuous series of peaks in both uTP and mTP-PCR. This assay is able to reveal various properties of an FMR1 repeat region, that, when taken together, facilitates informed and accurate clinical diagnosis and counseling.

Example 2

Methylation-Specific Triplet-Primed PCR (msTP-PCR) Assay for Distinguishing Between Normal and Expanded FMR1 Alleles by Melting Curve Analysis Genomic DNA was modified by sodium bisulfite as described in Example 1. The PCR strategy is similar to Example 1, except that uTP and mTP PCRs were carried out in two separate reactions with non-fluorescent labeled primers, and SYBR green nucleic acid dye is added to the reaction before PCR amplification. The SYBR green dye-bound PCR products were subjected to melting curve analysis on the Lightcycler480 instrument. In general, one should expect to see two categories of melting peak patterns, one arising from a normal, non-expanded repeat with two or more AGG interruptions, and another arising from an expanded repeat with one AGG interruption at the 5' end of the repeat region or none at all.

Methylation-Specific PCR

Two sets of primers were designed to amplify the antisense strand of bisulfite-modified DNA as in Example 1, but with minor modifications to the primer sequences, the addition of SYBR green nucleic acid dye and separate setup of uTP and mTP reactions. All primers were not fluorescent-labeled and positions of primers in relation to the repeat region were as described in Example 1. PCR and thermocycling conditions were also as described. The primers are set forth in Table 4, with the exception of mTP-R, which is replaced by mTP-R2. Thus, the primers used in this example are uTP-F, uTP-R and uTP-TailF for the unmethylated allele-specific PCR; mTP-F, mTP-R2, and mTP-TailF for the methylated allele-specific PCR. Both PCRs are performed separately in this example.

TABLE 4

Primers used in amplification of sodium bisulfite-treated methylated and unmethylated FMR1 alleles.

| Primer | 5' → 3' sequence | GenBank ID: nucleotides |
|---|---|---|
| uTP-PCR | | |
| uTP-F (SEQ ID NO. 1) | CGACTGTTTGACCCTACCTTA (CAA)$_9$ | n.a. |
| uTP-R (SEQ ID No. 2) | TGTTTTTGAGAGGTGGGTTGT GGGTGTTT | X61378: 2805→2777 |

TABLE 4-continued

Primers used in amplification of sodium bisulfite-treated methylated and unmethylated FMR1 alleles.

| Primer | 5' → 3' sequence | GenBank ID: nucleotides |
|---|---|---|
| Fam-uTP-TailF (SEQ ID NO. 3) | Fam-CGACTGTTTGACCCTACCTTA | n.a. |
| mTP-PCR | | |
| mTP-F (SEQ ID NO. 4) | ATTCCATCCCAGTTTGTCAGC (CGA)$_8$ | n.a. |
| mTP-R2 (SEQ ID NO. 20) | GGTTGCGGGCGTTCGAGGTTTAG | X61378: 2790→2768 |
| Ned-mTP-TailF (SEQ ID NO. 6) | Ned-ATTCCATCCCAGTTTGTCAGC | n.a. | uTP-TailF and mTP-TailF have the same sequence as Fam-uTP-TailF and Ned-mTP-TailF, respectively. The only difference between these two sets is uTP-TailF and mTP-TailF are unlabeled, while Fam-uTP-TailF and Ned-mTP-TailF are labeled with 5' fluorescent tags.

Melting Curve Analysis

20 μl of either uTP or mTP PCR products were subjected to a melting programme consisting of denaturation at 95° C. for 1 min, a temperature-hold step at 60° C. for 1 min, and then slow temperature ramping from 60° C. to 95° C., with 50 readings of fluorescence intensity per degree during temperature ramping. The Lightcycler480 software was used to collect fluorescence intensities and convert the data into melting curve and melting peak plots.

Results

Figure 9:
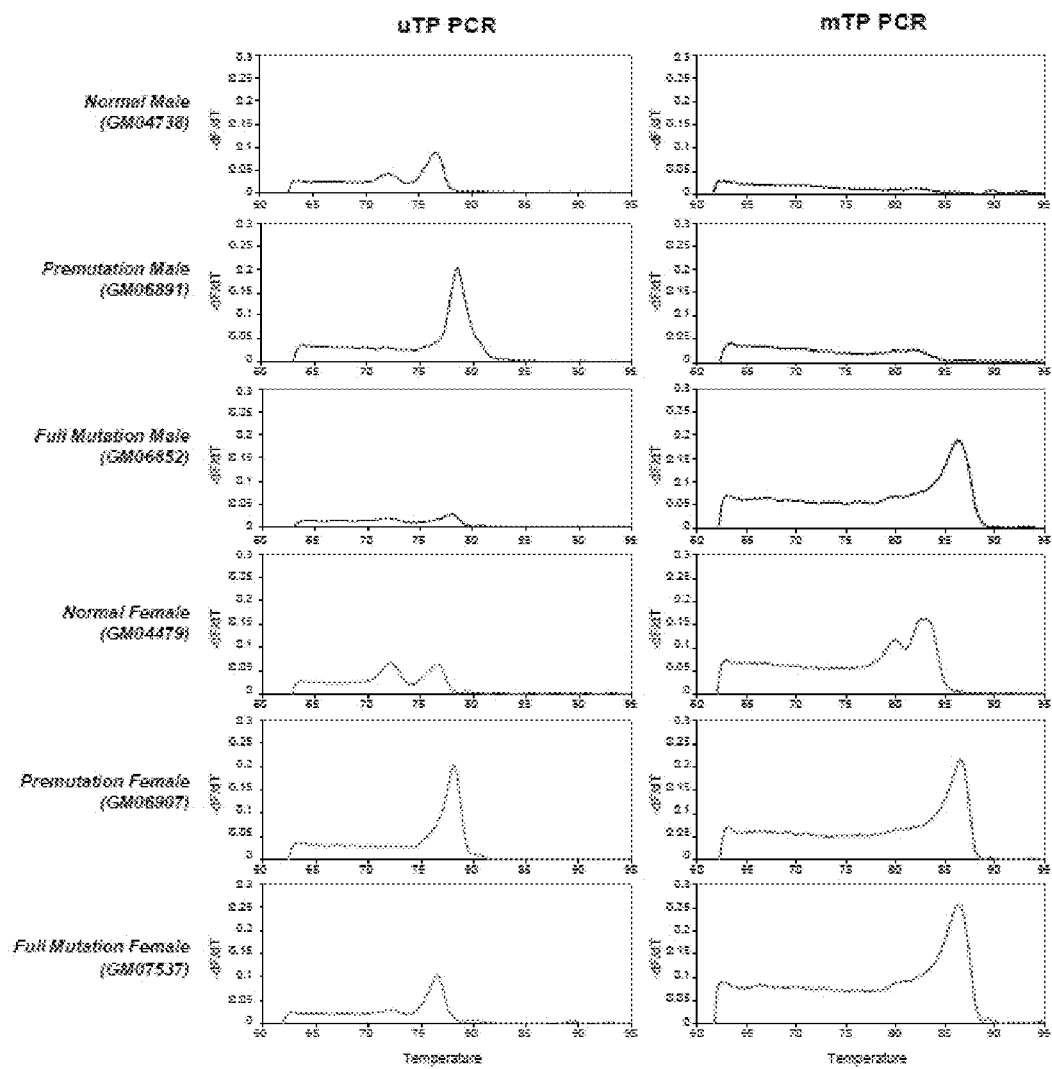
FIG. 9 shows melting peaks of, uTP (left) and mTP (right) PCR products of male and female samples using msTP-PCR procedure Y-axis: negative derivative of fluorescence with respect to time; X-axis: Temperature in ° C.

Clear differences in melting peak patterns and melting temperatures between normal and expanded alleles for both uTP and mTP PCR were observed (FIG. 9). uTP PCR products of normal alleles gave melting profiles with one or two peaks, with the highest melting temperature at ~76° C. (uTP melting curves of normal male, normal female and full mutation female). In contrast, uTP PCR products of unmethylated expanded alleles gave melting profiles consisting of only 1 peak with the highest point at ~78° C. (uTP melting curves of premutation male and premutation female). Similarly, mTP PCR products of normal alleles gave a melting profile of two peaks between 80-85° C. (mTP curves of normal female), while those of methylated expanded alleles gave melting profiles consisting of only 1 peak with a gradual upward slope but a steep downward slope, with the highest point of the peak at >85° C. (mTP melting curves of premutation female and full mutation male and female). Hence, we would be able to detect the presence of both unmethylated and methylated expanded alleles, and distinguish them from normal alleles, by analyzing the shapes and melting temperatures of both uTP and mTP melting peaks.

Example 3

Methylation-Specific Triplet-Primed PCR (msTP-PCR) Assay for Distinguishing Normal from Expanded FMR1 Alleles on a Chip-Based Microfluidic Platform Assay Overview Genomic DNA was modified by sodium bisulfite as described herein. The PCR strategy is similar to Example 2 in that the uTP and mTP PCRs were carried out in two separate reactions with non-fluorescent labeled primers. PCR products were resolved on a DNA chip in the Agilent Bioanalyzer 2100. In general, one should expect to see two categories of electrophoretic profiles, one arising from a normal, non-expanded repeat with two or more AGG interruptions, and another arising from an expanded repeat with one AGG interruption at the 5' end of the repeat region or none at all.

Methylation-Specific PCR

Two sets of primers were designed to amplify the antisense strand of bisulfite-modified DNA as in Example 1, but with separate setups of uTP and mTP reactions. All primers were not fluorescent-labeled and positions and sequences of primers in relation to the repeat region were as described in Example 1. PCR and thermocycling conditions were also as described.

Resolution of PCR Products on the Bioanalyzer

The Agilent DNA 1000 chips were prepared as per the manufacturer's protocol, with slight modifications. Briefly, each DNA 1000 chip can analyze 12 samples in ~35 min. After the chip has been primed with the gel-dye mix (provided in kit), 3 μl of either uTP or mTP PCR products and 3 μl of DNA marker (provided in kit) were added into each of the 12 sample wells. 1 μl of DNA ladder (provided in kit) and 5 μl of DNA marker were added into designated well. The chip is then loaded into the Bioanalyzer after brief vortexing. The Bioanalyzer software then collects the fluorescence data from each well and generates the electrophoretic profiles for each sample sequentially.

Results

Clear differences in the electrophoretic profiles of normal and expanded alleles can be observed (Figure xxx). uTP PCR products of normal alleles gave three discrete peaks with sizes that range from 93 bp to 145 bp (uTP PCR, normal female). The peaks at ~20 bp and 60 bp are non-specific peaks. In contrast, uTP PCR products of expanded alleles gave a series of merged peaks that are lower than the normal peaks but which are still above the baseline (uTP PCR, premutation and full mutation females). The mTP PCR products of normal alleles gave three separate peaks at 89 bp, 112 bp and 137 bp (mTP PCR, normal female). The two peaks at ~200 bp are due to non-specific amplification. In contrast, mTP PCR products of expanded alleles gave a series of merged peaks of decreasing heights, with the smallest amplicon at 90 bp (mTP PCR, premutation and full mutation females). Although the size resolution of peaks on the Bioanalyzer is lower than on the ABI Genetic Analyzer, we were still able to distinguish normal from expanded alleles based on the general electrophoretic profiles of the PCR amplicons.

Example 4

Direct Triplet-Primed PCR (dTP-PCR) Assay for Detecting Expanded FMR1 Alleles in Male and Female Samples Assay Overview The direct fluorescent PCR (dTP-PCR) assay for FMR1 expansions in non-modified DNA samples uses the same principle feature of a tailed forward primer annealing to and amplifying from the repeat region. The forward primer dTP-F is complementary to the CGG repeats and carries a unique 5' tail sequence. The Tail-F primer is complementary to the 5' tail sequence of dTP-F. The reverse primer f is 5' labeled with the fluorophore molecule FAM and anneals to the flanking sequence 3' of the repeat region (Table 5; FIG. 11). The fluorescent-labeled PCR products were subjected to capillary electrophoresis and PCR products visualized through the Fam channel.

12 shows examples of how interruptions in a triplet repeat region affect primer annealing within the repeat region and influence the PCR product electropherogram patterns.

TABLE 5

Primers used in amplification of FMR1 alleles

| Primer | 5' → 3' sequence | GenBank ID: nucleotides |
|---|---|---|
| Capillary electrophoresis and bioanalyzer analysis (Examples 4 & 6) | | |
| F (SEQ ID NO: 7) | AGCCCCGCATTCCACCACCAGCTCCTCCA | X61378: 2867→2838 |
| dTP-F (SEQ ID NO: 8) | TACCGATACGCATCCCAGTTTGTCAGC (CGG)$_5$ | n.a. |
| TailF (SEQ ID NO: 9) | TACCGATACGCATCCCATTTGTCAGC | n.a. |
| Post-PCR melting curve analysis (Example 5) | | |
| dTP-R (SEQ ID NO: 10) | GCACTTCCACCACCAGCTCCTCCATCTTCT | X61378: 2861→2832 |
| dTP-F2 (SEQ ID NO: 11) | TACCATTACGCATCCCGATTTGTCTTA (CGG)$_5$ | n.a. |
| TailF2 (SEQ ID NO: 12) | TACCATTACGCATCCCGATTTGTCTTA | n.a. |

In general, two categories of electrophoretic peak patterns should be observed, one arising from a normal, non-expanded repeat and another arising from an expanded repeat. Most normal, non-expanded alleles consist of 29 or 30 CGG repeats with two AGG interruptions, while premutation and full mutation alleles usually contain only one AGG interruption at the 5$^5$ end of the repeat region or none at all.

Direct Triplet-Primed PCR (dTP-PCR)

A set of 3 primers were designed to amplify from unmodified DNA at the FMR1 locus. Each 50 μl reaction contained 0.2 μM each of primers TailF and FAM-labeled f and 0.02 μM of primer dTP-F, 0.2 mM dNTPs, 3 units of HotStarTaq DNA polymerase (Qiagen), 2.5× Q solution (Qiagen), 1× supplied PCR buffer (Qiagen) and 50 ng of genomic DNA. An initial denaturation at 95° C. for 15 minutes was followed by 40 cycles of 99° C. for 2 minutes, 65° C. for 2 minutes and 72° C. for 3 minutes, and a final extension step at 72° C. for 10 minutes.

Capillary Electrophoresis and GeneScan Analysis

1 μl of each amplification product was mixed with 0.3 μl of GeneScan® 500 Rox size standard and 9 μl of HiDi Formamide (Applied Biosystems). The mixtures were heat denatured at 95° C. and rapidly cooled to 4° C. on a thermocycler before being loaded into an ABI 3130XL Genetic Analyzer (Applied Biosystems) for capillary electrophoresis. Each electrophoresis run takes 50 minutes, with an injection time of 18 seconds at 1200V. The electropherograms were analyzed using GeneMapper® software (Applied Biosystems, version 4.0). Alternatively, an injection voltage of 6 kV for 7 seconds can improve the quality of the electropherogram peaks.

Principles of Assay Design

The dTP-PCR primers were designed such that they could anneal and amplify all FMR1 alleles, regardless of size of the CGG repeat expansion. Designing the forward primer to anneal within the repeat region itself overcomes the factors that make expansions in the FMR1 locus refractory to PCR—its GC-rich nature and the lengths of the expansions, which are more than 200 CGG repeats in full mutation alleles. FIG.

FIG. 12A illustrates a hypothetical 29 repeat allele with an AGG interruption at every 9 CGG repeats (9+9+9 repeat pattern, with '+' representing an AGG interruption). The dTP-F primer consists of a unique 5' tail sequence and a 3' stretch of 9 repeats that anneals within the CGG repeat region. The dTP-F primer that anneals in the repeat region closest to the Fam-f primer gives the shortest PCR product consisting of 5 repeats (first peak of electropherogram, FIG. 12A). Subsequent annealing of dTP-F further upstream in the repeats results in larger amplicons, each increasing by 3 bp. dTP-F primer is able to anneal and extend successfully until it begins to overlap with an AGG interruption, where it cannot anneal, resulting in a clear zone in the electropherogram with no PCR products. dTP-F can only start to anneal and extend from the second repeat segment, giving a PCR product consisting of 15 repeats and which results in the first peak in the second cluster. Similarly, the dTP-F primer cannot anneal completely across the next interruption, resulting in another clear zone before the third peak cluster. It will continue to anneal and extend in this repeat segment until it overlaps the 5' repeat flanking sequence. Hence, a uTP PCR peak pattern for a normal allele with 9+9+9 configuration is expected to consist of three clusters of 5 discrete peaks separated by two clear zones of ~18 bp. More peaks in each cluster will be expected where there are more repeats before the primer encounters an interruption or unique repeat-flanking sequences.

FIG. 12B shows an example of a stretch of pure CGG repeat alleles with no AGG interruption. The electropherograms should show acontinuous cascade of peaks of decreasing heights with increasing product sizes, each peak separated from the next by a gap of 3 bp. This is because the dTP-F primer can anneal completely and extend successfully from anywhere along the uninterrupted stretch of CGG repeats, beginning from the 3' end of the repeat region, which gives rise to the shortest PCR products.

Expected Results

Using the primers described herein, one should expect to see dTP-PCR peak patterns that can distinguish samples carrying only normal, AGG-interrupted alleles from samples carrying expanded alleles without AGG interruptions. A schematic illustration of the expected GeneScan electropherogram results of several archetypal allelic forms of FMR1 repeats after dTP-PCR is shown in FIG. 12.

The peaks are detected on the Fam fluorescence detection channels. Alleles with interruptions will result in a discontinuous series of product peaks, while alleles without interruptions will result in a continuous series of product peaks.

Males carry only one X chromosome, hence all males are expected to carry only one FMR1 allele. A normal unaffected male is expected to have only one FMR1 allele of normal length. Assuming that there has been no loss of AGG interruptions, a discontinuous series of discrete dTP-PCR product peaks should be expected (FIG. 12, normal male). In both premutation and full mutation males, a continuous series of dTP peaks should be observed, due to the presence of expanded FMR1 alleles with loss of the 3' AGG interruptions (FIG. 12, premutation and full mutation males). It will not be possible to distinguish a premutation male from a full mutation male as the dTP-PCR does not inform on methylation states, unless the premutation allele is small enough to be sized from the number of dTP-PCR peaks. Exceptions to these predicted patterns may occur in males that are size mosaics, where there are alleles with two or more different lengths in the same sample (15).

Females carry two X chromosomes, hence all females are expected to carry two FMR1 alleles. In a normal female, there should be two FMR1 alleles with repeat lengths in the normal range. Hence, discontinuous peak patterns similar to that of a normal male should be expected (FIG. 12, normal female). In both premutation and full mutation females, a combination of continuous and discontinuous peak patterns should be expected, due to the presence of both normal and expanded alleles (FIG. 12, premutation and full mutation females). Again, this assay cannot distinguish a premutation from a full mutation female as it is not methylation sensitive and cannot inform on the methylation states of the expansions.

Interpretation of GeneScan Results

The dTP-PCR assay was performed on a panel of genotype-known samples, and the actual GeneScan electropherogram results are shown in FIG. 14. A normal male sample (GM04738) shows only the discontinuous dTP peak pattern with gaps of ~18 bp between clusters of discrete peaks. Two gaps here reflect the presence of two AGG interrupions in the repeat region. In the premutation male sample (GM06891), continuous dTP peaks of decreasing heights, 3 bp apart from one another and with peak sizes ranging from 136 bp up to ~400 bp were observed. In a full mutation male (GM06852), a continuous dTP peak pattern similar to that of the premutation male was observed. The peak ladders of both the pre- and full mutation males were not interrupted by gaps with no amplicons, indicating that the 3' most AGG interruption has been lost in both samples.

In a normal female sample (GM04479), the dTP-PCRs showed the expected discontinuous peak patterns with 3 clusters of discrete peaks (FIG. 14, normal female). The clear zones between discrete peak clusters confirm the absence of premutation or full mutation alleles in this female sample, as well as the presence of two AGG interruptions in the repeat region. In the premutation female (GM06907), 3 clusters of dTP peaks are blended with continuous dTP peaks up to ~400 bp, indicating the presence of two types of alleles—the normal allele with two AGG interruptions, and the expanded allele with loss of at least one AGG interruption at the 3' end (FIG. 14, premutation female). The peak clusters are separated from one another by ~18 bp. The continuous dTP peaks were interspersed with the distinct peak clusters. The electropherogram result for the full mutation female (GM07537) is similar to the premuation female, with the normal peak clusters interspersed by continuous peak ladders arising from the expanded alleles. Again, this assay is unable to separate an expansion that is fully methylated i.e. a full mutation from an expansion that is not methylated i.e. a premutation.

Assay Validation

Further validation of the assay was performed on 23 additional DNA samples, consisting of both male and female samples with repeat lengths spanning across the four main allelic genotypes—normal, gray zone, premutation and full mutation (Tables 6 and 7, FIGS. 15 and 16).

As with the 6 samples above, pre- and full expansion samples were easily distinguished from normal samples by the presence of continuous series of peaks where there is an expansion, which is usually accompanied by the loss of AGG interruptions. These series of peaks stretch to beyond 350 bp in both males and females. Normal alleles gave rise to discrete clusters of peaks separated by clear zones where the dTP-F primer fails to anneal across the interruptions. In samples with 2 interruptions, there were three discrete clusters of peaks separated by two clear zones (eg. GM06890, NA07538, FIGS. 15 and 16 respectively). Where there is only 1 interruption in the repeat region, only two peak clusters separated by one clear zone with no amplification peaks were observed (NA20232).

TABLE 6

Male genomic DNA samples from Coriell Cell Repository fines used for assay optimization and validation.

| Coriell ID | No. of CGG repeats as provided by | 5' → 3' repeat pattern (Total no. of repeats) | |
|---|---|---|---|
| | | Direct TP-PCR | Direct PCR Sequencing |
| GM 06890 | 30 | 10 + 9 + 9 {30} | 10 + 9 + 9 (30) |
| GM 04738 | not indicated | 10 + 9 + 9 (30) | 10 + 9 + 9 (30) |
| NA 07174 | 30 [30][A] | 10 + 9 + 9 (30) | 10 + 9 + 9 (30) |
| NA 20244 | 41 [41][A] | 9 + 9 + 21 (41) | 9 + 9 + 21 (41) |
| NA 20232 | 46 [46][A] | 9 + 36 (46) | 9 + 36 (46) |
| NA 20230 | 54 [53][A] | 54 uninterrupted repeats | 54 uninterrupted repeats |
| CD 00014 | 56 [56][A] | 9 + 9 + 36 (56) | 9 + 9 + 36 {56} |
| NA 20231 | 79 [76][A] | 10 + 67 (78) | 10 + 67 (78) |
| GM 06892 | 93 l86][A] | 10 + 82 (93) | 10 + 82 (93) |
| GM 06891 | 118 | Unable to size precisely: expanded allele >128 | PCR successful (~193 rpts); |
| GM 06852 | >200 | Unable to size precisely: expanded allele >128 | PCR and sequencing failed |
| GM 07294 | >200 | Unable to size precisely: expanded allele >128 | — |
| GM07862 | 501-550 | Unable to size precisely: expanded allele >128 | — |

[A]Repeat lengths in brackets are consensus data from a consortium study.

TABLE 7

Female genomic DNA samples from Coriell Cell Repository lines used for assay optimization and validation.

| Coriell ID | No. of CGG repeats as provided by Coriell | Size of largest allele by direct TP-PCR |
|---|---|---|
| NA 07538 | 29/29 [29/29]^ | 29 |
| GM 07175 | 23/30 | 30 |
| GM 04479 | not indicated | 30 |
| NA 20238 | 29/30 [29/30]^ | 30 |
| NA 20243 | 29/41 [29/41]^ | 41 |
| NA 20235 | 29/45 [29/45]^ | 45 |

TABLE 7-continued

Female genomic DNA samples from Coriell Cell Repository lines used for assay optimization and validation.

| Coriell ID | No. of CGG repeats as provided by Coriell | Size of largest allele by direct TP-PCR |
|---|---|---|
| NA 20234 | 31/46 | 46 |
| NA 20236 | 31/55 [31/53]^ | 54 |
| GM 06907 | 29/85 | 91 |
| NA 20240 | 30/85 [30/80]^ | 89 |
| NA 20242 | 30/100 [30/73]^ | 74 |
| GM 06896 | 23/95-120-140 | 115 |
| NA 20239 | 23/200 [20/no consensus]^ | Unable to size precisely: expanded allele >128 |
| GM 07537 | 28-29/>200 | Unable to size precisely: expanded allele >128 |
| GM 05855 | (34/>200) | Unable to size precisely: expanded allele >128 |
| GM 07063 | (32/>200) | Unable to size precisely: expanded allele >128 uninterrupted |

Assay Sensitivity

The sensitivity of this assay was determined by performing the assay on small amounts of genomic DNA obtained from the six samples used for initial assay optimization and validation. The dTP-PCR assay was able to pick out expanded alleles from all premutation and full mutation male and female samples (FIG. 17). In the premutation and full mutation female samples, peak ladders can be detected from as little as 1 ng of genomic DNA, despite the presence of normal alleles that are usually more preferentially amplified (18,20, 21).

Determining FMR1 Repeat Lengths

Discrepancies between the expected and observed sizes of the amplicons, with the dTP-PCR products migrating at about 6 by faster than the expected amplicon sizes were observed. This is due to the enhanced electrophoretic mobility of fragments containing triplet repeats (22). Thus, sizing of the amplicons by capillary electrophoresis to determine repeat lengths may result in under-sizing of the alleles. By using the number of peaks and repeat structures to predict allele lengths, we have successfully overcome the problem of inherent enhanced mobility of triplet repeat-rich fragments over the size standards used during capillary electrophoresis. By analyzing repeat structures, alleles up to ~115 repeats could be sized (Tables 5 and 6). Unlike assays that utilize primers flanking the repeat region for FMR1 expansion detection, there is no preferential amplification of normal alleles over expanded alleles with this current approach, thus avoiding apparent homozygosity issues where a female sample with one normal allele and a second full mutation allele that is refractory to PCR may be mistaken for a female sample that is homozygous for normal alleles:

Summary

The method described herein is technically simple with reliable results that can be obtained within a day. It requires only one PCR setup and is robust enough to detect very large premutation and full mutation alleles in both males and females. Considering a hypothetical sample size of 50,000 males, with current estimates of premutation and full mutation prevalences of approximately 1 in 800 and 1 in 4000 males respectively (28), using this PCR approach as a first-line screen for expansions will result in only ~80 full mutation male samples being channeled for size confirmation by methylation-specific TP-PCR or Southern blot analysis, to separate the premutations from the full mutations. For a similar sample size of 50,000 females, with known FXS frequency of 1 in 6000 females and premutation allele prevalence of 1 in 259 females (28,29), and taking into consideration that moderate expansions up to ~100 repeats in the premutation range can be sized, only ~200 (or ~0.4%) are premutation and full mutation females that require follow up analysis by methylation-specific TP-PCR or Southern blot analysis.

Used as a rapid first screen for FMR1 expansions, this assay can drastically reduce the cost and effort of FXS diagnosis. Unlike most PCR assays, there is no issue of apparent homozygosity of normal alleles in pre- and full mutation females. It is also able inform on the positions of the AGG interruptions in the FMR1 repeat region, which may be useful to consider for informed and accurate clinical diagnosis and counseling.

Example 5

Direct Triplet-Primed PCR (dTP-PCR) Assay for Distinguishing Between Normal and Expanded FMR1 by Melting Curve Analysis Assay Overview The PCR strategy is similar to Example 4. The principal feature of the PCR design remained unchanged, with a tailed forward primer annealing to the repeat region, a tail primer complementary to the tail sequence of the forward primer, and a reverse primer annealing to the unique sequence 3' of the repeat region. The primers are not fluorescently labeled, and amplification products are detected using SYBR green nucleic acid dye, which is added into the PCR mix prior to thermocycling. SYBR green dye binds to double stranded DNA amplification products. Melting curve analysis immediately follows the PCR thermocycling steps. Both PCR thermocycling and melting curve analysis are performed consecutively on the LightCycler480 instrument, with no need for additional sample transfers. Two categories of melting peak patterns will be seen, one arising from normal repeats and the other arising from expanded repeats.

Direct TP-PCR

Minor modifications to the primer sequences were made but the principle features of the PCR design and thermocycling conditions are identical to Example 4 (Table 4). SYBR green nucleic acid dye was added to the PCR mixture prior to thermocycling. Thermocycling and melting programs were performed consecutively on the LightCycler480.

Melting Curve Analysis

20 µl of dTP-PCR products were subjected to a melting programme consisting of denaturation at 95° C. for 1 min, a temperature-hold step at 60° C. for 1 min, and then slow temperature ramping from 60° C. to 95° C., with 50 readings of fluorescence intensity per degree during temperature ramping. The Lightcycler480 software was used to collect fluorescence intensities and convert the data into melting curve and melting peak plots Results Clear differences in melting peak patterns and melting temperatures between normal and expanded alleles were observed (FIG. 18). It was observed that dTP-PCR products of normal alleles gave melting profiles with two peaks, both below 87° C., followed by a sharp drop in the melting profile at 88° C. PCR products of expanded alleles of premutation and full mutation males and females gave multiple melting peaks, with at least one peak above 89° C. Hence, we would be able to detect the presence of expanded alleles, and distinguish them from normal alleles, by analyzing the shapes and melting temperatures of the melting peaks.

Example 6

Direct Triplet-Primed PCR (dTP-PCR) Assay for Distinguishing Between Normal and Expanded FMR1 Alleles Using a Chip-Based Microfluidic Platform Assay Overview The PCR strategy is similar to Example 5, but without the adding SYBR green dye into the PCR mixture. PCR products were resolved on a DNA chip in the Agilent Bioanalyzer 2100. In general, we should expect to see two categories of electrophoretic profiles, one arising from normal alleles and another arising from expanded alleles.

Direct TP-PCR

The principle features of the PCR design and thermocycling conditions are identical to Example 4. Primers used were the same as in Example 4, except that none of the primers need to be fluorescent-labeled for this assay.

Resolution of PCR Products on the Bioanalyzer

The Agilent DNA 1000 chips were prepared as per the manufacturer's protocol, with slight modifications. Briefly, each DNA 1000 chip can analyze 12 samples in ~35 min. After the chip has been primed with the gel-dye mix (provided in kit), 3 µl of either uTP or mTP PCR products and 3 µl of DNA marker (provided in kit) were added into each of the 12 sample wells. 1 µl of DNA ladder (provided in kit) and 5 µl of DNA marker were added into a designated well. The chip is then loaded into the Bioanalyzer after brief vortexing. The Bioanalyzer software then collects the fluorescence data from each well and generates the electrophoretic profiles for each sample sequentially.

Results

Clear differences in the electrophoretic profiles of normal and expanded alleles can be observed (FIG. 19). The dTP PCR products of normal alleles gave discrete peaks (normal samples). In contrast, dTP PCR products of expanded alleles gave a series of merged peaks of decreasing heights, forming an electrophoretic pattern that is distinct from normal samples (premutation and frill mutation samples). Although the size resolution of peaks on the Bioanalyzer is lower than on the ABI Genetic Analyzer, we were still able to distinguish normal from expanded alleles based on the general electrophoretic profiles of the PCR amplicons.

Example 7

5' Direct Triplet-Primed PCR (dTP-PCR) Assay for Detecting Expanded FMR1 Alleles in Male and Female Samples Overview This is a modification of the originally described 3' direct TP-PCR (3' dTP-PCR; see Example 4) assay. The primers for the 5' dTP-PCR are designed against the 5' end of the repeat region (FIG. 20). The 5' dTP-PCR assay should be performed alongside the 3' dTP-PCR to avoid false null or misdiagnosis of full expansions, which may occur if only one PCR was performed for samples with rare deletions in the sequence adjacent to the repeat region.

PCR Conditions

5' dTP-PCR conditions are as described for 3' dTP-PCR, except for the components of the dNTP mix. While the 3' dTP-PCR used a dNTP mix consisting of 0.2 mM each of dATP, dGTP, dTTP and dCTP, 5' dTP-PCR required a dNTP mix consisting of 0.2 mM each of dATP, dTTP and dCTP, 0.15 mM of 7-deaza-dGTP and 0.05 mM of dGTP. Primer sequences and concentrations are as described in Table 8. Thermal cycling and capillary electrophoresis conditions were kept the same as 3' dTP-PCR.

TABLE 8

Primers for 5' direct TP-PCR

| Primer | 5' → 3' sequence | Genbank ID nucleotides | Concentrations |
|---|---|---|---|
| Fam-c3 (SEQ ID NO: 21) | Fam-TTCGGTTTCACTTCCGGTGGA GGGCCGCCT | X61378: 2611→2640 | 0.2 µM |
| 5dTP-R (SEQ ID NO: 22) | ATGGCTATGCGTAGGGTCAAA − CAGT(CCG)$_5$ | | 0.02 µM |
| Tail-R (SEQ ID NO: 23) | ATGGCTATGCGTAGGGTCAAA − CAGT | | 0.2 µM |

Interpretation of Results

The 5' dTP-PCR was performed on a panel of genotype known samples consisting of male and female samples with repeat lengths covering the range of FMR1 genotypes. FIG. 21 shows electropherograms characteristic of the three main FMR1 genotypes. The peak patterns are similar to those of 3' dTP-PCR, with discontinuous peak patterns observed in normal samples and continuous peak ladders in premutation and full mutation samples. While the 3' dTP-PCR is more sensitive to AGG interruptions at the 3' end of the repeats, the 5' dTP-PCR is more sensitive towards the detection of 5' AGG interruptions, being able to pick out 5' AGG interruptions where the 3' dTP-PCR could not. Hence, alleles carrying the pre- and full mutation repeats with only one AGG interruption at the 5' end may show an interrupted peak ladder pattern from the 5' dTP-PCR results but a continuous peak ladder from 3' dTP-PCR. The results from 5' dTP-PCR support earlier results from 3' dTP-PCR. Where sizing was possible, allele size information from 5' and 3' dTP-PCRs were similar.

Example 8

5' Methylation-Specific Triplet-Primed PCR (msTP-PCR) for Detection of AGG-Interspersed and Uninterrupted CGG Repeats in Normal, Permutation and Full Mutation FMR1 Alleles Overview This is a modification of the originally described 3' methylation-specific TP-PCR (3' msTP-PCR; see Example 1) assay. The primers for the 5' msTP-PCR are designed against the 5' end of the repeat region. Similar to the 3' duplex msTP-PCR previously described, there are two unique sets of primers, one each for the amplification of the unmethylated and methylated alleles. The 5' msTP-PCR assay should be performed alongside the 3' msTP-PCR to avoid false null or misdiagnosis of full expansions, which may occur if only either was performed for samples with rare deletions in the sequence adjacent to the repeat region.

PCR Conditions

5' msTP-PCR is performed on sodium bisulfite treated genomic DNA. The method for sodium bisulfite treatment is as described for 3' msTP-PCR. The components that make up the PCR mixture are also similar to 3' msTP-PCR, with the exception of the primers used and their concentrations (Table 9). Thermal cycling and capillary electrophoresis conditions were kept the same as 3' msTP-PCR.

TABLE 9

Primers for 5' duplex msTP-PCR

| Primer | 5' → 3' sequence | Genbank ID nucleotides | Concentrations |
|---|---|---|---|
| 5' uTP-PCR | | | |
| 5uTP-F (SEQ ID NO: 24) | AAACACTCAACTCCATTTC AATTTCACTTCCA | X61378: 2595→2628 | 0.3 µM |
| 5uTP-R (SEQ ID NO: 25) | CGACTGTTTGACCCTACCT TA(TTG)₉ | — | 0.03 µM |
| Fam-5uTP-TailF (SEQ ID NO: 28) | Fam-CGACTGTTTGACCCT ACCTTA | — | 0.3 µM |
| 5' mTP-PCR | | | |
| 5mTP-F (SEQ ID NO: 26) | GCCGCTACCAAAAAACGTA CGACAACGCG | X61378: 2693→2721 | 0.2 µM |
| 5mTP-R (SEQ ID NO: 27) | ATTCCATCCCAGTTTGTCA GC(TCG)₈ | — | 0.02 µM |
| Ned-5mTP-TailF (SEQ ID NO: 29) | Ned-ATTCCATCCCAGTTT GTCAGC | — | 0.2 µM |

Interpretation of Results

The 5' duplex msTP-PCR was performed on a panel of genotype-known samples consisting of males and females with the three main FMR1 genotypes (FIG. 22). Electropherogram peaks are similar to those of 3' msTP-PCR, with discontinuous peak patterns observed in normal samples and continuous peak ladders in premutation and full mutation samples. The 5' duplex msTP-PCR is more sensitive towards the detection of 5' AGG interruptions. Hence, alleles carrying the pre- and full mutation repeats with only one AGG interruption at the 5' end will show an interrupted peak ladder pattern from the 5' msTP-PCR results but a continuous peak ladder from 3' msTP-PCR. The results from 5' msTP-PCR support earlier results from 3' msTP-PCR. In the full mutation male (GM06852), there were low levels of amplification by both 3' and 5' uTP PCRs, indicating a low level of methylation mosaicism in this sample. In the premutation female (GM06907), the premutation allele was only weakly detected by both 5' and 3' uTP-PCRs, and in the full mutation female (GM07537), the normal allele was weakly detected by both 5' and 3' mTP-PCRs, indications of extremely skewed X chromosome at this locus.

Example 9

Capillary Electrophoresis Data of 3' and 5' Direct TP-PCRs on Whole Genome Amplified (by Multiple Displacement Amplification) Single Cell DNA Multiple displacement amplification (MDA) was performed on single cells obtained from lymphoblastoid cell cultures. 3' and 5' direct TP-PCRs were performed on MDA products. The amplification and capillary electrophoresis conditions were identical to those for genomic DNA referred to in Example 4. 3' direct TP-PCR was carried out as in Example 4. 5' direct TP-PCR was carried out as in Example 7.

As can be seen in FIG. 23, both 3' and 5' direct TP-PCR can be used on whole genome amplified single cell DNA.

Example 10

5' and 3' Direct and Methylation-Specific uTP-PCR Reactions Performed in the Absence of the Tail Primers All PCR conditions and capillary electrophoresis conditions were as described for triplet-primed PCRs with three primers. PCR amplification efficiencies of the expanded alleles were less robust than the original triplet-primed PCRs with three primers, especially in female samples. Amplification with only a tailed, repeat annealing primer and a flanking sequence-annealing primer can be improved by optimisating PCR conditions for this combination of primers. Nonetheless, even with suboptimal amplification conditions, the assays were in principle still possible to perform without the tail primers, with slight differences between the electropherograms of expanded and normal alleles (see FIGS. 24a-d).

Example 11

5' and 3' Direct and Methylation-Specific uTP-PCR Reactions Performed in the Absence of the Tail Primers.

All PCR conditions and capillary electrophoresis conditions were as described for the triplet-primed PCRs with three primers. PCR amplification efficiencies of the expanded alleles were less robust than the original triplet-primed PCRs with three primers, especially in female samples. Amplification with only a repeat annealing primer without a tail sequence and a flanking sequence-annealing primer can be optimised by adjusting PCR conditions. Under these suboptimal conditions, the repeat annealing primers appear to anneal across interruptions and the unique flanking sequences 5' or 3' of the repeats, resulting in stutter peaks that may interfere with the differentiation of normal from expanded alleles, particularly in females (see FIGS. 25a-d). Nonetheless, further optimization with more stringent conditions should allow these combinations of primers to be used as well.

Example 12

Multiplexing both 5' and 3' Duplex msTP-PCRs in One Single Reaction (i.e. 12 Primers, Annealing Against 4 Unique Sequences Following Sodium Bisulfite Treatment)

FIG. 26 shows a schematic illustration of the principle of multiplex methylation-specific triplet-primed PCR. Sodium bisulfite treatment of native genomic DNA differentially modifies unmethylated and methylated alleles on both the sense and antisense strands, resulting in four unique and non-complementary sequences. In order for both 5' and 3' msTP-PCRs to be multiplexed in a single reaction, each set of primers must be designed against separate strands of the modified unmethylated and methylated, sense and antisense sequences. It will also be necessary to label each of the tail primers with fluorescent labels that can be detected in different fluorescent channels during capillary electrophoresis.

Applications

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A closed-tube method for screening for a trinucleotide repeat sequence in a biological sample, wherein said method comprises the steps of
   a) contacting a nucleic acid sequence obtained from the biological sample under amplification conditions with:
      i) a first primer, wherein said first primer has a target sequence in a region 3' or 5' of a trinucleotide repeat sequence in the nucleic acid sequence;
      ii) a second primer, wherein said second primer has a target sequence, all of which is within the trinucleotide repeat sequence in the nucleic acid sequence and a unique 5' tail sequence; and
      iii) a third primer, wherein the target sequence of the said third primer is within the unique 5' tail sequence of the second primer to generate an amplified product comprising a trinucleotide repeat sequence; and
   b) analyzing said amplified product using DNA melt curve analysis.

2. The method of claim 1, wherein the trinucleotide repeat sequence is selected from (CAG)n, (CGG)n, (GCC)n, (GAA)n or (CTG)n wherein n is from 1 to 250.

3. The method of claim 2 further comprising the step of analysing the amplified product to determine the range of n, and comparing the result of said analysis against a standard to determine whether the amplified product corresponds to that of a normal allele, a full mutation allele, a pre-mutation allele or a gray zone allele in a male or female subject.

4. The method of claim 2, wherein the trinucleotide repeat is (CGG)n and wherein n from 5 to 44 corresponds to that of a normal allele; n from 45-54 corresponds to that of a gray zone allele; n from 55-200 corresponds to that of a pre-mutation allele and n of more than 200 corresponds to that of a full mutation allele.

5. The method of claim 1, further comprising screening the amplified product for the presence of an interrupting sequence in the trinucleotide repeat sequence.

6. The method of claim 1, comprising pre-treating the nucleic acid sequence with a reagent which selectively modifies unmethylated cytosine residues in the nucleic acid sequence.

7. The method of claim 6 in which the reagent comprises sodium bisulphite, the reagent modifies an unmethylated (CCG)n sequence to (TTG)n and a methylated (CCG)n to (TCG)n and in which the second primer is complementary to the treated methylated or unmethylated trinucleotide repeat sequence.

8. A closed-tube method for screening for a trinucleotide repeat sequence in a biological sample, wherein said method comprises:
   a) contacting a nucleic acid sequence obtained from the biological sample under amplification conditions with:
      i) a first primer, wherein said first primer has a target sequence in a region 3' or 5' of a trinucleotide repeat sequence in the nucleic acid sequence; and
      ii) a second primer, wherein said second primer has a target sequence, all of which is within the trinucleotide repeat sequence in the nucleic acid sequence to generate an amplified product comprising a trinucleotide repeat sequence; and
   b) analyzing said amplified product using DNA melt curve analysis.

9. The method of claim 8, wherein the second primer comprises a unique 5' tail sequence.

10. The method of claim 8, further comprising detection of the amplified product with a nucleic acid-intercalating fluorophore.

11. The method of claim 8, further comprising the step of analysing the amplified product to determine the presence of a trinucleotide repeat and comparing the result of said analysis against a standard to determine whether the amplified product corresponds to that of a normal allele, a full mutation allele, or a pre-mutation allele in a male or female subject.

12. The method of claim 8, comprising pre-treating the nucleic acid sequence with a reagent which selectively modifies unmethylated cytosine residues in the trinucleotide repeat sequence.

13. The method of claim 12 in which the reagent comprises sodium bisulphite, the reagent modifies an unmethylated (CCG) sequence to (TTG) and a methylated (CCG) to (TCG) and in which the second primer is complementary to the treated methylated or unmethylated trinucleotide repeat sequence.

14. The method of claim 13, further comprising the step of analysing the amplified product to determine if the (CCG) sequence is methylated or unmethylated in a male or female subject.

15. A single-tube PCR assay method for screening for a trinucleotide repeat sequence in a biological sample, wherein said method comprises:
   a) contacting a nucleic acid sequence obtained from the biological sample under amplification conditions, wherein said nucleic acid has been pre-treated with a reagent which selectively modifies unmethylated cytosine residues in the nucleic acid sequence, with:
      i) a first primer, wherein said first primer has a target sequence in a region 3' or 5' of a trinucleotide repeat sequence in the nucleic acid sequence;
      ii) a second primer, wherein said second primer has a target sequence, all of which is within the trinucleotide repeat sequence in the nucleic acid sequence and said primer is complementary to a methylated trinucleotide repeat sequence; and
      iii) a further second primer, wherein said further second primer has a target sequence, all of which is within the trinucleotide repeat sequence in the nucleic acid sequence and said primer is complementary to an unmethylated trinucleotide repeat sequence to generate an amplified product comprising a trinucleotide repeat sequence; and b) analyzing said amplified product using DNA melt curve analysis or capillary electrophoresis.

16. The method of claim 15, wherein said first primer has a target sequence in a region 3' of a trinucleotide repeat sequence in the nucleic acid sequence.

17. The method of claim 15, wherein the second primer and said further second primer comprise a unique 5' tail sequence.

18. The method of claim 17, wherein said method further comprises contacting the nucleic acid sequence with a third primer and a further third primer, wherein the target sequence of the third primer is within the unique 5' tail sequence of the second primer and the target sequence of the further third primer is within the unique 5' tail sequence of said further second primer.

19. The method of claim 15, further comprising detection of the amplified product with a nucleic acid-intercalating fluorophore when DNA melt curve analysis is used in step b).

20. The method of claim 15, further comprising the step of analysing the amplified product to determine the presence of a trinucleotide repeat and comparing the result of said analysis against a standard to determine whether the amplified product corresponds to that of a normal allele, a full mutation allele or a pre-mutation allele in a male or female subject.

21. The method of claim 15, further comprising the step of analysing the amplified product to determine if the trinucleotide sequence is methylated or unmethylated in a male or female subject.

22. The method of claim 15, wherein the first primer has a target sequence in a region 3' or 5' of the methylated trinucleotide repeat sequence in the nucleic acid sequence; and the method further comprises the use of a further first primer that has a target sequence in a region 3' or 5' of the unmethylated trinucleotide repeat sequence in the nucleic acid sequence.

23. The closed-tube method of claim 1, wherein the method further comprises detection of the amplified product with a nucleic acid-intercalating fluorophore.

24. The closed-tube method of claim 7, further comprising analyzing the amplified products from the amplification of the treated methylated and unmethylated trinucleotide repeat sequences to determine if the trinucleotide sequence is methylated or unmethylated in a male or female subject.

25. The single-tube PCR assay method of claim 15, wherein step b) is performed by analyzing said amplified product using capillary electrophoresis.

26. The single-tube PCR assay method of claim 25, wherein at least one primer comprises a detectable label.

27. The single-tube PCR assay method of claim 25, further comprising determining whether the amplified product corresponds to that of a normal allele, a full mutation allele, or a pre-mutation allele in a male or female Fragile X syndrome patient.

* * * * *

```
                        SEQUENCE LISTING

<160> NUMBER OF SEQ ID NOS: 31

<210> SEQ ID NO 1
<211> LENGTH: 48
<212> TYPE: DNA
<213> ORGANISM: Homo sapiens

<400> SEQUENCE: 1
cgactgtttg accctacctt acaacaacaa caacaacaac aacaacaa              48

<210> SEQ ID NO 2
<211> LENGTH: 29
<212> TYPE: DNA
<213> ORGANISM: Homo sapiens

<400> SEQUENCE: 2
tgtttttgag aggtgggttg tgggtgttt                                   29

<210> SEQ ID NO 3
<211> LENGTH: 21
<212> TYPE: DNA
<213> ORGANISM: Homo sapiens

<400> SEQUENCE: 3
cgactgtttg accctacctt a                                           21

<210> SEQ ID NO 4
<211> LENGTH: 45
<212> TYPE: DNA
<213> ORGANISM: Homo sapiens

<400> SEQUENCE: 4
attccatccc agtttgtcag ccgacgacga cgacgacgac gacga                 45

<210> SEQ ID NO 5
<211> LENGTH: 29
<212> TYPE: DNA
<213> ORGANISM: Homo sapiens

<400> SEQUENCE: 5
cgttttcgag aggtgggttg cgggcgttc                                   29

<210> SEQ ID NO 6
<211> LENGTH: 21
<212> TYPE: DNA
<213> ORGANISM: Homo sapiens

<400> SEQUENCE: 6
attccatccc agtttgtcag c                                           21

<210> SEQ ID NO 7
<211> LENGTH: 29
<212> TYPE: DNA
<213> ORGANISM: Homo sapiens

<400> SEQUENCE: 7
agccccgcat tccaccacca gctcctcca                                   29
```

-continued

```
<210> SEQ ID NO 8
<211> LENGTH: 42
<212> TYPE: DNA
<213> ORGANISM: Homo sapiens

<400> SEQUENCE: 8
taccgatacg catcccagtt tgtcagccgg cggcggcggc gg                    42

<210> SEQ ID NO 9
<211> LENGTH: 25
<212> TYPE: DNA
<213> ORGANISM: Homo sapiens

<400> SEQUENCE: 9
taccgatacg catcccattt gtcag                                      25

<210> SEQ ID NO 10
<211> LENGTH: 30
<212> TYPE: DNA
<213> ORGANISM: Homo sapiens

<400> SEQUENCE: 10
gcacttccac caccagctcc tccatcttct                                 30

<210> SEQ ID NO 11
<211> LENGTH: 42
<212> TYPE: DNA
<213> ORGANISM: Homo sapiens

<400> SEQUENCE: 11
taccattacg catcccgatt tgtcttacgg cggcggcggc gg                    42

<210> SEQ ID NO 12
<211> LENGTH: 27
<212> TYPE: DNA
<213> ORGANISM: Homo sapiens

<400> SEQUENCE: 12
taccattacg catcccgatt tgtctta                                    27

<210> SEQ ID NO 13
<211> LENGTH: 27
<212> TYPE: DNA
<213> ORGANISM: Homo sapiens

<400> SEQUENCE: 13
caacaacaac aacaacaaca acaacaa                                    27

<210> SEQ ID NO 14
<211> LENGTH: 24
<212> TYPE: DNA
<213> ORGANISM: Homo sapiens

<400> SEQUENCE: 14
cgacgacgac gacgacgacg acga                                       24

<210> SEQ ID NO 15
<211> LENGTH: 15
<212> TYPE: DNA
<213> ORGANISM: Homo sapiens

<400> SEQUENCE: 15
cggcggcggc ggcgg                                                 15
```

<210> SEQ ID NO 16
<211> LENGTH: 21
<212> TYPE: DNA
<213> ORGANISM: Homo sapiens

<400> SEQUENCE: 16
cgactgtttg accctacctt a                                      21

<210> SEQ ID NO 17
<211> LENGTH: 21
<212> TYPE: DNA
<213> ORGANISM: Homo sapiens

<400> SEQUENCE: 17
attccatccc agtttgtcag c                                      21

<210> SEQ ID NO 18
<211> LENGTH: 27
<212> TYPE: DNA
<213> ORGANISM: Homo sapiens

<400> SEQUENCE: 18
taccgatacg catcccagtt tgtcagc                                27

<210> SEQ ID NO 19
<211> LENGTH: 27
<212> TYPE: DNA
<213> ORGANISM: Homo sapiens

<400> SEQUENCE: 19
taccattacg catcccgatt tgtctta                                27

<210> SEQ ID NO 20
<211> LENGTH: 23
<212> TYPE: DNA
<213> ORGANISM: Homo sapiens

<400> SEQUENCE: 20
ggttgcgggc gttcgaggtt tag                                    23

<210> SEQ ID NO 21
<211> LENGTH: 30
<212> TYPE: DNA
<213> ORGANISM: Homo sapiens

<400> SEQUENCE: 21
ttcggtttca cttccggtgg agggccgcct                             30

<210> SEQ ID NO 22
<211> LENGTH: 40
<212> TYPE: DNA
<213> ORGANISM: Homo sapiens

<400> SEQUENCE: 22
atggctatgc gtagggtcaa acagtccgcc gccgccgccg                  40

<210> SEQ ID NO 23
<211> LENGTH: 25
<212> TYPE: DNA
<213> ORGANISM: Homo sapiens

<400> SEQUENCE: 23
atggctatgc gtagggtcaa acagt                                  25

<210> SEQ ID NO 24
<211> LENGTH: 32
<212> TYPE: DNA
<213> ORGANISM: Homo sapiens

<400> SEQUENCE: 24
aaacactcaa ctccatttca atttcacttc ca                           32

<210> SEQ ID NO 25
<211> LENGTH: 48
<212> TYPE: DNA
<213> ORGANISM: Homo sapiens

<400> SEQUENCE: 25
cgactgtttg accctacctt attgttgttg ttgttgttgt tgttgttg          48

<210> SEQ ID NO 26
<211> LENGTH: 29
<212> TYPE: DNA
<213> ORGANISM: Homo sapiens

<400> SEQUENCE: 26
gccgctacca aaaacgtac gacaacgcg                                29

<210> SEQ ID NO 27
<211> LENGTH: 45
<212> TYPE: DNA
<213> ORGANISM: Homo sapiens

<400> SEQUENCE: 27
attccatccc agtttgtcag ctcgtcgtcg tcgtcgtcgt cgtcg             45

<210> SEQ ID NO 28
<211> LENGTH: 21
<212> TYPE: DNA
<213> ORGANISM: Homo sapiens

<400> SEQUENCE: 28
cgactgtttg accctacctt a                                       21

<210> SEQ ID NO 29
<211> LENGTH: 21
<212> TYPE: DNA
<213> ORGANISM: Homo sapiens

<400> SEQUENCE: 29
attccatccc agtttgtcag c                                       21

<210> SEQ ID NO 30
<211> LENGTH: 24
<212> TYPE: DNA
<213> ORGANISM: Homo sapiens

<400> SEQUENCE: 30
gctgtgaagg ttgctgttcc tcat                                    24

```
<210> SEQ ID NO 31
<211> LENGTH: 24
<212> TYPE: DNA
<213> ORGANISM: Homo sapiens

<400> SEQUENCE: 31
tccagaatct cttccagagc gtgc                                              24
```